(12) United States Patent
Goodwill et al.

(10) Patent No.: US 9,763,594 B2
(45) Date of Patent: Sep. 19, 2017

(54) MAGNETIC PARTICLE IMAGING DEVICES AND METHODS

(71) Applicant: The Regents of the University of California, Oakland, CA (US)

(72) Inventors: Patrick W. Goodwill, San Francisco, CA (US); Steven M. Conolly, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/971,768

(22) Filed: Dec. 16, 2015

(65) Prior Publication Data

US 2016/0135710 A1 May 19, 2016

Related U.S. Application Data

(63) Continuation of application No. 14/328,549, filed on Jul. 10, 2014, now Pat. No. 9,274,084, which is a
(Continued)

(51) Int. Cl.
| | |
|---|---|
| *G01R 33/02* | (2006.01) |
| *A61B 5/05* | (2006.01) |
| *G01R 33/10* | (2006.01) |
| *G01R 33/12* | (2006.01) |
| *G01N 27/72* | (2006.01) |
| *A61B 5/00* | (2006.01) |

(52) U.S. Cl.
CPC ........... *A61B 5/0515* (2013.01); *G01N 27/72* (2013.01); *G01R 33/10* (2013.01);
(Continued)

(58) Field of Classification Search
CPC .... G01N 27/72; G01R 33/10; G01R 33/1276; A61B 5/0515
See application file for complete search history.

(56) References Cited

U.S. PATENT DOCUMENTS

| | | | |
|---|---|---|---|
| 4,538,130 | A | 8/1985 | Gluckstern et al. |
| 4,545,384 | A | 10/1985 | Kawachi |

(Continued)

FOREIGN PATENT DOCUMENTS

| | | |
|---|---|---|
| WO | WO 2004091395 | 10/2004 |
| WO | WO 2008099331 | 8/2008 |
| WO | WO 2010008478 | 1/2010 |
| WO | WO 2011010243 | 1/2011 |

OTHER PUBLICATIONS

Goodwill et al. "Multidimensional x-space Magnetic particle imaging," Ieee Transactions on Medical Imaging, 30(9): (2011) 1581-1590 ISSN 1558-254X.

*Primary Examiner* — Daniel Miller
(74) *Attorney, Agent, or Firm* — Venable LLP; Henry J. Daley

(57) ABSTRACT

A magnetic particle imaging device is provided. The device includes a magnetic field source configured to produce a magnetic field having a non-saturating magnetic field region, an excitation signal source configured to produce an excitation signal in the non-saturating magnetic field region that produces a detectable signal from magnetic particles in the non-saturating magnetic field region, and a signal processor configured to convert a detected signal into an image of the magnetic particles. Aspects of the present disclosure also include methods of imaging magnetic particles in a sample, and methods of producing an image of magnetic particles in a subject. The subject devices and methods find use in a variety of applications, such as medical imaging applications.

35 Claims, 60 Drawing Sheets

Related U.S. Application Data continuation of application No. 13/050,779, filed on Mar. 17, 2011, now Pat. No. 8,884,617, which is a continuation-in-part of application No. 12/737,214, filed as application No. PCT/US2009/003764 on Jun. 23, 2009, now Pat. No. 8,847,592.

(60) Provisional application No. 61/340,542, filed on Mar. 17, 2010, provisional application No. 61/442,229, filed on Feb. 12, 2011, provisional application No. 61/074,931, filed on Jun. 23, 2008.

(52) U.S. Cl.
CPC ........ *G01R 33/1276* (2013.01); *A61B 5/7239* (2013.01); *A61B 2576/00* (2013.01)

(56) References Cited

U.S. PATENT DOCUMENTS

| | | |
|---|---|---|
| 5,004,983 A | 4/1991 | Proksa et al. |
| 5,510,711 A | 4/1996 | Molyneaux et al. |
| 2003/0085703 A1 | 5/2003 | Gleich |
| 2005/0073309 A1 | 4/2005 | Williams et al. |
| 2006/0211938 A1 | 9/2006 | Gleich et al. |
| 2006/0248944 A1 | 11/2006 | Gleich |
| 2007/0258908 A1 | 11/2007 | Lanza et al. |
| 2008/0218162 A1 | 9/2008 | Ruhrig |
| 2008/0309330 A1 | 12/2008 | Ohyu et al. |
| 2009/0115415 A1 | 5/2009 | Weaver et al. |
| 2010/0033171 A1 | 2/2010 | Gleich et al. |
| 2010/0052668 A1 | 3/2010 | Gleich et al. |

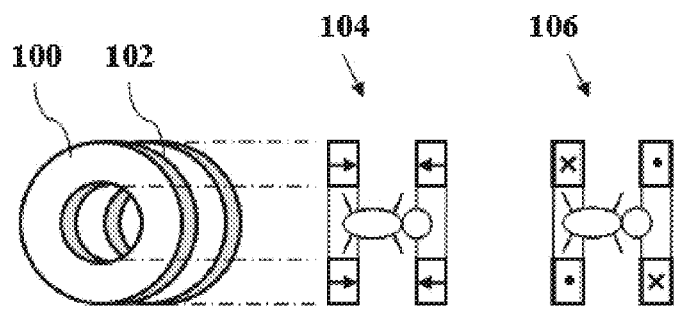
FIG. 1A
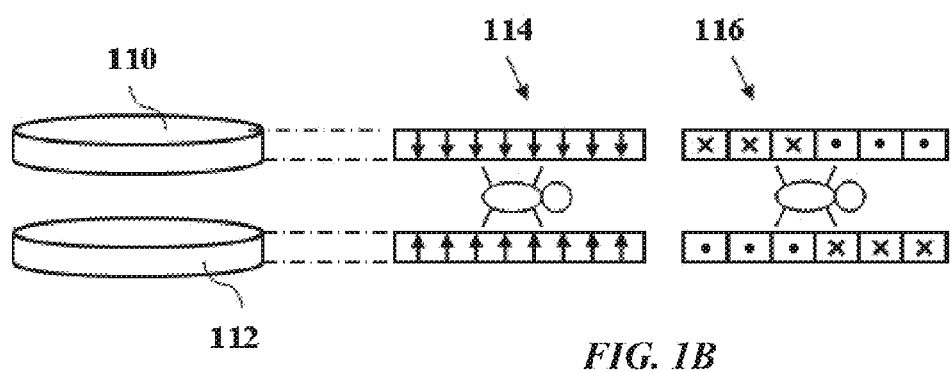
FIG. 1B
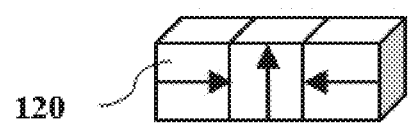
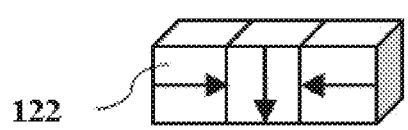
FIG. 1C

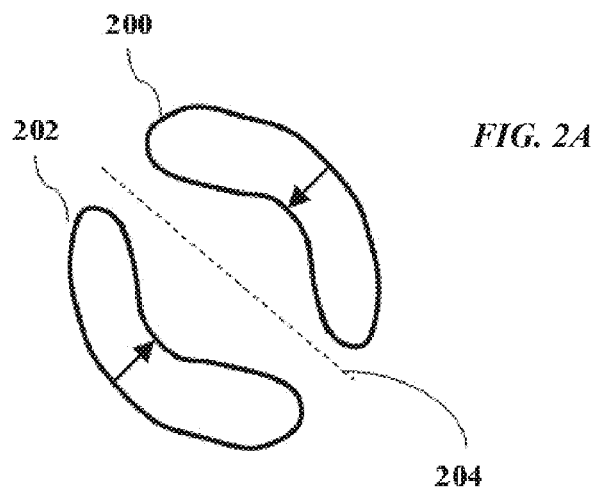
FIG. 2A
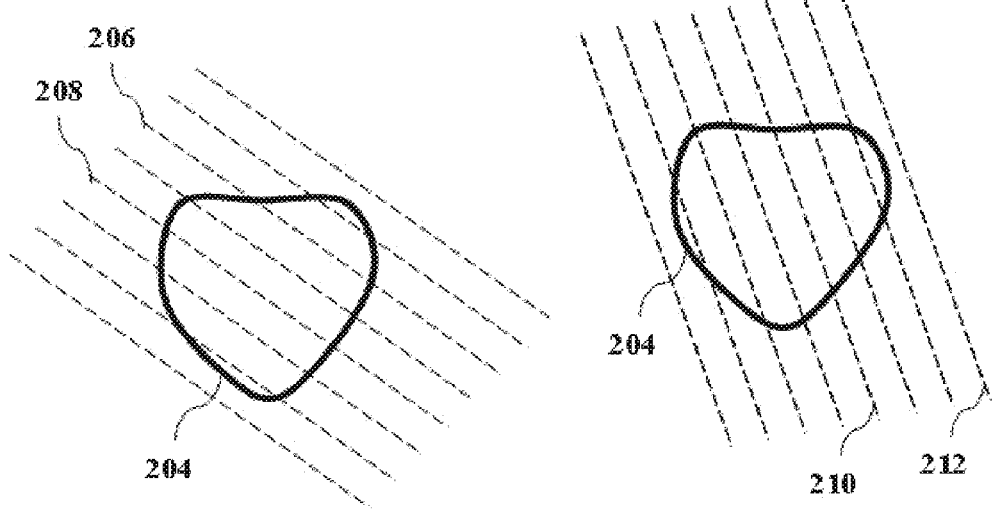
FIG. 2B
FIG. 2C

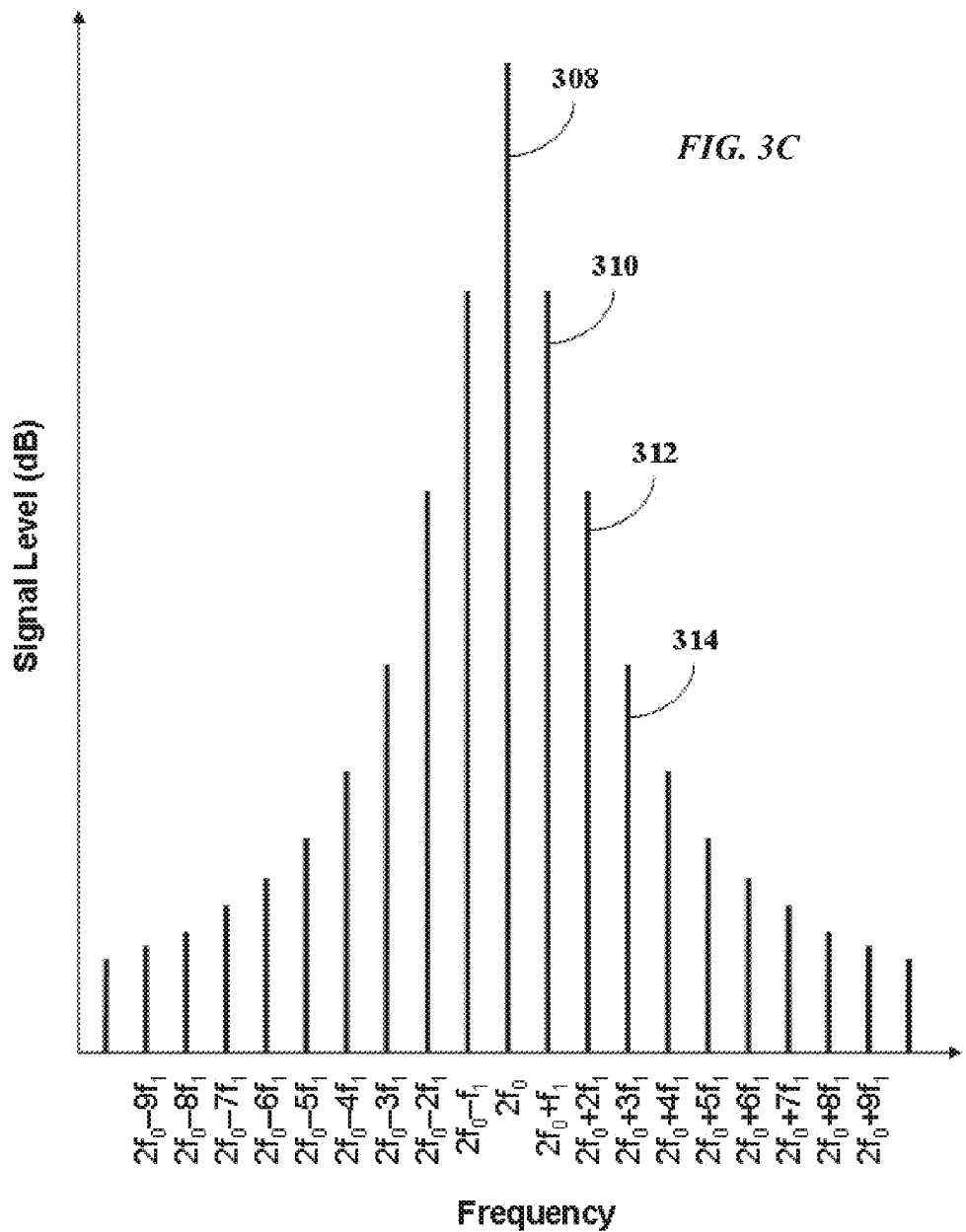

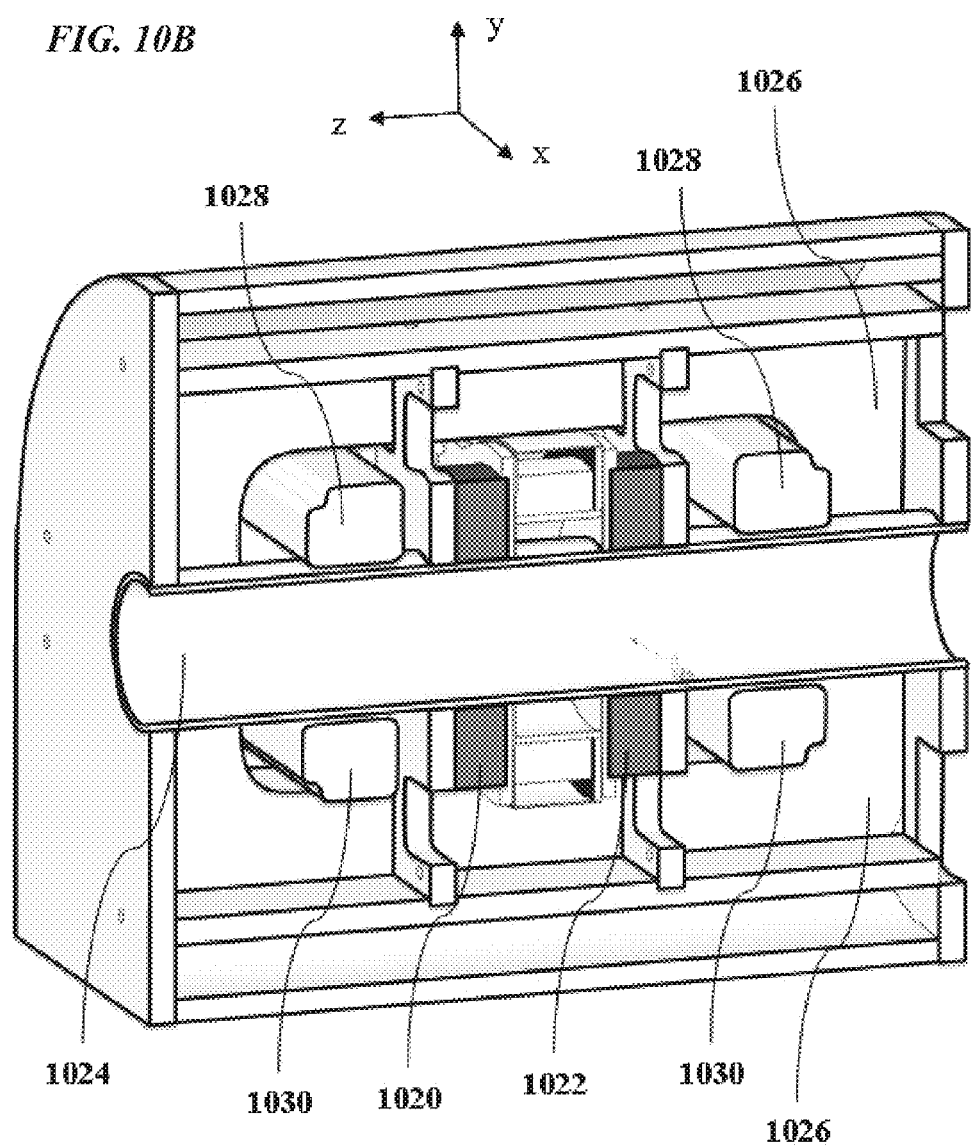

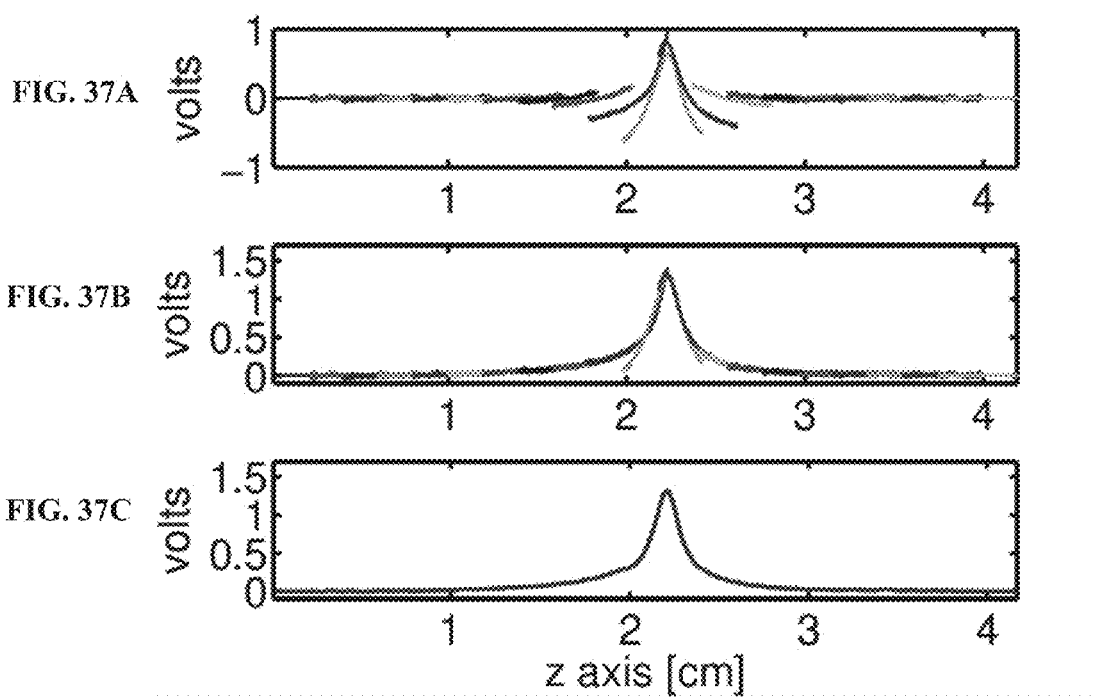

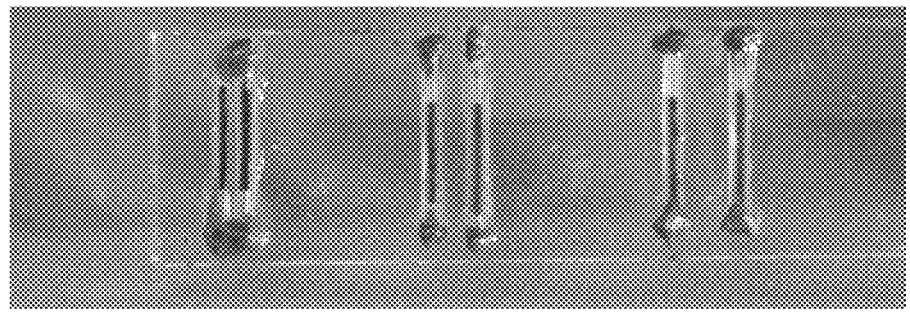
FIG. 49A
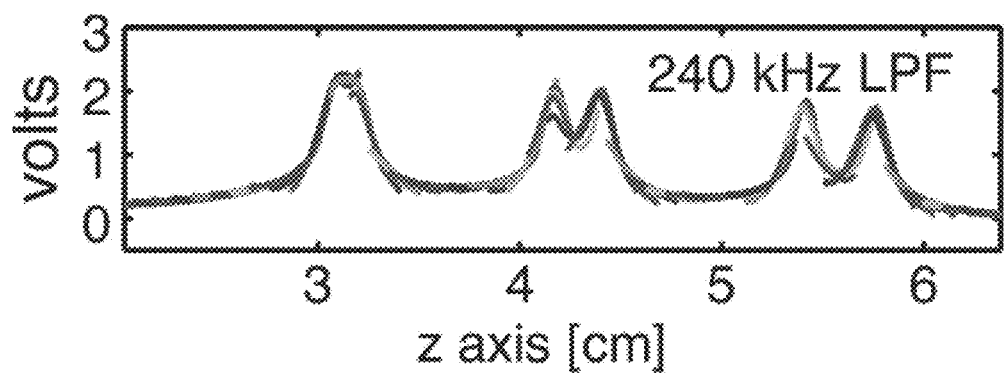
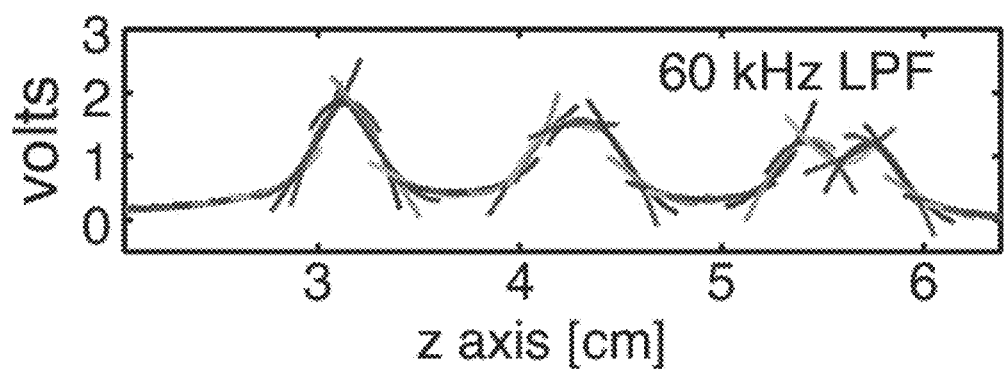
FIG. 49B

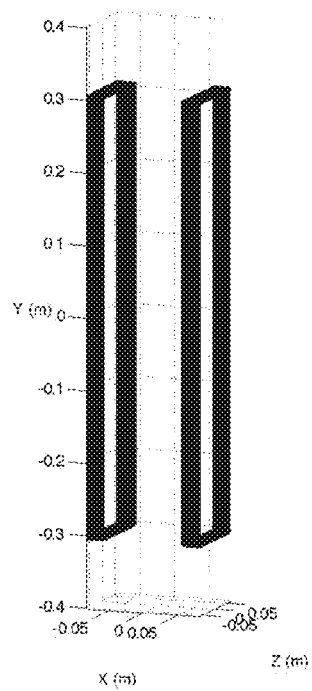
FIG. 53
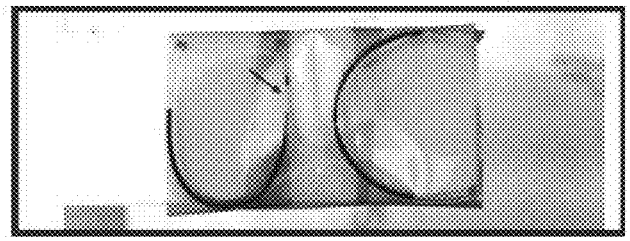
FIG. 54(top)
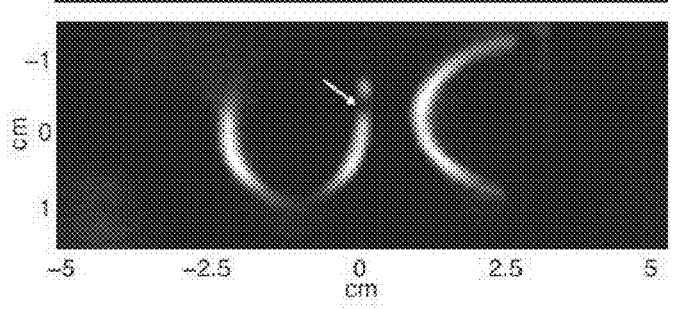
FIG. 54(bottom)

MAGNETIC PARTICLE IMAGING DEVICES AND METHODS

CROSS-REFERENCE TO RELATED APPLICATIONS

This patent application is a continuation of U.S. patent application Ser. No. 14/328,549, filed Jul. 10, 2014, which is a continuation of U.S. patent application Ser. No. 13/050,779, filed Mar. 17, 2011, now U.S. Pat. No. 8,884,617, which is a continuation-in-part of U.S. patent application Ser. No. 12/737,214, filed Dec. 16, 2010, which is a national stage application of PCT Application No. PCT/US2009/003764, filed Jun. 23, 2009, which claims priority to U.S. Provisional Patent Application No. 61/074,931, filed Jun. 23, 2008, the disclosures of each of which are hereby incorporated by reference in their entirety. U.S. patent application Ser. No. 13/050,779 also claims the benefit of priority under 35 U.S.C. §119(e) to U.S. Provisional Patent Application Nos. 61/340,542, filed Mar. 17, 2010, and 61/442,229, filed Feb. 12, 2011, the disclosures of each of which are hereby incorporated by reference in their entirety.

INTRODUCTION

Tomography is a technique of imaging by sections or sectioning, through the use of any kind of penetrating wave, such as radio-frequency waves, sound waves, x-rays, gamma rays, electron-positron annihilation waves, etc. Tomography can be used to produce two-dimensional cross-sectional image slices of a sample or subject in the tomographic device. These slices can be superimposed to form a three-dimensional image of the sample or subject. The data acquired by the tomographic device is analyzed by a mathematical procedure called tomographic reconstruction to produce the images. Tomographic reconstruction is typically performed using computers (e.g., computed tomography).

Magnetic particle imaging (MPI) is a tomographic or volumetric imaging technique that directly detects the magnetization from magnetic particles. The basic principle of MPI involves applying a magnetic field to magnetic particles in a selected region (e.g., magnetic particle contrast agents injected into the blood stream or labeled into or on cells) and detecting the magnetic fields generated by the magnetic particles. Similar to tomographic reconstruction, the data acquired from magnetic particle imaging can be processed using algorithms to produce images of the magnetic particles in the sample or subject. Similar to the tomographic imaging techniques discussed above, MPI has potential applications in medicine, such as in medical imaging, e.g., heart and blood vessel imaging, cell tracking, interventional radiology, and cancer detection. For example, a tracer or contrast agent that includes magnetic particles can be injected into a subject's blood stream and images can be acquired of blood vessels that carry the magnetic particle contrast agent.

SUMMARY

In accordance with the various embodiments of the present disclosure, there are provided devices, methods, and systems for magnetic particle imaging. Aspects of certain embodiments include a magnetic particle imaging device. The device includes a magnetic field source configured to produce a magnetic field having a non-saturating magnetic field region, an excitation signal source configured to produce an excitation signal in the non-saturating magnetic field region that produces a detectable signal from magnetic particles in the non-saturating magnetic field region, and a signal processor configured to convert a detected signal into an image of the magnetic particles. Aspects of the present disclosure also include methods of imaging magnetic particles in a sample, and methods of producing an image of magnetic particles in a subject. The subject devices and methods find use in a variety of applications, such as medical imaging applications.

Various embodiments of the present methods and systems will be described in detail with reference to the drawings, wherein like reference numerals represent like parts throughout the several views. Reference to various embodiments does not limit the scope of the claims attached hereto. Additionally, any examples set forth in this specification are not intended to be limiting and merely set forth some of the many possible embodiments for the claims.

Unless defined otherwise, all technical and scientific terms used herein have the same meaning as commonly understood by one of ordinary skill in the art. Although any methods, devices and material similar or equivalent to those described herein can be used in practice or testing, the methods, devices and materials are now described.

All publications and patent applications in this specification are indicative of the level of ordinary skill in the art and are incorporated herein by reference in their entireties.

It should be noted that two or more of the embodiments described herein, including those described above, may be combined to produce one or more additional embodiments which include the combined features of the individual embodiments. These and other aspects of the present disclosure will become more fully apparent from the following detailed description of the embodiments, the appended claims and the accompanying figures.

In this specification and the appended claims, the singular forms "a," "an," and "the" include plural reference, unless the context clearly dictates otherwise. Unless defined otherwise, all technical and scientific terms used herein have the same meaning as commonly understood to one of ordinary skill in the art.

BRIEF DESCRIPTION OF THE FIGURES

FIGS. 1A to 1C show schematic drawings of magnetic field sources, according to embodiments of the present disclosure.

FIG. 2A shows a cross-sectional illustration of a pair of magnetic field sources that produce a magnetic field gradient and a non-saturating magnetic field region in the form of a line, according to embodiments of the present disclosure. FIGS. 2B and 2C show illustrations of an MPI computed tomography technique using a non-saturating magnetic field region in the form of a line to acquire projected image slices at different angles, according to embodiments of the present disclosure.

FIG. 3C is a graph of received signal level versus frequency detailing intermodulation tones contained in a single peak of the signal envelope shown in FIG. 3C.

FIG. 10B is a perspective cut-away view of a magnetic subsystem of a device, according to embodiments of the present disclosure.

FIG. 29A shows a graph of a line scan down the bore, and FIG. 29B shows a graph of a line scan perpendicular to the imager bore, according to embodiments of the present disclosure.

FIG. 34 shows a photograph of x-Space MPI scanner, according to embodiments of the present disclosure. The free bore before addition of the transmit and receive coils was 8.4 cm.

FIG. 36A is a graph showing that the amplitude changed slowly as the sample was scanned 1.5 cm in y. FIG. 36B shows a graph of a time-slice near y=0 showing the raw signal as the sample was rapidly scanned 0.5 cm in z. Total scan time was 650 ms.

FIG. 37A shows a graph of experimental data showing 40 overlapped partial FOV scans of a 400 micron wide Resovist point source phantom without baseline correction, according to embodiments of the present disclosure. FIG. 37B shows a graph of experimental data with baseline correction, and FIG. 37C shows a graph of the assembled image that recovers the linearity across the full FOV, according to embodiments of the present disclosure.

FIG. 39A shows a graph of a line scan down the bore, and FIG. 39B shows a graph of a line scan perpendicular to the imager bore, according to embodiments of the present disclosure.

FIG. 49A shows a photographic image of a resolution phantom composed of polyethylene tubing (ID=400 µm) filled with undiluted Resovist tracer, according to embodiments of the present disclosure, and FIG. 49B shows graphs of baseline corrected, unassembled data for a wide bandwidth and a narrow bandwidth.

FIG. 53 shows a schematic of the position of two permanent magnets in a magnetic particle imaging device configured to produce a non-saturating magnetic field line, according to embodiments of the present disclosure.

FIG. 54 (top) shows a photograph of a "UC" phantom image built using tubing filled with undiluted tracer and encapsulated, according to embodiments of the present disclosure. FIG. 54 (bottom) shows an intrinsic MPI image of the "UC" phantom image showing correspondence to the phantom image, where the phantom image was obtained using a magnetic particle imaging device configured to produce a non-saturating magnetic field line, according to embodiments of the present disclosure. The total imaging time was 12 seconds, not including robot movement.

Figure 3A:
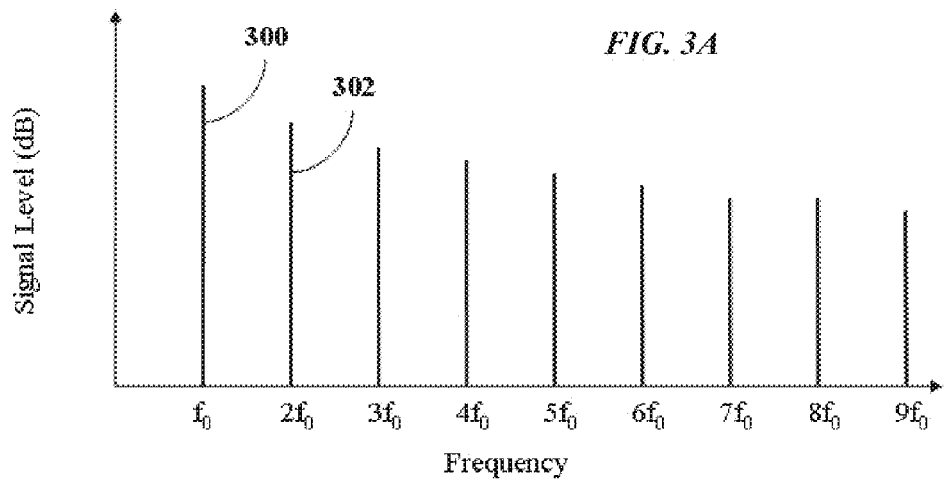
FIG. 3A is a graph of a received signal level versus frequency for a conventional MPI technique showing multiple received harmonics.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the methods and/or materials in connection with which the publications are cited.

DETAILED DESCRIPTION

Magnetic Particle Imaging Devices

As described in further detail below, in accordance with the various embodiments of the present disclosure, there are provided devices, methods, and systems for magnetic particle imaging (MPI). Aspects of certain embodiments include a magnetic particle imaging device. The magnetic particle imaging device may produce an image of magnetic particles in a sample.

Magnetic Field Source

The magnetic particle imaging device may include a magnetic field source. The magnetic field source may be of sufficient strength to saturate magnetic particles present in the magnetic field produced by the magnetic field source. Stated another way, the magnetic field source may produce a saturating magnetic field, where the saturating magnetic field has a sufficient magnetic field strength to saturate magnetic particles present in the saturating magnetic field. By "saturate" or "saturation" is meant that the magnetic particles have a magnetization such that an increase in the applied external magnetizing field will not significantly increase the magnetization of the magnetic particles further. In some instances, a magnetic particle includes a plurality of magnetic domains, each with a corresponding magnetic field. Application of an external magnetic field source to the magnetic particles may cause the magnetic fields of the magnetic domains to align parallel to the applied external magnetic field. In some instances, the applied external magnetic field is of sufficient strength to "saturate" the magnetic particle, such that substantially all of the magnetic domains in the magnetic particle are aligned parallel to the applied external magnetic field, so further increases in the applied external magnetic field will not substantially cause further alignment of the magnetic domains.

In certain embodiments, the magnetic field source is configured to produce a magnetic field having a non-saturating magnetic field region. The non-saturating magnetic field region may be positioned within a portion of the magnetic field. By "non-saturating" is meant that the applied magnetic field in that region has a strength below that necessary to saturate the magnetic particles in the non-saturating magnetic field region. In certain embodiments, the non-saturating magnetic field region has a magnetic field strength of substantially zero. The non-saturating magnetic field region may also be referred to as a "field-free region" or "FFR". The non-saturating magnetic field region may be configured as a point, a line, a plane, or a 3-dimensional region. In some instances, the non-saturating magnetic field region is a line. In these cases, the non-saturating magnetic field line may be perpendicular to the axis of the magnetic field. In some instances, the non-saturating magnetic field line is substantially parallel to the axis of the magnetic field. In other embodiments, the non-saturating magnetic field region is a 3-dimensional region of space in the magnetic field.

In certain embodiments, the magnetic field source includes two or more magnetic field sources, such as 4 or more, or 6 or more, or 8 or more, or 10 or more magnetic field sources. The two or more magnetic field sources may be configured such that the two or more magnetic field sources have a combined magnetic field. In certain cases, the combined magnetic field is a saturating magnetic field. In some instances, the combined magnetic field includes a non-saturating magnetic field region, (e.g., a field-free region).

The magnetic field sources may be arranged in various orientations relative to each other. For example, the magnetic field sources may be arranged relative to each other such that the combined magnetic field produced by the magnets includes a non-saturating region in the magnetic field. The magnetic field sources may be square shaped, rectangular, circular, elliptical, spherical, ring-shaped, combinations thereof, and the like. In certain embodiments, the magnetic field sources are ring-shaped. In these embodiments, the magnetic field sources may be coaxially arranged, such that the center of each ring-shaped magnetic field source is on the same axis (e.g., the coaxial axis). In some instances, the coaxial axis passes through the center of each ring-shaped magnetic field source and is substantially perpendicular to each magnetic field source. In certain embodiments, the coaxial axis is labeled as the z-axis in a 3-dimensional coordinate system, and is perpendicular to the x and y axes, such that the x-axis is perpendicular to both the y and z axes, the y-axis is perpendicular to both the x and z axes, and the z-axis is perpendicular to both the x and y axes.

In some cases, the magnetic field sources are arranged around an imaging area of the device. The imaging area of the device may be configured to contain a sample that is to be imaged and, in some cases, is positioned between the magnetic field sources. For example, in embodiments where the magnetic field sources are ring-shaped magnetic field sources as described above, the coaxial axis of the magnetic field sources may be substantially parallel to a longitudinal axis of an imaging area of the device. The magnetic field sources may be positioned at opposing ends of the imaging area of the device. For instance, a first magnetic field source may be positioned at one end of the longitudinal axis of the imaging area of the device, and a second magnetic field source positioned at the opposite end of the longitudinal axis of the imaging area of the device.

In other embodiments, the magnetic field sources are arranged on the sides of the imaging area of the device (rather than at each end of the imaging area of the device). For instance, a first magnetic field source may be positioned on one side of the imaging area of the device, such as along a side of the imaging area substantially parallel to a longitudinal axis of the imaging area of the device. A second magnetic field source may be positioned on an opposing side from the first magnetic field source, such as along a side of the imaging area of the device opposite the first magnetic field source and substantially parallel to the longitudinal axis of the imaging area of the device.

The magnetic field source may include permanent magnets, electromagnets, superconducting magnets, high-mu materials (e.g., iron), combinations thereof, and the like. In certain embodiments, the magnetic field source includes one or more permanent magnets. By "permanent magnet" is meant a magnetic material has a persistent magnetic field such that the magnetic field that does not substantially decrease over time. In contrast, the term "soft magnet" refers to a material that can be magnetized in the presence of an applied external magnetic field, but whose magnetism substantially decreases when the external magnetic field is removed. In some instances, the magnetic field source includes two or more permanent magnets. The permanent magnets may be of any desirable shape, and in some instances may be ring-shaped permanent magnets as described above. The ring-shaped permanent magnets may be coaxially arranged relative to each other.

The magnetic field source may be a permanent magnet, such as a rare-earth magnet. Rare-earth magnets include, but are not limited to, samarium-cobalt magnets (e.g., $SmCo_5$), neodymium alloy (NdFeB) magnets (e.g., $Nd_2Fe_{14}B$), and the like.

In certain embodiments, the magnetic field source produces a magnetic field ranging from 0.01 mT to 25 T, or from 0.01 mT to 10 T, or from 0.01 mT to 5 T, or from 0.01 mT to 3 T, or from 0.01 mT to 1 T, such as from 0.1 mT to 500 mT, including from 1 mT to 100 mT, for example, from 1 mT to 30 mT, or from 10 mT to 20 mT. In certain cases, the magnetic field sources produce an inhomogeneous magnetic field. By "inhomogeneous" is meant that the magnetic field is different depending on the position within the magnetic field. For instance, the magnetic field may have a magnetic field gradient that is greater at one position in the magnetic field and gradually decreases towards a second position in the magnetic field. In some cases, the magnetic field sources are configured to produce a magnetic field with a magnetic field gradient ranging from 0.1 T/m to 250 T/m, such as from 0.1 T/m to 100 T/m, or from 0.1 T/m to 75 T/m, or from 0.1 T/m to 50 T/m, such as from 0.5 T/m to 40 T/m, including from 0.5 T/m to 30 T/m, or from 1 T/m to 30 T/m, for example from 1 T/m to 20 T/m, or from 1 T/m to 10 T/m, or from 1 T/m to 7 T/m, or from 2.5 T/m to 7 T/m. In certain instances, the magnetic field sources produce a magnetic field with the same magnetic field gradient along the coaxial axis as along an axis transverse to the coaxial axis. In some cases, the magnetic field sources produce a magnetic field with a different magnetic field gradient along the coaxial axis from the magnetic field gradient along an axis transverse to the coaxial axis. For example, the magnetic field gradient along the coaxial axis may be 1.2 times greater, or 1.4 times greater, or 1.6 times greater, or 1.8 times greater, or 2 times greater, or 3 times greater, or 4 times greater, or 5 times greater than the magnetic field gradient along an axis transverse to the coaxial axis.

Various designs and configurations of magnetic field sources may be used in various embodiments. Examples of magnetic field sources are illustrated in FIGS. 1A, 1B, 1C. A front entry design using ring magnets 100, 102 is shown in FIG. 1A. Also shown are cut-away views where the magnetic field sources are permanent magnets 104, or electromagnets 106. A side entry design using circular plate magnets 110, 112 is shown in FIG. 1B. Also shown are cut-away views where the magnetic field sources are disc-shaped permanent magnets 114, or electromagnets 116. FIG. 1C shows a front entry design using a pair of Halbach arrays 120, 122.

FIG. 2A is a cross-sectional illustration of a pair of magnetic field sources 200 and 202 that produce a strong field gradient and a field-free region 204. The magnetic field sources can be a permanent magnet arrangement having a three dimensional structure that can be machined from a single block of permanent magnet. In some cases, the permanent magnets are designed using an $L^1$-norm optimization method. In some embodiments, the magnetic field sources are designed so that there is an axial entry and the field free region has a longitudinal axis perpendicular to the axis of the magnetic field. The magnet or the sample being imaged can be rotated mechanically.

Excitation Signal Source

Aspects of embodiments of the magnetic particle imaging device include an excitation signal source configured to produce an excitation signal in the non-saturating magnetic field region. In some cases, the excitation signal source is configured to produce an excitation signal in the non-saturating magnetic field region sufficient to produce a detectable signal from magnetic particles in the non-saturating magnetic field region. For example, the excitation signal source may be configured to apply the excitation signal to magnetic particles in the non-saturating magnetic field region. In some instances, application of the excitation signal to the magnetic particle in the non-saturating magnetic field region produces a detectable signal from the magnetic particles in the non-saturating magnetic field region.

The excitation signal source may include a radio frequency (RF) excitation signal source that produces an RF excitation signal. The RF excitation signal source may produce a magnetic field, which in some instances is an oscillating magnetic field. The RF excitation signal source may be configured to produce a magnetic field ranging from 0.1 mT to 5 T peak to peak, or from 0.1 mT to 3 T peak to peak, or from 0.1 mT to 1 T peak to peak, or from 0.1 mT to 500 mT peak to peak, or from 0.1 mT to 250 mT peak to peak, or from 1 mT to 100 mT peak to peak, or from 1 mT to 50 mT peak to peak, such as from 10 mT to 50 mT peak to peak, including from 20 mT to 40 mT peak to peak. In some cases, the RF excitation signal source is configured to produce a magnetic field of 30 mT peak to peak. In certain embodiments, the RF excitation signal source produces an oscillating magnetic field having a frequency ranging from 0.1 Hz to 1000 MHz, or from 1 Hz to 500 MHz, or from 1 kHz to 250 MHz, or from 1 kHz to 100 MHz, or from 1 kHz to 50 MHz, or from 1 kHz to 25 MHz, or from 1 kHz to 10 MHz, such as from 10 kHz to 10 MHz, including from 10 kHz to 1 MHz, for example from 10 kHz to 500 kHz, or from 10 kHz to 100 kHz. In some instances, the RF excitation signal source produces an oscillating magnetic field having a frequency of 20 kHz.

The RF excitation signal may be a periodic oscillating field, such as a sinusoidal waveform. However, in some instances, the waveform of the RF excitation signal is not sinusoidal. In some cases, a non-sinusoidal waveform may facilitate an increase in harmonic content, improving the signal to noise ratio (SNR) and resolution. For example, certain embodiments of the RF excitation signal may include a triangle waveform. The waveform may also be dynamically changed during operation to provide different imaging properties.

The excitation signal source may include an intermodulation excitation signal source that produces an intermodulation excitation signal. The intermodulation excitation signal source may produce a magnetic field, which in some instances is an oscillating magnetic field. The intermodulation excitation signal source may be configured to produce a magnetic field ranging from 0.1 mT to 1 T peak to peak, or from 0.1 mT to 500 mT peak to peak, or from 0.1 mT to 250 mT peak to peak, or from 1 mT to 100 mT peak to peak, or from 1 mT to 75 mT peak to peak, 1 mT to 50 mT peak to peak, such as from 1 mT to 40 mT peak to peak, including from 1 mT to 30 mT peak to peak, or from 1 mT to 20 mT peak to peak, or from 1 mT to 10 mT peak to peak. In some cases, the intermodulation excitation signal source is configured to produce a magnetic field of 6 mT peak to peak. In certain embodiments, the intermodulation excitation signal source is a low frequency (LF) intermodulation excitation signal source that produces an oscillating magnetic field having a frequency ranging from 1 Hz to 1 MHz, or from 1 Hz to 500 kHz, or from 1 Hz to 250 kHz, or from 1 Hz to 100 kHz, or from 1 Hz to 50 kHz, or from 1 Hz to 20 kHz, such as from 1 Hz to 10 kHz, including from 1 Hz to 5 kHz, for example from 1 Hz to 1 kHz, or from 1 Hz to 500 Hz. In some instances, the intermodulation excitation signal source produces an oscillating magnetic field having a frequency of 1 kHz. In certain embodiments, the RF excitation signal has a frequency that is greater than the frequency of the intermodulation excitation signal. For example, the RF excitation signal may have a frequency that is 5 to 1,000,000 times greater than the frequency of the intermodulation excitation signal, such as 50 to 100,000 times greater, including 100 to 10,000 times greater, or 100 to 5,000 times greater, or 100 to 500 times greater than the frequency of the intermodulation excitation signal.

Intermodulation Theory

When magnetic field strengths used in MPI are less that 1 Tesla, tissue is unaffected by the magnetic field, but a super-paramagnetic iron oxide (SPIO) particle undergoes a nonlinear change in magnetization described by the Langevin theory of paramagnetism. Specifically, the magnetization M is given by:

$$M = M_0 L\left[\frac{mH}{k_B T}\right] = M_0\left(\coth\frac{mH}{k_B T} - \frac{k_B T}{mH}\right)$$

where L is the Langevin function, m is the magnetic moment of the particle, H is the applied magnetic field, $k_B$ is Boltzmann's constant, and T is the absolute temperature.

To excite the particles, in some embodiments a single oscillating magnetic field of magnitude $H_0$ and frequency $f_0$ is generated within the region where the particles are located. In the case of a sinusoidal excitation waveform, the oscillating field is given by $H(t)=H_0 \sin(2\pi f_0 t)$.

The field H(t) excites the particles and induces a corresponding time-varying magnetization at harmonics of $f_0$ $$M(t) = \sum_{m \geq 1} A_m \exp(2\pi i m f_0 t),$$

where $A_m$ are the amplitudes of the various harmonics and the index m ranges over the detected harmonics. See FIG. 3A.

In some embodiments using intermodulation, a second oscillating magnetic field of magnitude $H_1$ and frequency $f_1$ is also generated within the region where the particles are located. Thus, in the case of a sinusoidal excitation waveform aligned in parallel with the first excitation field, the net oscillating field is given by $H(t)=H_0 \sin(2\pi f_0 t)+H_1 \sin(2\pi f_1 t)$.

This intermodulation field H(t) excites the particles the nonlinear Langevin function acts as a nonlinear mixer, inducing a corresponding time-varying magnetization $$M(t) = \sum_{m \geq 1} \sum_{n} A_{m,n} \exp(2\pi i (m f_0 + n f_1) t).$$

where $A_{m,n}$, are the amplitudes of the separate intermodulation tones. In addition to the harmonics, there are sideband tones corresponding to sum and difference frequencies. See FIGS. 3B and 3C. The index m may be limited to a finite number of detected harmonics and the index n may be limited by the finite number of detected sideband intermodulation tones around each harmonic. The intermodulation spectrum shows the quantity of magnetic particles at the field-free point. Thus, instead of detecting a sequence of harmonics across a broad bandwidth, it is possible to obtain sufficient information by detecting the intermodulation signals across a relatively narrow bandwidth in close proximity to a single harmonic. Detecting intermodulation signals around additional harmonics provides additional information. For example, intermodulation sidebands may be detected around both second and third harmonics to produce a set of intermodulation images.

The frequencies $f_0$ and $f_1$ and the field strengths $H_0$ and $H_1$ can all be selected independently of each other. In some cases, the specific absorption rate (SAR) and received signal strength depend on $f_0$ and $H_0$ since $f_0 \gg f_1$ and SAR increases as $H^2 f^2$. Imaging speed and detection bandwidth may depend on $f_1$ to allow detection at each field-free point of intermodulation sidebands surrounding harmonics $mf_0$. Thus, the scanning speed may be selected so that the sidebands can be detected at each point without aliasing. In some cases, increasing $f_1$ may facilitate an increase in imaging speed. In certain instances, $f_1$ is not increased to a value such that the received signal bandwidth is greater than the bandwidth of the receiver coil. SNR and the spatial extent of the point spread function (PSF) may depend on the total magnitude of the excitation fields $H_{tot} = H_0 + H_1$. In some cases, increasing $H_{tot}$ increases the total signal received while also widening the PSF. Increasing $H_1$ may increase the received signal while not substantially affecting SAR. In some instances, increasing $H_1$ facilitates an increase in signal while decreasing resolution, and vice versa.

LF Intermodulation

In various embodiments, the LF (low frequency) intermodulation source may include one or more electromagnets, such as water-cooled electromagnets. MRI gradient amplifiers may be used to drive the magnets. In certain embodiments, the LF intermodulation provides a large shift in magnetization of the magnetic particles in the non-saturating magnetic field region while not substantially increasing the specific absorption rate (SAR). LF intermodulation may also facilitate applying magnetic energy to the sample which is then up-mixed with the RF frequency. An RF eddy current shield may be used prevent interaction between the LF circuits and the RF transmit coil. In addition, a set of filters, such as common mode and differential low-pass filters, may also be positioned between the power amplifier and coil to reduce interaction. The gradient amplifiers may be current controlled and eddy current compensated.

The intermodulation excitation field may be applied in the x, y, z directions or any subset thereof. Changing the direction the intermodulation excitation source may change the shape and magnitude of the point spread function.

In certain instances, the LF intermodulation excitation signal and the scanning magnetic field (described in more detail below) may both be generated by the same magnetic field source (e.g., electromagnets). In other embodiments, separate magnetic field sources (e.g., electromagnets) are used to generate the LF intermodulation excitation signal and the scanning magnetic field. Having a separate LF intermodulation excitation signal source and a separate scanning magnetic field source may facilitate applying an LF intermodulation excitation signal that has a different magnetic field strength and/or magnetic field gradient from the scanning magnetic field.

Scanning Magnetic Field Source

Aspects of the magnetic particle imaging device include a scanning magnetic field source configured to produce a scanning magnetic field. In some cases, the scanning magnetic field is configured to position the non-saturating magnetic field region in the magnetic field. The scanning magnetic field may be applied to the magnetic field causing the non-saturating magnetic field region of the magnetic field to be displaced from its initial position in the magnetic field. Alternatively, or in addition to the scanning magnetic field source, the non-saturating magnetic field region may be scanned through the sample by moving the sample relative to the magnetic field. For example, the device may include a sample holder that may be displaced in one or more directions relative to the magnetic field sources.

The scanning magnetic field source may be configured to cause the non-saturating magnetic field region to scan through the sample in the device in one or more directions. Movement of the non-saturating magnetic field region relative to the sample may be performed in one, two, or three dimensions, and may be implemented by mechanical movement of the sample relative to the magnetic field source and/or by electronically modifying the magnetic field (e.g., the inhomogeneous gradient field) using a scanning magnetic field source (e.g., scanning electromagnets) that generate a homogeneous field. The scanning magnetic field can be applied in x, y, and z directions, or a subset of these directions. For example, the scanning magnetic field source (e.g., scanning electromagnets) may be configured to position the non-saturating magnetic field region within a plane, while mechanical movement of the sample provides translation along an axial direction perpendicular to the plane.

Figure 4:
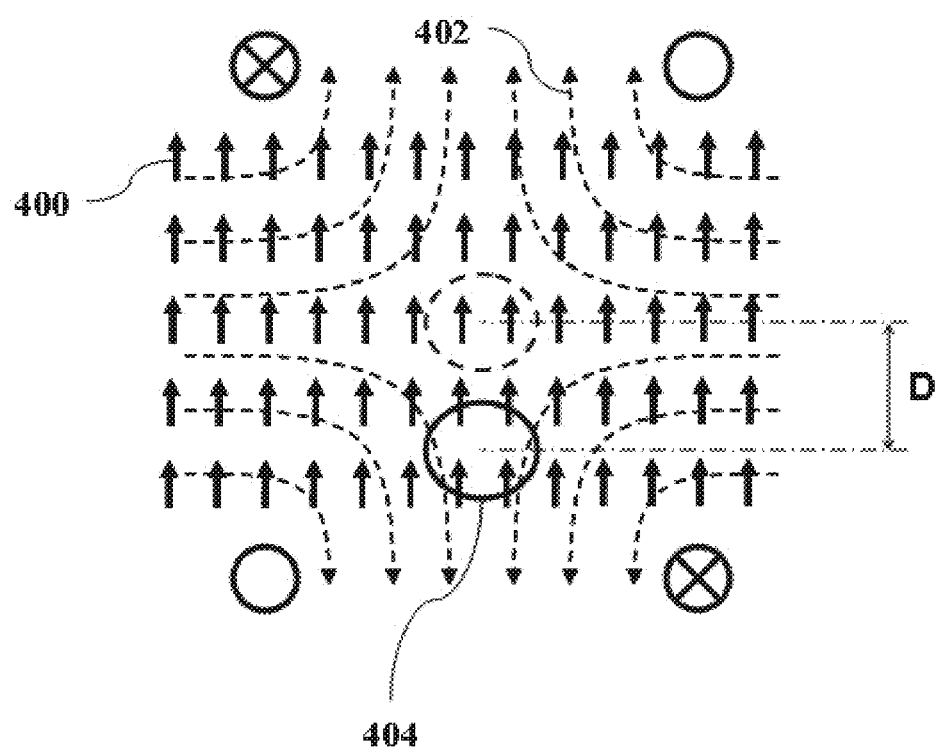
FIG. 4 illustrates the use of a homogeneous field superimposed on an inhomogeneous gradient field to shift the position of the field-free point, according to embodiments of the present disclosure.

The scanning magnetic field may be a homogeneous field. In some cases, the scanning magnetic field source includes one or more electromagnets, such as but not limited to Helmholtz coils. The homogeneous field 400 superimposed on the inhomogeneous gradient field 402 has the effect of shifting the position of the non-saturating magnetic field region 404 by a distance D, as illustrated in FIG. 4. A switching amplifier such as an H-bridge may be used to reverse the direction of the homogeneous scanning magnetic field to provide displacement of the non-saturating magnetic field region in opposite directions along a given axis. In some embodiments, the LF intermodulation excitation source is the same as the scanning magnetic field source. In other embodiments, the LF intermodulation excitation source is different from the scanning magnetic field source.

Figure 5:
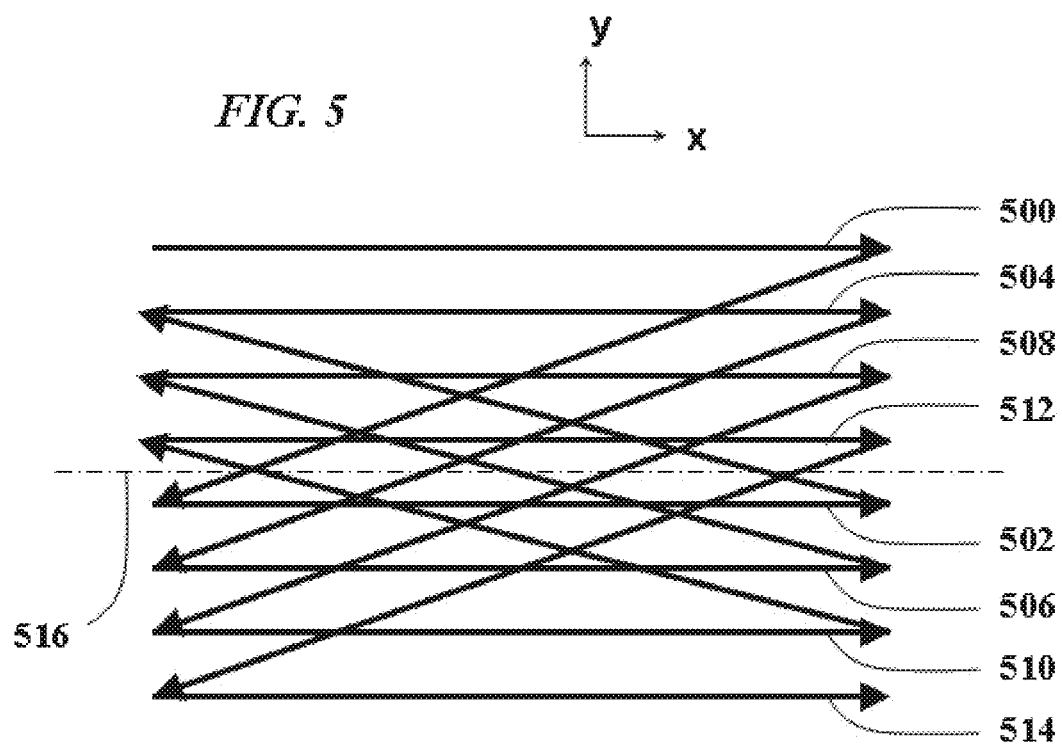
FIG. 5 illustrates an example of a power-efficient scanning trajectory, according to embodiments of the present disclosure.

Due to the large field gradients, strong homogeneous fields may be required to shift the field-free point a distance to provide electronic scanning of the sample. Consequently, scanning a large field of view can require large amounts of power and large amplifiers. Accordingly, certain embodiments provide methods of scanning that reduce heat loading of the power amplifiers, allowing the use of smaller and less expensive power electronics. For example, FIG. 5 illustrates an example of a power-efficient scanning trajectory in the x-y plane according to embodiments of the present disclosure. The scan begins with a left-to-right scan line 500 along the x-axis. Line 500 is displaced a relatively large distance in the y-direction from center line 516. Center line 516 is the line along which the field-free region is positioned when there is no displacement field in the y-direction. Horizontal scan line 500 is followed by a diagonal scan line down and to the left to the start of horizontal scan line 502 which is displaced a relatively small distance in the y-direction from center line 516, and thus requires a less powerful field than is required to displace scan line 500 from center line 516. Horizontal scan line 502 is followed by a diagonal scan up and to the left to the start of horizontal scan line 504, which is displaced slightly less from center line 516 than scan line 500. Next is scan line 506, which is displaced a slightly greater distance from the center line 516 than scan line 502. The scan then continues in this way, alternating between scan lines above and below center line 516. The consecutive scan lines above and below the center line 516 are separated by approximately the same distance due to the progressive decrease in displacement of y-displacement of scan lines above the center line 516 and progressive increase of y-displacement of scan lines below the center line 516. Consequently, as power demands for scan lines displaced in one direction decrease, power demands in scan lines displaced in the other direction increase, resulting in an approximately constant average power demand. This constant average power correlates to the uniform distance between consecutive scan line pairs, i.e., the displacement between lines 500 and 502 is the same as the displacement between lines 504 and 506, between lines 508 and 510, and between lines 512 and 514. Switching between displacements above and below the center line 516 may allow circuits used for displacements in one direction to cool during a scan displaced in the opposite direction. Depending on the application and operational parameters of a given scan, the scan time for each line may range from 0.5 ms to 10 sec, such as from 1 ms to 5 s, including from 1 ms to 1 s, for example from 1 ms to 0.5 s. Because the horizontal scan lines all scan in the same direction, e.g., from left to right, this may facilitate simpler signal processing.

Other scanning trajectories are also possible and may be used depending on the specific application or scanning requirements. For example, to reduce transition time from scan line to scan line, instead of moving to the next scan line diagonally, in some cases only the y-displacement is changed when moving to the next scan line. The amplifiers may have slew rate limits, and only changing the y-displacement when moving from one scan line to the next scan line may reduce the slew rate requirements in the x-direction. For example, if heating is not a significant issue then a more time-efficient scan may be used, such as a serpentine scan of horizontal lines sequentially progressing from a largest upward displacement in the y-direction to a largest downward displacement in the y-direction. In some instances, a spiral scan may be performed, starting from the center and spiraling outward. The spiral scan may facilitate scanning a sample region with a greater amount of overlap between scans than a rectangular scanning pattern.

In certain embodiments, the scanning magnetic field source translates the position of the non-saturating magnetic field region in real time to provide scanning. The magnetic particle imaging device may be configured to provide for data acquisition and magnetic particle detection in real time as the scanning magnetic field positions the non-saturating magnetic field region through the sample. In some embodiments, a pair of electromagnet coils is used to provide independent translation in each of three orthogonal directions. The scanning magnetic field source may have a power of 0.1 kW to 1 MW, or from 0.1 kW to 500 kW, or from 0.1 kW to 250 kW, or from 0.1 kW to 100 kW, such as 1 kW to 50 kW, including 1 kW to 10 kW. In some instances, the scanning magnetic field source has a power of 5 kW. In certain cases, the scanning magnetic field sources are configured to move the non-saturating magnetic field region from 0.1 cm to 100 cm, such as from 0.1 cm to 50 cm, including from 0.1 cm to 25 cm, or from 0.1 cm to 10 cm, or from 0.1 cm to 5 cm from the initial position of the non-saturating magnetic field region. In some instances, the scanning magnetic field sources are configured to produce a scanning magnetic field with a homogeneity of 10% or less, such as 5% or less, including 3% or less, for example 1% or less.

Other systems associated with the excitation signal sources may be included in the device. For example, to provide cooling, the excitation signal sources may be configured as electromagnetic coils. In some embodiments, the electromagnetic coils are configured to be cooled by contacting the coils with a coolant. For instance, the coils may be made of hollow copper tubing through which coolant (e.g., water) may be circulated. In some instances, the coolant may be circulated at a rate to provide sufficient cooling capacity for the excitation coils. For instance, the coolant (e.g., water) may be circulated at 6 gpm and 30 psi, which in some instances provides 34 kW cooling capacity. Other aspects of the excitation signal source may include a shield, such as an RF shield. The RF shield may be configured to absorb signals that are not involved in the excitation of the magnetic particles and/or the signal generated by the magnetic particles. In some instances, the RF shield is configured to be cooled using circulating coolant (e.g., water).

Receiver

Aspects of the magnetic particle imaging device include a receiver. The receiver may be configured to detect the signals from the magnetic particles in the non-saturating magnetic field region. For example, after applying an excitation signal to the magnetic particle in the non-saturating magnetic field region, as described above, the magnetic particles may produce a detectable signal, which may be detected by one or more receivers. The receivers may be any type of receiver that is capable of receiving the detectable signals from the magnetic particles. For example, the receiver may be configured to detect magnetic signals from the magnetic particles and convert the detected magnetic signals into an electrical signal.

In some embodiments, the receiver includes a receiver coil. In some cases, the receiver is configured to be a narrowband receiver. For example, the receiver may have a quality factor (e.g., Q-factor) of 1 or more, such as 10 or more, including 50 or more, or 100 or more, for instance 150 or more, or 200 or more, or 500 or more, or 1000 or more. The Q-factor is a dimensionless parameter that characterizes the bandwidth of the receiver relative to the center frequency of the receiver. A receiver with a high Q-factor (e.g., 100 or more) may facilitate an increase in the signal to noise ratio (SNR) by reducing the bandwidth requirements of the receiver. For instance, in some cases, the receiver is configured to have a receive bandwidth ranging from 1 kHz to 100 MHz, such as from 1 kHz to 50 MHz, including from 5 kHz to 25 MHz, or from 10 kHz to 10 MHz, or from 10 kHz to 5 MHz, or from 10 kHz to 1 MHz, or from 20 kHz to 500 kHz, or from 20 kHz to 200 kHz.

In certain embodiments, the receiver includes a receive coil configured as a gradiometer. The gradiometer include a Litz wire and an overall Q-factor of 100 or more, or 150 or more (e.g., $Q_{coil}=167$). In some cases, the receiver coil includes an inner coil and an outer coil. The inner coil may have a diameter less than the diameter of the outer coil. For instance, the inner coil may have a diameter ranging from 1 cm to 1 m, such as from 1 cm to 500 cm, or from 1 cm to 250 cm, or from 1 cm to 100 cm, or from 1 cm to 50 cm, or from 1 cm to 25 cm, or from 1 cm to 10 cm. The outer coil may have a diameter greater than the diameter of the inner coil, and may range from 1 cm to 1 m, such as from 1 cm to 500 cm, or from 1 cm to 250 cm, or from 1 cm to 100 cm, or from 1 cm to 50 cm, or from 1 cm to 25 cm, or from 1 cm to 10 cm. For example, the inner coil may have a diameter of 3.175 cm and the outer coil may have a diameter of 4.5 cm.

The receiver may include additional electronics associated with the receiver coil, such as, but not limited to, a phase coherent control console and detector. The coherent detector may be configured to directly sample at 65 MSPS and digitally down convert the RF signal to baseband. The down-sampled signal may have a bandwidth of 31.25 kSPS centered at $2f_0=300$ kHz with over 90 dB of dynamic range, where $f_0$ is the excitation frequency. An object containing a distribution of magnetic particles may be translated through the bore using a linear translator controlled by the control console. The detected signal may be continuously acquired during translation of the stage in the readout direction, e.g., along the axis of the bore. The signal received by the receiver coil may be transmitted to the preamplifier and then into the control console. The digitized signal may be quadrature demodulated at multiples of the intermodulation frequency (i.e., $\pm f_1$, $\pm 2f_1$, $\pm 3f_1$, $\pm 4f_1$, etc.) and brick-wall filtered at 20 Hz, where $f_1$ is the intermodulation frequency. In some instances, the intermodulation products around the fundamental frequency may be more difficult to receive than those around the harmonics due to eddy-current coupling from the excitation frequency into the receive coil. The intermodulation products around the fundamental frequency may be detected by subtracting the fundamental frequency using a low phase noise PLL or crystal filter.

In certain cases, the received signal contains most of the power in the lower harmonics and lower intermodulation peaks while most of the high frequency spatial content is in the higher harmonics and higher intermodulation peaks (where "higher" means n or m is greater than 4 and "lower" means n or m is 4 or less). The magnitude of the harmonics may depend on the size of the magnetic particles, where larger particles increase higher order harmonics. Intermodulation may increases the spectral content of the received signal. In some cases, the total normalized signal is larger with intermodulation than without. In certain cases, the intermodulated point-spread function (PSF) around $2f_0$ is similar to the PSF without intermodulation. As the harmonic number (n) increases, the magnitude of the PSF decreases and the resolution increases.

While in some embodiments the intermodulation products around a single harmonic (e.g., $2f_0 \pm nf_1$) may be received, in other embodiments the RF coils may be configured to receive multiple frequencies around multiple harmonics (e.g., $2f_0 \pm nf_1$, $3f_0 \pm nf_1$, $4f_0 \pm nf_1$, $5f_0 \pm nf_1$). For example, one or more dual-tuned coils may be used, each configured to receive signals around two harmonics. Alternatively, multiple RF coils may be separately tuned to receive the signals around each harmonic.

As the excitation frequency $f_0$ increases, the frequency separation of the harmonics of the excitation frequency increases. In some instances, increasing the excitation frequency may facilitate coil-to-coil isolation, high-Q coil construction, and noiseless rejection of the fundamental. As $f_0$ increases, the SAR limit may be approached. For example, with $f_0=1$ MHz and detection at $2f_0=2$ MHz, a SAR of 4 W/kg may be reached at 3 $mT_{peak-peak}$ in a small animal.

In certain embodiments, a high-Q receive coil may facilitate a simplification in construction and optimal noise matching of the receiver system. The bandwidth requirements may be less due to the low intermodulation frequency (e.g., $f_1=200$ Hz) as compared to the excitation frequency. Typically, detecting N harmonics with a conventional MPI would require a bandwidth of $BW=Nf_0$. Thus, detecting N=8 harmonics using an excitation frequency $f_0=150$ kHz would require a bandwidth of 1.2 MHz, which may result in sub-optimal matching to the preamplifier. In contrast, with intermodulation, the bandwidth may depend on the intermodulation frequency (e.g., $f_1=200$ Hz) instead of the excitation frequency (e.g., $f_0=150$ kHz). In these cases, the receive bandwidth may be less than a typical MPI system.

Figure 6A:
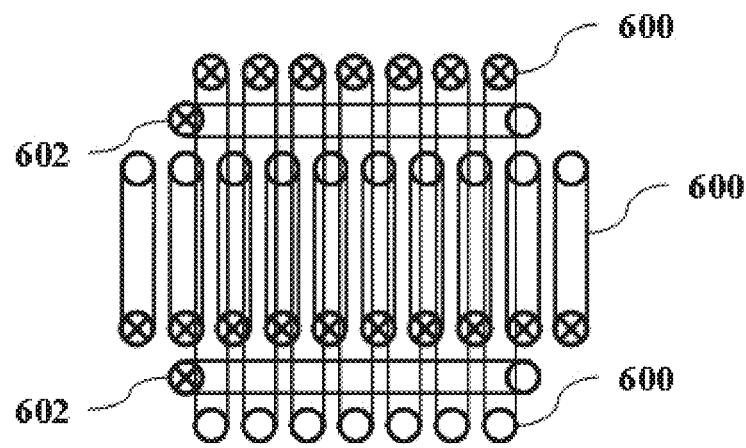
FIGS. 6A and 6B illustrate separate x, y, z receiver coils used to measure signals in orthogonal x, y, z directions according to an embodiment of the invention.
Figure 6B:
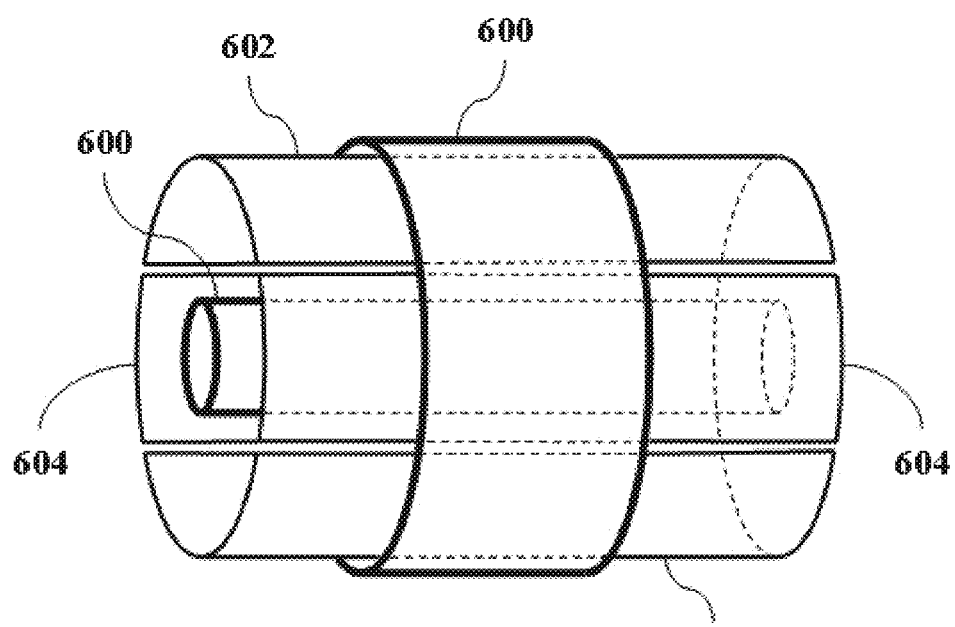

The receiver coils may be configured to convert the detected magnetic signal from the sample into an electrical signal. In some embodiments, separate x, y, z receiver coils are used to measure signals in orthogonal x, y, z directions, as illustrated in FIGS. 6A and 6B. The cross-sectional view of FIG. 6A shows the z coil 600 and y coil 602. The perspective view of FIG. 6B also shows the z coil 600, y coil 602, and the x coil 604. The z coil has zero net area and is wound as a gradiometer. The zero net area provides reduced feed through of the fundamental frequency $f_0$. If transverse RF transmit coils are used, the transverse receive coils can be geometrically decoupled by placing them such that less net area occurs between them. The receive coils may be wound so that they produce a homogeneous magnetic field. In some cases, the transverse receive coils are similarly wound with a gradiometer configuration.

Figure 7A:
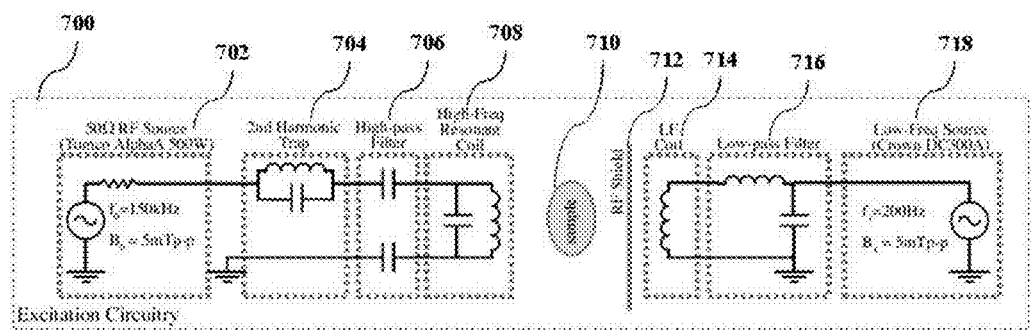
FIGS. 7A and 7B are schematic diagrams of the transmit and receive circuit chains, respectively, according to embodiments of the present disclosure.
Figure 7B:
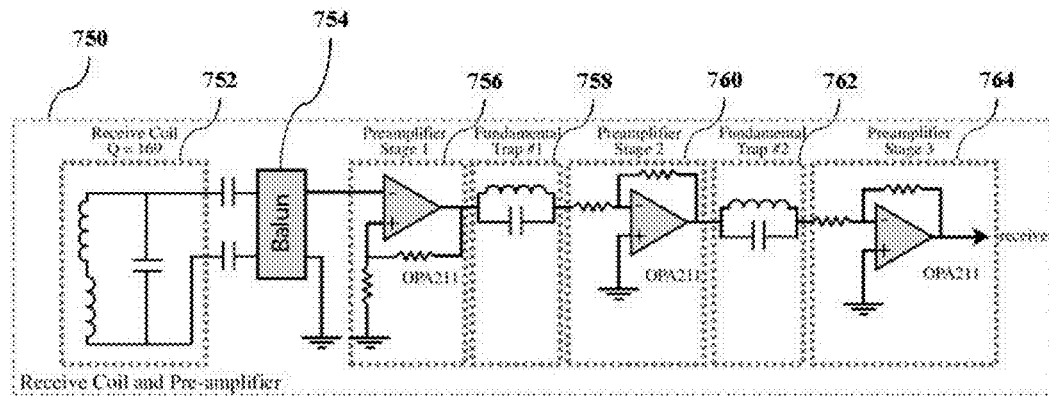
Figure 7C:
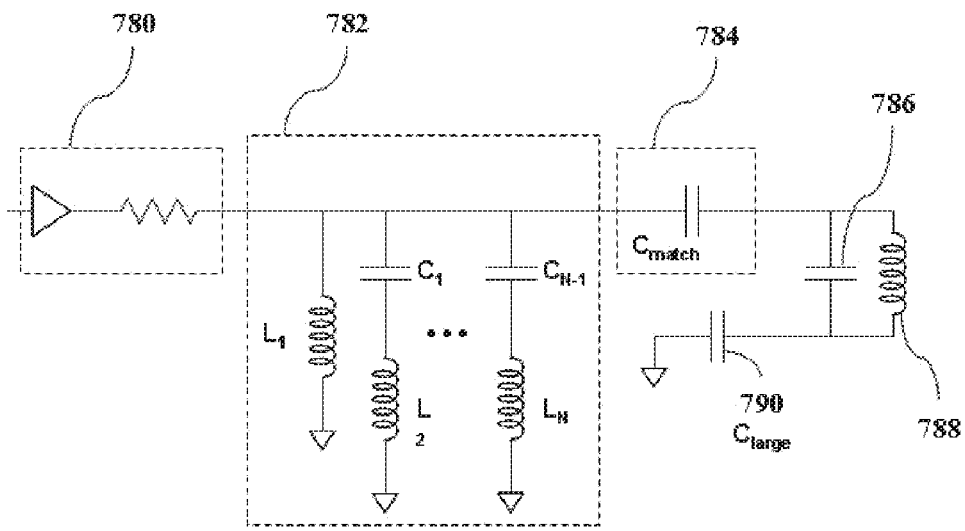
FIG. 7C is a schematic diagram of the transmit circuit chain, according to embodiments of the present disclosure.
Figure 7D:
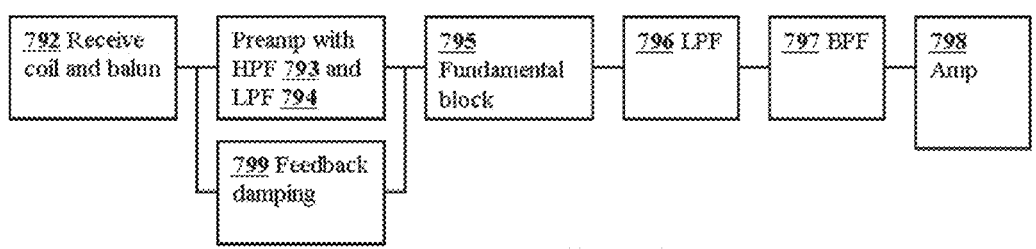
FIG. 7D is a block diagram of a receive circuit chain, according to embodiments of the present disclosure.

FIG. 7D is a block diagram of a receive circuit chain according to an embodiment of the present disclosure. Three receive circuits may be used, one for each of the x, y, and z directions. Each receive circuit may include a high-Q receive coil and balus 792, low amplification and low noise HPF preamplifier 793 and 794, fundamental block 795, low-pass filter 796, band-pass filter 797, LPF amplifier 798, and feedback circuit 799. Band-pass filter 797 may be centered around a harmonic such as $2f_0$, but may also be centered around another higher harmonic or so that multiple harmonics are allowed to pass. The receive circuit may be constructed to remove the fundamental signal $f_0$ and only pass harmonics $mf_0$, m>1. The circuits shown herein are illustrative examples and various alternative circuits may be designed to perform equivalent functions.

In some cases, the preamplifier includes operational amplifiers and high-Q tuned traps. The output may include an RC filter or bandpass filter configured to reduce high frequency noise. Optimal matching between the receive coil and preamplifier may occur when the coil resistance at the receive frequency is substantially equal to the ratio of the preamplifier noise voltage to the preamplifier noise current. In certain instances, the matching may be achieved using baluns and matching capacitors and inductors in low-pass, high-pass, and band-pass configurations.

Figure 8A:
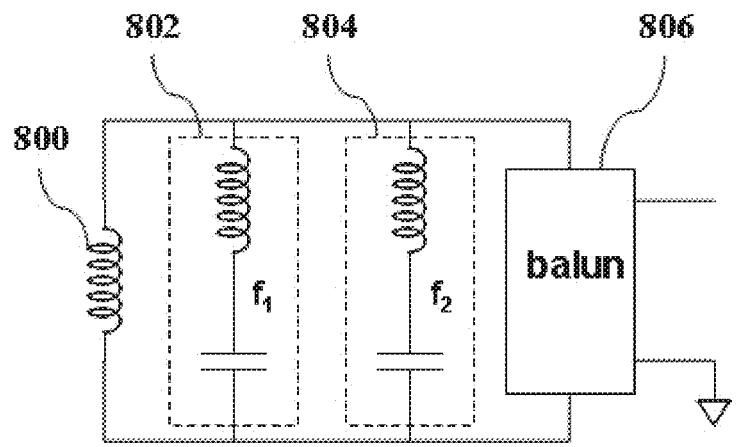
FIGS. 8A and 8B are circuit diagrams illustrating two alternative receive coil circuits for providing a dual-tuned receive coil, according to embodiments of the present disclosure.
Figure 8B:
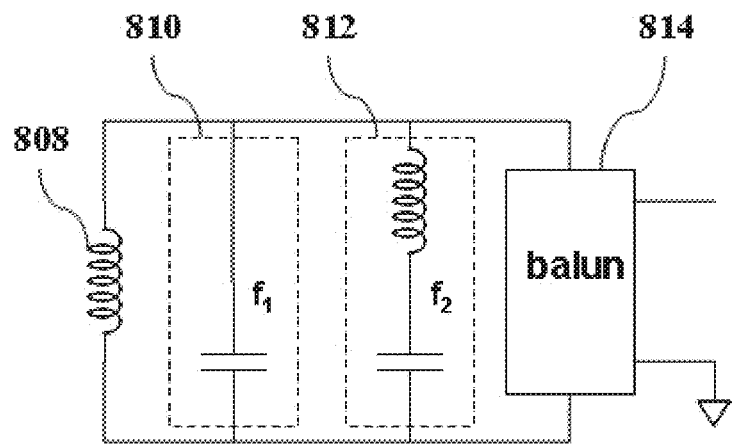

FIGS. 8A and 8B illustrate two alternative receive coil circuits for providing a dual-tuned receive coil. The circuit of FIG. 8A includes receive coil 800, first frequency matching circuit elements 802, second frequency matching elements 804, and balun 806. Matching circuit elements 802 contain an inductor and capacitor tuned to a first frequency. Matching circuit elements 804 contain an inductor and capacitor tuned to a second frequency. The circuit of FIG. 8B includes receive coil 808, first frequency matching circuit elements 810, second frequency matching elements 812, and balun 814. Matching circuit elements 810 contain a capacitor tuned to a first frequency. Matching circuit elements 812 contain an inductor and capacitor tuned to a second frequency. Additional frequency matching elements may be added to the circuits of FIG. 8A or 8B in a similar manner to provide matching to additional distinct frequencies for a multi-tuned coil.

In some cases, the receiver is configured to be a wideband receiver. In certain embodiments, a wideband receiver is included in a device configured for x-space magnetic particle imaging. For example, the receiver may be configured to have non-resonant matching. In some instances, the receiver is configured to have non-resonant matching, such that the receive spectrum has a substantially flat amplitude and phase across a wide bandwidth. For instance, the receiver may be configured to have a receive bandwidth ranging from 1 kHz to 100 MHz, such as from 1 kHz to 50 MHz, including from 5 kHz to 25 MHz, or from 10 kHz to 10 MHz, or from 10 kHz to 5 MHz, or from 10 kHz to 1 MHz, or from 20 kHz to 500 kHz, or from 20 kHz to 250 kHz, or from 20 kHz to 200 kHz. In certain embodiments of x-space MPI, the receiver is configured to have a wide bandwidth. In these embodiments, the device may be configured to include noise matching. In some instances, the device includes a transformers and/or a balun configured to perform noise matching. In certain instances, the receiver includes a pre-amplifier. The pre-amplifier may be configured to have low voltage noise, such as 1000 nV/√Hz or less, including 500 nV/√Hz or less, for instance 250 nV/√Hz or less, or 100 nV/√Hz or less, or 50 nV/√Hz or less, or 25 nV/√Hz or less, or 20 nV/√Hz or less, or 15 nV/√Hz or less, or 10 nV/√Hz or less, or 5 nV/√Hz or less, or 4 nV/√Hz or less, or 3 nV/√Hz or less, or 2 nV/√Hz or less, or 1 nV/√Hz or less. For example, the pre-amplifier may include a junction gate field-effect transistor (JFET), or the like.

Signal to Noise Ratio and Noise Matching Theory

When the receive coil and preamplifier dominate the noise in a receiver, noise matching the receiver to the pickup coil may improve SNR. Optimal matching may occur when the coil impedance is substantially matched to the voltage and current noise of the preamplifier. In some instances, assuming optimal matching, the dominant noise source may be the coil. A high-Q receiver coil and bandwidth narrowing may increase preamplifier SNR for a given $f_0$ by reducing the preamplifier noise figure, the coil noise for a given volume, and the detection bandwidth. In certain embodiments, because these factors are independent of $f_0$, the detection frequency may be increased to reach body noise dominance without increasing receiver bandwidth. In some instances, the imaging region may be increased by increasing $H_{tot}=H_0+H_1$. Certain embodiments of the present disclosure thus provide narrowband MPI which increases SNR for a fixed SAR.

The signal from the MPI receive coil may be amplified prior to digitization. The amplifier noise may be minimized when the receiver coil is noise matched to the preamplifier. In some cases, noise matching may be optimized by minimizing the ratio of output noise to input noise, i.e., the noise gain ratio. The noise gain ratio may be minimized when the real coil resistance at resonance is $R_{coil}=e_n/i_n$, where $e_n$ and $i_n$ are, respectively, the voltage and current noise amplitude per unit bandwidth of the preamplifier.

In certain instances, the MPI device has a noise figure of 10 dB or less, such as 5 dB or less, including 3 dB or less, or 1 dB or less, for instance 0.75 dB or less, or 0.5 dB or less, or 0.25 dB or less, or 0.1 dB or less. In some cases, the noise figure is 50% or less greater than the theoretical best case noise figure, such as 40% or less, or 30% or less, or 20% or less, or 15% or less, or 10% or less, or 5% or less, or 1% or less greater than the theoretical best case noise figure.

In certain embodiments, the noise figure (NF) is represented by the formula:

$$NF = 10\log_{10}\left[\frac{e_n^2 + i_n^2 R_S^2 + 4kTR_s}{4kTR_s}\right]$$

where $e_n$ and $i_n$ are, respectively, the voltage and current noise amplitude per unit bandwidth of the preamplifier, $R_s$ is the coil impedance, k is the Boltzmann constant, and T is the temperature. In some instances, NF is maximized when $R_{coil}=e_n/i_n$.

Assuming optimal matching, then the dominant noise source may be the coil. Then the coil noise is:

$$e_c=(4kT_c\Delta R)^{1/2}$$

and the resistance can be estimated assuming a long straight cylindrical conductor and the skin effect:

$$R \propto (f_0\rho(T_c))^{1/2}$$

where $f_0$ is the detection frequency and $\rho(T_c)$ is the resistivity of the conductor coil at temperature $T_c$.

The received signal in contained in the harmonics of $\xi$:

$$\xi \propto \int_{sample}(\partial/\partial t)\vec{B}_1 \cdot \vec{M} dV_s \propto K(f_0)M_0V_sf_0$$

where $K(f_0)\leq 1$ models relaxation effects, $M_0$ is the ferromagnetic magnetization density in the imaging region, and $V_s$ is the volume of the imaging region. Then, the SNR after the pre-amplifier is:

$$SNR \propto \frac{FK(f_0)M_0V_sf_0^{3/4}}{(4kT_c\Delta f\rho(T_c))^{1/2}}$$

where F is the noise factor $F=10^{NF/10}$. Thus, bandwidth narrowing and a high-Q receiver coil may increase SNR, since it enables low pre-amplifier noise figure, minimum coil noise for a given volume, small detection bandwidth, high detection frequency, and ability to increase the imaging region.

In certain embodiments, the magnetic particle imaging device is configured to have a signal to noise ratio (SNR) ranging from 1 to 1,000,000, such as from 5 to 750,000, including from 10 to 500,000.

Signal Processor

Aspects of the magnetic particle imaging device include a signal processor. The signal processor may be configured to convert the signal detected by the receiver into an image of the magnetic particles in the sample. For example, the signal processor may be configured to convert the detected signal into a one dimensional image of magnetic particles in the sample. The one dimensional image may represent a partial field of view of the magnetic particles in the sample. In some cases, the signal processor is configured to combine two or more partial field of view images into the image of the magnetic particles in the sample. For instance, two or more partial field of view images may be combined to produce a two or three dimensional image of the magnetic particles in the sample.

In certain embodiments, the signal processor is configured to convert the detected signals into a multi-dimensional image of the magnetic particles in the sample. The multi-dimensional image may be a native multi-dimensional image. By "native" is meant that the image is fundamental to the technique, and does not require pre-characterization of a specific type of nanoparticle in the system. To do this, an embodiment may image using a partial field of view technique. For example, the signal processor may be configured to convert the detected signals into native 2D partial field of view images of the magnetic particles in the sample. These native 2D images may further be combined to produce a larger field of view 2D image, or a 3D image of the magnetic particles in the sample. In other embodiments, the signal processor is configured to convert the detected signals into native 3D partial field of view images of the magnetic particles in the sample. These native 3D images may be further combined to produce a larger field of view 3D image of the magnetic particles in the sample.

The signal processor may be any type of processor capable of converting the detected signals into an image of the magnetic particles in the sample, and in some instances includes a computer processor programmed to convert the detected signals into an image of the magnetic particles in the sample. The signal processor may include additional electronic circuits and devices, such as but not limited to, analog to digital converters, digital to analog converters, digital down-converters, combinations thereof, and the like.

In certain instances, the magnetic particle imaging device is configured to have a field of view ranging from 0.1 mm to 500 cm, such as from 1 mm to 250 cm, including from 5 mm to 100 cm, or from 1 cm to 50 cm, or from 1 cm to 25 cm, or from 1 cm to 10 cm.

Resolution

Spatial resolution of the system is the ability to accurately depict two distinct points of equal intensity in space. In certain embodiments, the magnetic particle imaging device is configured to have a resolution ranging from 1 cm to 1 nm, such as from 0.5 cm to 100 nm, including from 1 mm to 1 μm, for instance from 1 mm to 100 μm, or from 1 mm to 500 μm. For example, the magnetic particle imaging device may be configured to have a resolution of 1 cm or less, such as 0.5 cm or less, including 1 mm or less, or 500 μm or less, or 100 μm or less, or 10 μm or less, or 1 μm or less, or 500 nm or less, or 100 nm or less.

In certain embodiments, the device is configured to detect magnetic particles in a sample at different resolutions. For instance, the device may be configured to detect magnetic particles in a sample at a first resolution and then subsequently detect the magnetic particles in the sample at a second resolution. In some cases, the first resolution is a lower resolution than the second resolution. In other cases, the first resolution is a higher resolution than the second resolution. In some instances, the device is configured to analyze the signals detected at different resolutions. For example, the device may be configured to combine the signals detected at different resolutions. Analyzing the signals detected at different resolutions may facilitate the recovery of low frequency information that may have been lost due to filtering of the detected signal. For example, combining the signals detected at different resolutions may facilitate the recovery of low frequency image data that may have been lost due to high pass filtering of the detected signal.

Sensitivity

The sensitivity of a magnetic particle imaging device relates to the minimum amount of magnetic particles in a sample that can be detected by the device. In certain embodiments, the magnetic particle imaging system is configured to have a sensitivity ranging from 1 mg to 1 pg, such as from 100 μg to 50 pg, including from 10 μg to 0.1 ng, for instance from 1 μg to 0.1 ng. In some cases, the magnetic particle imaging device is configured to have a sensitivity of 1 mg or less, such as from 100 μg or less, including from 10 μg or less, or 1 μg or less, or 100 ng, or less, or 10 mg or less, or 1 ng or less, or 0.1 ng or less, or 50 pg or less, or 10 pg or less, or 1 pg or less.

Linearity

In certain embodiments, the magnetic particle imaging device is configured to produce a linearly varying signal with respect to the concentration of magnetic particles in the non-saturating magnetic field region. A linearly varying signal may facilitate the determination of the relative amount of magnetic particles in a region of the sample as compared to other regions of the sample. The amount of magnetic particles in a region of the sample may be represented in an image of the magnetic particles by the intensity of the signal in that region. For instance, a region with a relatively large amount of magnetic particles may be represented by a brighter area in the image or an area of a color associated with a larger amount of magnetic particles.

Shift Invariant

In certain embodiments, the magnetic particle imaging device is configured to produce signal that is shift invariant. By "shift invariant" is meant that the device is configured to produce a linearly varying signal with respect to the concentration of the magnetic nanoparticles in the non-saturating magnetic field region, where shifting the position of the non-saturating magnetic field region does not change the linearity of the signal. As such, as described above, the device may be configured to produce a scanning magnetic field that positions the non-saturating magnetic field region in the magnetic field. In some instances, the device is configured to produce a linearly varying signal as the position of the non-saturating magnetic field is moved through the magnetic field.

Gridding

In certain embodiments, the signal processor is configured to correlate the detected signals to the position of the non-saturating magnetic field region when the signal was acquired. Correlating the detected signal to the instantaneous position of the non-saturating magnetic field region may be referred to herein as "gridding". In certain instances, the signal processor is configured to grid the detected signals as part of producing an x-space image of magnetic particles in a sample. For example, the signal processor may be configured to process the detected signal to ensure the phase linearity, as described above, and then the processor may be configured to grid the received signal to the instantaneous location of the non-saturating magnetic field region. In some instances, gridding the detected signals to the position of the non-saturating magnetic field region when the signal was acquired facilitates the production of the native image of the magnetic particles (e.g., a 2D or 3D image of the magnetic particles).

Circuitry

The magnetic particle imaging device may also include circuitry associated with the excitation signal source and the receiver. FIGS. 7A and 7B are schematic diagrams of the transmit and receive chains, respectively. The excitation circuitry 700 shown in FIG. 7A includes an RF power amplifier 702, second harmonic trap 704, high-pass filter 706, and high-frequency resonant coil 708. The excitation circuitry 700 may also include an LF power amplifier 718, low-pass filter 716, and LF coil 714 isolated from the sample 710 and RF chain by RF shield 712. The RF excitation and LF intermodulation signals are generated by these chains to excite magnetic particles in sample 710. In certain cases, the signal generators are phase locked to a coherent detector. In some instances, the RF amplifier 702 drives the matched, water-cooled resonant transmit coil 708 to generate a sinusoidal magnetic field at $f_0=150$ kHz with peak-to-peak amplitude of 6 mT. In certain cases, the intermodulation coil 714, driven by audio amplifier 718, generates a sinusoidal magnetic field at $f_0=200$ Hz with peak-to-peak amplitude of 5.9 mT.

Figure 9A:
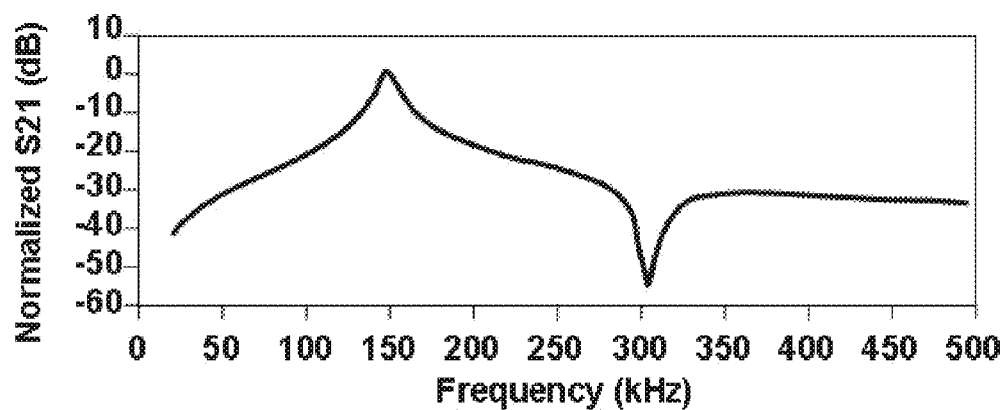
FIGS. 9A and 9B are graphs of the transfer functions for transmit and receive circuit chains of a MPI device, according to embodiments of the present disclosure.
Figure 9B:
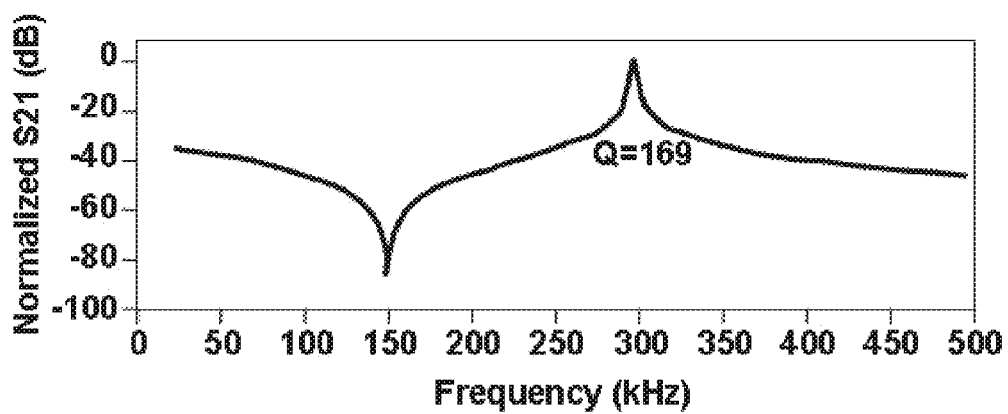

The receive circuitry 750 shown in FIG. 7B includes a receive coil 752, balun 754, first preamplifier stage 756, first fundamental trap 758, second preamplifier stage 760, second fundamental trap 762, and preamplifier stage 764. In certain embodiments, the interfacing electronics are designed to prevent intermodulation in the RF and LF amplifier output stages (FIG. 7A) and in the preamplifier (FIG. 7B) through the use of high-pass, low-pass, and notch filters. The RF transmit chain 700 may have a resonant transmit coil 708 at 150 kHz and a second harmonic trap 704 at 300 kHz. The receive chain 750 may have a fundamental harmonic trap 758 at 150 kHz and high-Q receive coil 752 at 300 kHz. The transfer functions for the transmit and receive chains are shown, respectively, in FIGS. 9A and 9B, which show 80 dBV or more of isolation between the transmit and receive frequencies. In some cases, each isolation stage, including RF shield, provides approximately 30 dB of isolation. In certain embodiments, the inductors are high-Q RF toroids or are air core. High power capacitors may be used in the transmit chain and high-Q capacitors may be used in the receive chain.

FIG. 7C is a schematic diagram of the transmit chain according to certain embodiments of the present disclosure. The RF transmit chain includes RF amplifier 780, $2f_0$ filter 782, matching capacitor 784, high-power capacitor 786, RF coil 788, and large capacitor 790. In some cases, the filter 782 reduces the effect of harmonics in the output spectrum of the RF amplifier. The filter circuit elements inductors $L_1$, $L_2$, and capacitor $C_1$ resonate so that the fundamental frequency $f_0$ passes through the filter. Inductor $L_2$ and capacitor $C_1$ may be tuned so that there is a shunt to ground at $2f_0$. Additional shunts at $3f_0$, $4f_0$, and higher may also be included, up to shunt at $Nf_0$ provided by $L_{N-1}$ and capacitor $C_N$.

In some instances, the preamplifier uses low-noise op-amps in stages 756, 760, 764 matched to a high-Q coil 752 of $Z_{coil}=2$ k$\Omega$ at resonance. The preamplifier may be noise matched to the receive coil using a 4:1 balanced-to-unbalanced impedance transformer (balun) 754. Some embodiments may include feedback circuitry configured to prevent phase and magnitude drift in the RF transmit power and excitation field strength caused by loading of the transmit coil and heating. The feedback circuit may include a cartesian feedback circuit or a current feedback circuit. The current or field can be measured in various ways such as using a pickup coil or a current sensor/shunt resistor. In some instances, the feedback circuitry facilitates the regulation of the field that the sample experiences, and the current through the transmit coil may depend on the feedback circuitry. In some embodiments, feedback damping is used to widen the bandwidth of the receive coils. Feedback damping may be performed by feeding back the received signal out of phase to the receive coil, as shown in FIG. 7D. In some embodiments, a rotating (quadrature) excitation field is used to increase the detectable signal.

In other embodiments, the device includes a wideband receiver, as described above. The wideband receiver may be configured to have a substantially flat amplitude and phase across the receive spectrum. In certain instances, the receiver is configured to include a high pass filter. In these embodiments, the received signal may be filtered by the high pass filter and the device may be configured to correct the filtered signal. In some instances, the filtered signal is corrected to produce a signal with a substantially flat amplitude and phase, as described above.

Signal Harmonics and Sideband Tones

FIG. 3A is a graph of received signal level versus frequency for a conventional MPI technique showing multiple received harmonics such as second harmonic ($2f_0$) 302. The graph shows a simulated signal received by an untuned pickup coil. In conventional MPI techniques, the fundamental ($f_0$) 300 is typically not used because it may be contaminated by direct feed through from the excitation field.

Figure 3B:
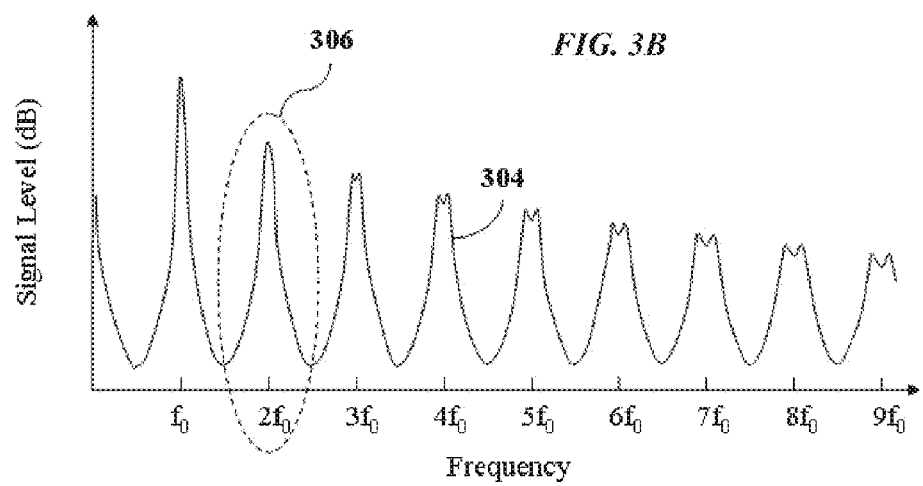
FIG. 3B is a graph of received signal level versus frequency for an MPI technique using intermodulation, according to embodiments of the present disclosure.

FIG. 3B is a graph of received signal level versus frequency for an MPI technique using intermodulation according to embodiments of the present disclosure. The graph shows a simulated signal envelope 304 received by an untuned pickup coil. Intermodulation generates detectable intermodulation products around the main harmonics, spreading the spectral information. These sideband intermodulation products around the main harmonics are absent in conventional MPI techniques that do not use intermodulation. In some cases, the amplitude and phase of the intermodulation products vary as a function of position. Each peak in the envelope may contain multiple intermodulation sideband tones. For example, details of the tones contained in peak 306 around the second harmonic are shown in FIG. 3C. Tone 308 is the second harmonic ($2f_0$). Clustered around this harmonic are intermodulation tones such as tone 310 at frequency $2f_0+f_1$, tone 312 at frequency $2f_0+2f_1$, and tone 314 at frequency $2f_0+3f_1$. Because $f_0$ is significantly larger than $f_1$, the bandwidth required to receive the seven harmonics $2f_0$ through $8f_0$ in FIG. 3A is larger than the bandwidth required to receive the seven intermodulation tones $2f_0-3f_1$ through $2f_0+3f_1$. As a result, intermodulation allows the use of a narrowband receiver to detect a similar number of distinct frequency signals. This, in turn, allows the use of a tuned receiver and improved signal to noise ratio (SNR).

Magnetic Particles

Any convenient magnetic particle may be employed. Magnetic particles are magnetizable particles that, when exposed to an excitation signal, are detectable by the magnetic particle imaging device. Magnetic particles of interest may be configured to be substantially saturated in the magnetic field produced by the magnetic source of the magnetic imaging device, but not saturated in the non-saturating magnetic field region of the magnetic field.

Magnetic particles useful in the practice of certain embodiments of the present disclosure are magnetic (e.g., ferromagnetic) colloidal materials and particles. The magnetic nanoparticles can be high moment magnetic nanoparticles which may be super-paramagnetic, or synthetic anti-ferromagnetic nanoparticles which include two or more layers of anti-ferromagnetically-coupled high moment ferromagnets. Both types of magnetic particles appear "nonmagnetic" (e.g., have a magnetization of substantially zero) in the absence of a magnetic field. Magnetic particles with a substantially zero remnant magnetization may not substantially agglomerate with each other in solution in the absence of an external magnetic field. In accordance with certain embodiments, magnetizable particles suitable for use include one or more materials such as, but not limited to, paramagnetic, super-paramagnetic, ferromagnetic, and ferrimagnetic materials, as well as combinations thereof, and the like.

In certain embodiments, the magnetic particles have remnant magnetizations that are small or substantially zero, such that they will not agglomerate in solution. Examples of magnetic particles that have small remnant magnetizations include super-paramagnetic particles and anti-ferromagnetic particles. In certain cases, the magnetic particles have detectable magnetic moments under a magnetic field of 1 T or less, such as 100 mT or less, or 10 mT or less, or 1 mT or less. In some embodiments, the magnetic labels are colloidally stable, e.g., nanoparticle compositions may be present as a stable colloid. By colloidally stable is meant that the nanoparticles are evenly dispersed in solution, such that the nanoparticles do not substantially agglomerate. In certain embodiments, to prevent clumping, the nanoparticles may have no net magnetic moment (or a very small magnetic moment) in zero applied field.

The magnetic particles may be chemically stable in a biological environment, which may facilitate their use in the assay conditions. In some cases, the magnetic particles are biocompatible, i.e., water soluble and functionalized so that they may be readily attached to biomolecules of interest, e.g., a antibody that specifically binds to a target analyte. By associating or binding magnetic particles to a specific antibody, the magnetic particles may be targeted to specific areas of the body in a subject through the specific binding interactions between the antibody and complementary antigen. In some instances, the magnetic label may be bound to the protein or antibody as described above through a non-covalent or a covalent bond with each other. Examples of non-covalent associations include non-specific adsorption, binding based on electrostatic (e.g. ion, ion pair interactions), hydrophobic interactions, hydrogen bonding interactions, specific binding through a specific binding pair member covalently attached to the surface of the magnetic particle, and the like. Examples of covalent binding include covalent bonds formed between the biomolecule and a functional group present on the surface of the magnetic particle, e.g. —OH, where the functional group may be naturally occurring or present as a member of an introduced linking group.

In certain embodiments, the magnetic nanoparticles are high moment magnetic particles such as Co, Fe or CoFe crystals, which may be super-paramagnetic at room temperature. Magnetic nanoparticles suitable for use herein include, but are not limited to, Co, Co alloys, ferrites, cobalt nitride, cobalt oxide, Co—Pd, Co—Pt, iron, iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, Ni alloys, combinations thereof, and the like. In some embodiments, a functionalized coating, such as, but not limited to, a thin layer of gold plated onto a magnetic core, or a poly-L-lysine coated glass surface, may be attached to the magnetic core. These types of coating may facilitate the attachment of biomolecules, such as antibodies, antigens, proteins, etc. to the surface of the magnetic particles. In some embodiments, to facilitate the bio-conjugation of the nanoparticle, a gold cap (or cap of functionally analogous or equivalent material) is layered on the top of the layers of anti-ferromagnetic material so that the nanoparticle can be conjugated to biomolecules via a gold-thiol or other convenient linkage. Surfactants may be applied to the nanoparticles, such that the nanoparticles may be water-soluble. The edges of the nanoparticles can also be passivated with Au or other inert layers for chemical stability.

In some cases, the magnetic particles may include two or more ferromagnetic layers, such as $Fe_xCo_{1-x}$, where x is 0.5 to 0.7, or $Fe_xCo_{1-x}$ based alloys. These ferromagnetic layers may be separated by nonmagnetic spacer layers such as Ru, Cr, Au, etc., or alloys thereof. In certain cases, the spacer layers include ferromagnetic layers coupled antiferromagnetically so that the net remnant magnetization of the resulting particles are substantially zero. In some cases, the antiferromagnetic coupling strength is such that the particles can be saturated (i.e., magnetization of all layers become parallel) by an external magnetic field of 10 mT or less. In some cases, the antiferromagnetic coupling strength depends of the layer thicknesses and the alloy composition of the spacer layer.

In certain embodiments, the magnetic particles are nanoparticles. By "nanoparticle" is meant a particle having an average size (e.g., diameter) in the range of 1 nm to 1000 nm. In certain embodiments, the size (e.g., mean diameter) of the magnetic nanoparticles is sub-micron sized, e.g., from 1 nm to 1000 nm, or from 1 nm to 500 nm, or from 5 nm to 250 nm, such as from 5 nm to 150 nm, including from 5 nm to 50 nm. For example, magnetic nanoparticles having a mean diameter of 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 70 nm, 80 nm, 90 nm, 100 nm, 110 nm, 120 nm, 130 nm, 140 nm, 150 nm, and 200 nm as well as nanoparticles having mean diameters in ranges between any two of these values, are suitable for use herein. In certain embodiments, the magnetic particles are substantially uniform in shape. For example, the magnetic particles may be spherical in shape. In addition to a spherical shape, magnetic nanoparticles suitable for use herein can be shaped as disks, rods, coils, fibers, pyramids, and the like.

In certain embodiments, the magnetic particles include two or more magnetic sub-particles associated with each other. The associated magnetic sub-particles may be coated with a coating to form the magnetic particle. In some cases, the coating is a polymer, such as, but not limited to, dextran, carboxydextran, and the like. In some cases, the magnetic particles include Resovist® super-paramagnetic iron oxide (SPIO) nanoparticles (Bayer-Schering).

Figure 10A:
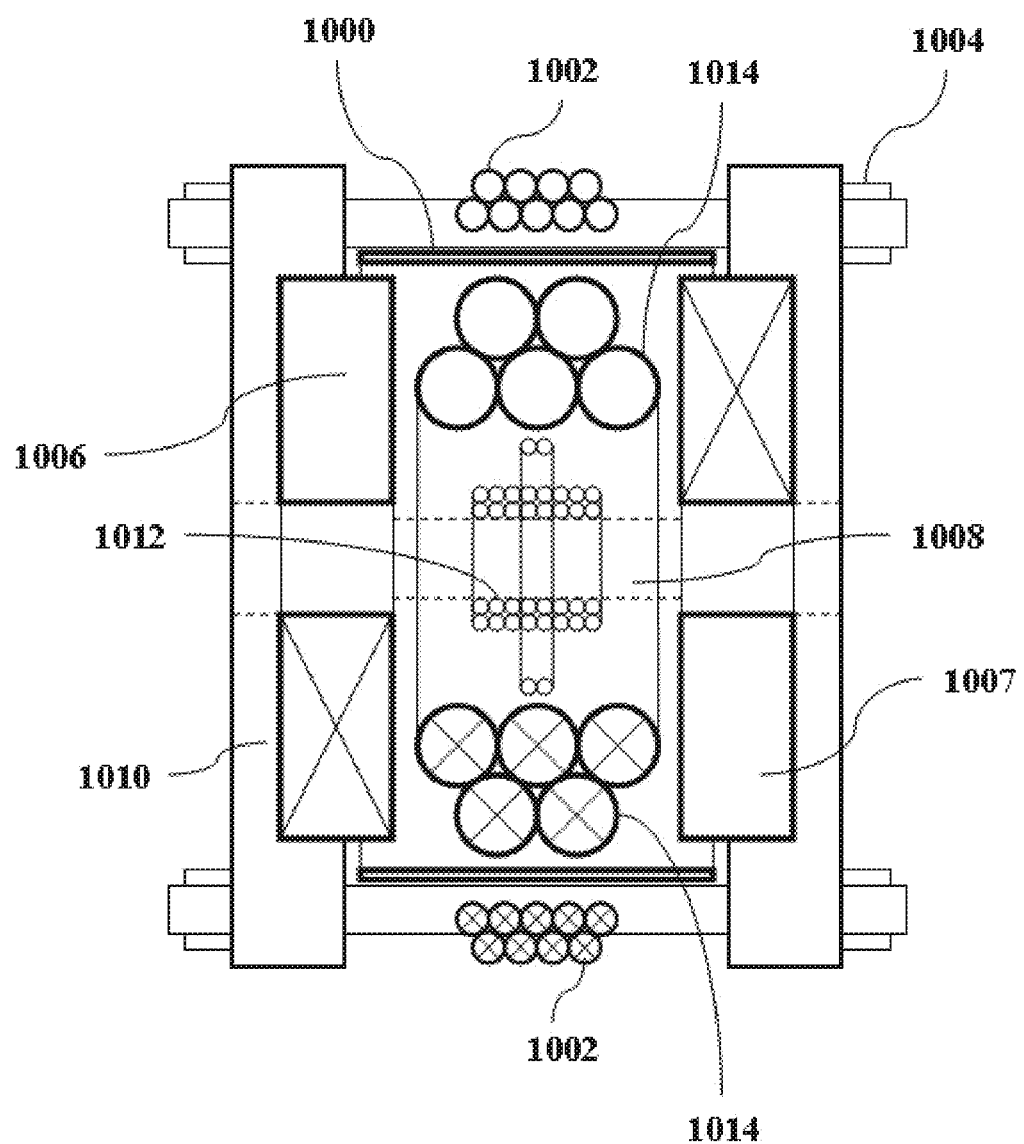
FIG. 10A is a cross-sectional view of an MPI apparatus, according to embodiments of the present disclosure.

An example of an MPI apparatus according to an embodiment of the present disclosure is shown in FIG. 10A. NdFeB ring magnets 1006, 1007 create a static inhomogeneous magnetic gradient field having a field-free region located near the center of imaging bore 1008. Ring magnets 1006, 1007 have a mean diameter of 7.62 cm and a center-to-center separation of 6.85 cm. The magnetic field is approximately linear axially down the bore, with a gradient of dB/dz=4.5 T/m. Coronal gradients are dB/dx=dB/dy=2.6 T/m. Water-cooled excitation solenoid 1014 generates a dynamic magnetic field that is superimposed on the static field and can excite magnetic particles in the imaging bore 1008. In addition, intermodulation solenoid 1002 generates a dynamic magnetic field that is also superimposed on the static field. Magnetic shield 1000 passively isolates the AC excitation solenoids 1002 and 1014 from interaction with other components to reduce unwanted heating and signal interference. Signals from magnetic particles located in the imaging bore 1008 are received by concentric gradiometer receive coil 1012. The mechanical frame for the apparatus includes a G10 plate 1010 for mounting ring magnets 1006, 1007 and aluminum bolt 1004.

FIG. 10B is a perspective cut-away view of a device according to an embodiment of the present disclosure. The device contains NdFeB permanent magnets 1020, 1022 that produce an inhomogeneous field with a field-free point in the center of the bore 1024, water cooled electromagnet coils (not shown) positioned inside bore 1024 to generate a radio-frequency excitation magnetic field along the longitudinal z-axis and water cooled electromagnet coils to generate low-frequency excitation magnetic fields along the x-axis 1026, y-axis 1028, 1030, and z-axis. The x, y, and z axis electromagnets also generate a scanning magnetic field to move the field-free-point. The permanent magnets produce a z-gradient of 8 T/m and x-y-gradient of 4 T/m. In one implementation, the inner diameter is 3 inches and the outer diameter is 12 inches, and the interior is potted with epoxy to reduce vibration. The RF excitation coils (not shown) positioned inside bore 1024 are driven by a 750 Watt continuous power amplifier. The LF coils are driven by an 800 Amp peak-to-peak amplifier.

Methods

Aspects of the present disclosure also include a method of imaging magnetic particles in a sample. The method includes applying a magnetic field having a non-saturating magnetic field region (e.g., a field free region, FFR) to a sample that includes magnetic particles. As described above, the magnetic particle imaging device includes magnetic field sources that produce a saturating magnetic field of sufficient strength that magnetic particles in the magnetic field are saturated, except for those magnetic particles that are in the non-saturating magnetic field region of the magnetic field. Application of the magnetic field to the sample may saturate the magnetic particles in the magnetic field and may not saturate the magnetic particles in the non-saturating magnetic field region.

The magnetic particles in the non-saturating magnetic field region may be excited by an excitation signal. As such, in certain embodiments, the method includes applying an excitation signal to the magnetic particles in the non-saturating magnetic field region to produce a detectable signal from the magnetic particles in the non-saturating magnetic field region. Applying the excitation signal may include applying two or more excitation signals to the magnetic particles in the non-saturating magnetic field region. For example, the applying may include applying an RF excitation signal to the magnetic particles in the non-saturating magnetic field region. In certain instances, the applying may include applying an intermodulation signal, such as a low frequency (LF) intermodulation signal to the magnetic particles in the non-saturating magnetic field region.

The excitation signal sources may be configured in various orientations and spatial arrangements. In some embodiments, the excitation signal source is configured to create a transverse field along the length of the imaging area of the magnetic particle imaging device. In some embodiments, intermodulation may be applied separately and sequentially to the RF excitation field in the x, y, and z directions. For example, intermodulation may be applied in the x direction alone, while no intermodulation is used in either the y or z directions. In some cases, intermodulation is applied sequentially to just the y direction, and then just to the z direction. The intermodulation may also be applied in a combination of directions at once, e.g., a rotating x-y field created by phase-shifted x and y intermodulation waveforms.

In certain embodiments, the method of imaging magnetic particles in the sample also includes detecting a signal from the magnetic particles in the non-saturating magnetic field region. In some cases, the detecting includes detecting the signals from the magnetic particles using one or more receivers.

Methods of the present disclosure further include analyzing the signal to produce an image of the magnetic particles in the sample. The analyzing may include converting the detected signals into one or more partial field of view images of the magnetic particles in the sample. In some cases, the analyzing further includes combining the partial field of view images into the image of the magnetic particles in the sample. For example, the analyzing may include converting the detected signals into a one dimensional image that represents a partial field of view of the magnetic particles in the sample. The method may further include combining two or more one dimensional partial field of view images into a two or three dimensional image of the magnetic particles in the sample. In some instances, combining the partial field of view images into the image of the magnetic particles in the sample is performed as part of an x-space magnetic particle imaging method.

In certain embodiments, the analyzing includes converting the detected signals into a multi-dimensional image of the magnetic particles in the sample. The analyzing may produce native multi-dimensional images, such as native 2D or 3D images. For example, the analyzing may include converting the detected signals into a native 2D partial field of view image of the magnetic particles in the sample. The analyzing may further include combining two or more of the native 2D images to produce a larger field of view 2D image or a 3D image of the magnetic particles in the sample. In some instances, the analyzing includes converting the detected signals into a native 3D image, such as a native 3D partial field of view image of the magnetic particles in the sample. The analyzing may further include combining the 3D partial field of view images into a larger field of view 3D image of the magnetic particles in the sample. In certain embodiments, combining two or more partial field of view images into a larger field of view image facilitates the recovery of low frequency information (e.g., low frequency image data) in the detected signal that may be lost during filtering (e.g., high pass filtering) of the detected signal.

In certain embodiments, the analyzing includes correlating the detected signals to the position of the non-saturating magnetic field region when the signal was acquired. Correlating the detected signal to the instantaneous position of the non-saturating magnetic field region may be referred to herein as "gridding". For example, the analyzing may include gridding the received signal to the instantaneous location of the non-saturating magnetic field region. In some instances, gridding the detected signals to the position of the non-saturating magnetic field region when the signal was acquired facilitates the production of the native image of the magnetic particles (e.g., a 2D or 3D image of the magnetic particles). In certain cases, the analyzing includes gridding as part of producing an x-space magnetic particle image.

In certain embodiments, receiver signal processing includes using a dual-lock in amplifier system to receive the signal. The signal may be downmixed centered at two and three times the high-frequency RF excitation. The downmixed signal may then be downmixed again at the LF*(0, +/−1, +/−2, +/−3, etc.).

In some cases, the signal from the receive coil and preamplifier chain is transmitted to a digital down-converter circuit block that down-converts the signal to baseband with channelization. The circuit block may independently downsample each intermodulation signal so that each subband tone is channelized. For example, intermodulation products 310, 312, 314 shown in FIG. 3C are separately downconverted and sampled. During operation, these intermodulation products may be continuously sampled and stored, associating the stored signal with a corresponding position of the field-free region.

Figure 11A:
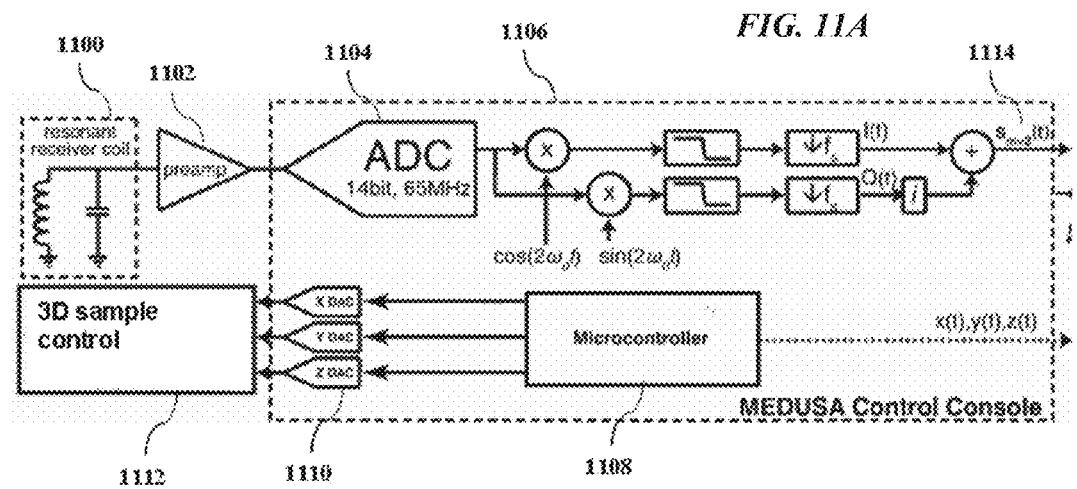
FIGS. 11A and 11B are block diagrams of signal processing circuit blocks used to process the signals from the receive coil circuit chains, according to embodiments of the present disclosure.
Figure 11B:
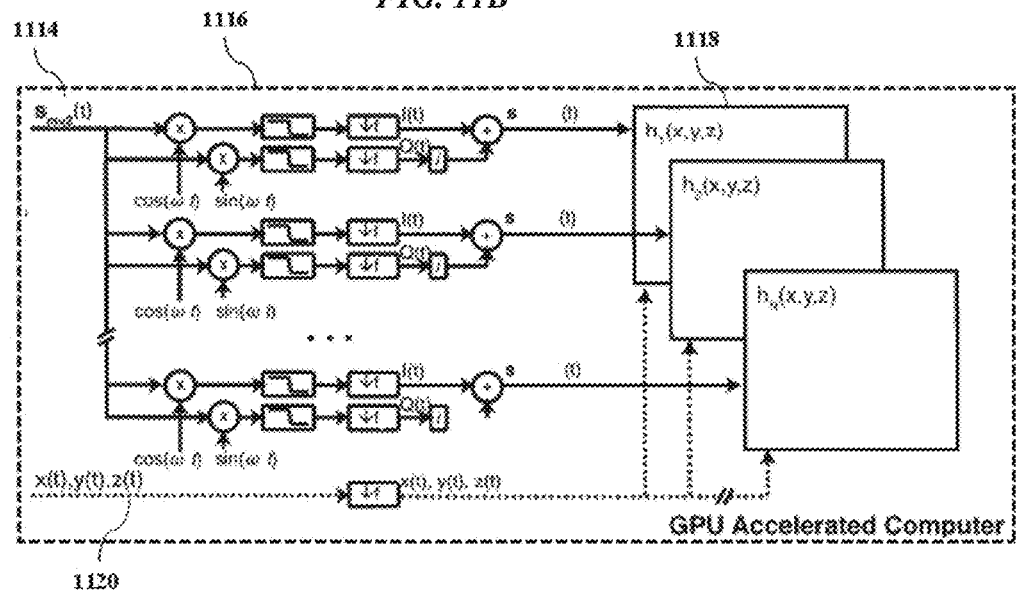

FIGS. 11A and 11B are block diagrams of signal processing circuit blocks used to process the signals from the receive coil circuit chains. The circuit block 1106 of FIG. 11A receives signals originating from the receiver coil 1100 and preamplifier 1102. The signals are digitized by 14 bit 65 MHz analog-to-digital converter 1104 and then separated into in-phase and quadrature signal components and down-sampled to produce corresponding components I(t) and Q(t) of digital signal 1114, $s_{m=2}(t)$. This signal may have a bandwidth of 30 kHz to 100 kHz or more. Block 1106 also contains microcontroller 1108 which provides x(t), y(t), z(t) control signals to 3D sample control block 1112 in order to control relative 3D translation between the sample and the field-free region. Digitized signal 1114 is fed into processing block 1116 of FIG. 11B where its intermodulation products are independently channelized and down-sampled to produce in-phase and quadrature component signals I(t) and Q(t) for each of N subbands around the harmonic. These N subband signals are then stored according to associated x(t), y(t), z(t) position coordinates 1120 in N corresponding image memory blocks $h_1(x,y,z), \ldots, h_N(x,y,z)$, such as block 1118. The processing blocks of FIG. 11B may be implemented by a GPU accelerated computer or using a field programmable gate array (FPGA) or application-specific integrated circuit (ASIC).

In certain embodiments, producing the image of the magnetic particles in the sample depends on the magnetic particle and the field-free point, which corresponds to a point-spread function (PSF) that depends on various factors such as the particle size, magnetic field gradient, and intermodulation product. In some instances, the measured PSF has higher SNR in sidebands closer to the harmonic (e.g., $2f_0$ and $2f_0 \pm f_1$), but contains more high frequency spectral content in the sidebands further from the harmonic (e.g., $2f_0 \pm 2f_1$, $2f_0 \pm 3f_1$, $2f_0 \pm 4f_1$, etc.). In some embodiments, the high SNR of the lower sidebands may be combined with the higher resolution of the upper sidebands to form a reconstructed (e.g., combined) image. In the reconstructed image, if the upper sidebands become unavailable as SNR drops, then the image resolution may decrease.

Figure 12:
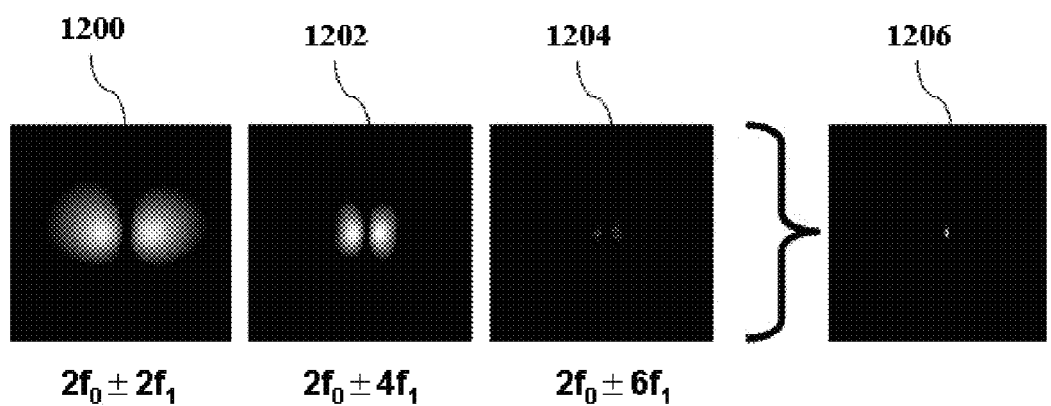
FIG. 12 shows images showing how multiple harmonic images are all different measurements of the same point source, according to embodiments of the present disclosure.

In certain embodiments, image reconstruction includes processing the detected signals. For example, the detected signals from different harmonics and/or intermodulation sidebands may be separately down-converted and stored to form a set of N distinct images $h_1(x,y,z), \ldots, h_N(x,y,z)$, each corresponding to a different frequency. Each of these images may be a convolution of the unknown magnetization. An image may be reconstructed by a method of parallel deconvolution of these images to form a single composite image. In some cases, a Fourier transform is applied to each of the detected signals $s_n(x,y,z)$ to obtain a frequency-domain representation, $Y_n(k)=F[s_n(x,y,z)]$, where k is a vector indexing the frequency domain and F is the Fourier transform. If $H_n(k)$ represents the n-th harmonic point spread function (PSF) of a point source (which can be determined by calibration using a magnetic particle smaller than the system's resolvable limit), and M(k) is the unknown magnetization distribution in the frequency domain (i.e., the Fourier transform of the unknown magnetization distribution in the spatial domain), then $Y_n(k)=H_n(k) M(k)+N_n(k)$, where $N_n(k)$ is the Fourier transform of the unknown n-th harmonic noise image. Thus, in some instances, finding the desired M(k) is equivalent to finding the slope of a complex line given the regression data $\{Y_n(k), H_n(k)\}$. There are many ways of finding the slope, e.g., using a least-squares fit. The reconstructed composite image in the frequency domain may then be given by $M(k)=H^{T*}(k) \cdot Y(k)/(H^{T*}(k) H(k))$, where H(k) and Y(k) are N-dimensional column vectors whose components are $H_n(k)$ and $Y_n(k)$, respectively. The reconstructed composite image is then m(x,y,z)= F[M(k)]. This method solves for each frequency-domain point separately. Because the least-squares problem increases linearly with the number of points, it is not the computationally limiting factor, as the fast Fourier transform (FFT) used to prepare the data scales with O(N·log N). FIG. 12 illustrates the parallel deconvolution of multiple frequency images 1200, 1202, 1204 to produce a composite image 1206.

The reconstruction method described above may amplify noise at higher-frequency points in the frequency domain where SNR in the reference images are low. Accordingly, embodiments of the present disclosure provide methods to address this increase in noise at higher-frequencies. A non-linear processing step may be used to degrade reconstructed image resolution while improving the composite image. Specifically, points in the frequency domain with insufficient SNR may be set to zero:

$$M(k) = \begin{cases} 0 & \sum_{n=1}^{N} |H_n(k)| < \varepsilon \\ H^{T*}(k) \cdot Y(k)/(H^{T*}(k) \cdot H(k)) & \text{otherwise} \end{cases}$$

where $\varepsilon$ is an experimentally determined threshold that depends on the SNR. In an alternative thresholding technique, each element where $|H_n(k)|>\varepsilon$ is used and the others are removed, as follows:

$$G_n(k) = \begin{cases} 0 & |H_n(k)| < \varepsilon \\ H_n(k) & \text{otherwise} \end{cases}$$

$$M(k) = \begin{cases} 0 & \sum_{n=1}^{N} |G_n(k)| = 0 \\ G^{T*}(k) \cdot Y(k)/(H^{T*}(k) \cdot H(k)) & \text{otherwise} \end{cases}$$

The parallel deconvolution technique described here can theoretically increase the SNR of the composite image by $\sqrt{N}$, but may provide less gain at high spatial frequencies, where fewer harmonics are used in the image reconstruction. For regions of k-space where none of the N harmonics or intermodulation terms satisfy the condition $|H_n(k)|>\varepsilon$, then this region of k-space M(k) may be set to zero. In certain cases, m(x,y,z) is computed by an inverse FFT algorithm using a programmed processor (e.g., a computer).

In certain embodiments, the method further includes repositioning the non-saturating magnetic field region relative to its initial position in the sample. The non-saturating magnetic field region may be repositioned relative to its initial position in the sample by repositioning the non-saturating magnetic field region relative to the sample, repositioning the sample relative to the non-saturating magnetic field region, or a combination of the above. For example, the non-saturating magnetic field region may be repositioned by applying a scanning magnetic field to the magnetic field having the non-saturating magnetic field region. The scanning magnetic field may interact with the magnetic field lines of the magnetic field causing them to deflect from their original vectors, thus displacing the non-saturating magnetic field region from its initial position. In some instances, the scanning magnetic field may be applied along one or more axes, such as, but not limited to the x, y and/or z axes, where the z-axis is aligned with the longitudinal axis of the magnetic imaging device.

In certain embodiments, the non-saturating magnetic field region may be repositioned relative to the sample by linear translation of the sample within the magnetic field. For example, the sample may be attached to a substrate (e.g., a sample stage), where the substrate is configured to be movable in one or more directions, such as, but not limited to, directions along the x, y and/or z axes, as described above. In some instances, by combining methods that include applying a scanning magnetic field to reposition the non-saturating magnetic field region and methods that include linear translation of the sample within the magnetic field, a larger field of view may be obtained than by the use of either method alone.

In some instances, the method further includes: repositioning the non-saturating magnetic field region in the magnetic field; and repeating the detecting and repositioning to detect a plurality of signals from the magnetic particles in the non-saturating magnetic field region. As described above, the plurality of signals may be analyzed and combined to produce the image of the magnetic particles in the sample.

Figure 13A:
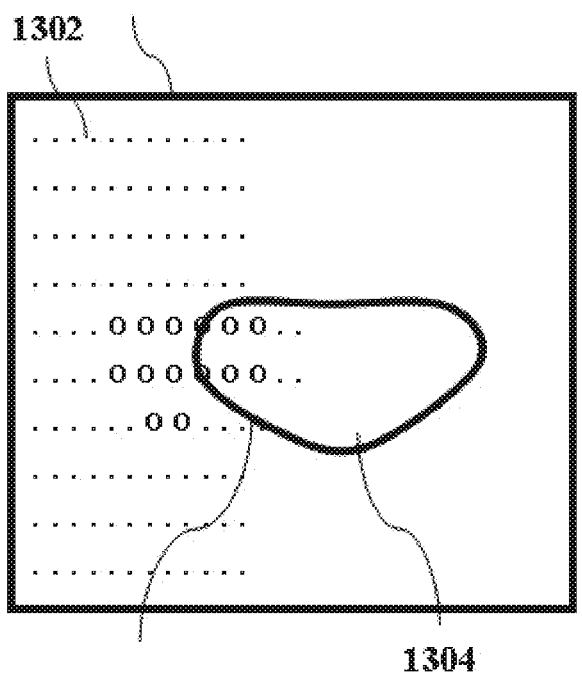
FIGS. 13A and 13B illustrate a technique of adaptive multi-resolution scanning, according to embodiments of the present disclosure.
Figure 13B:
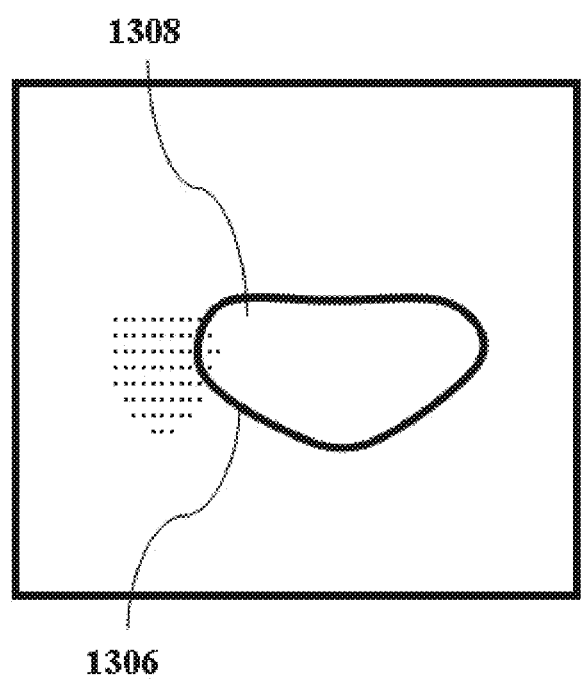

Embodiments of the method provide techniques for adaptive scanning to improve efficiency. According to an embodiment of adaptive scanning, an initial scan (e.g., a scout scan) is performed at lower resolution. The low resolution scan may be performed relatively quickly by optimizing signal acquisition to just the first and/or second and/or third harmonics, which would require less time to acquire than a high resolution scan. The low resolution scan can sample points in the imaging region at a lower spatial density as compared to a scan using the maximum resolution of the magnetic imaging device. For example, FIGS. 13A and 13B illustrate a technique of adaptive multi-resolution scanning. The imaging region 1300 shown in FIG. 13A is scanned quickly at a low resolution, sampling at each of the sample points such as point 1302. A subset of the sample points have a detected signal, such as sample point 1304. The resulting image is then analyzed to identify within the imaging region 1300 an approximate perimeter 1306 containing sample points such as point 1304 where the magnetic particles were detected. Using this information, a higher resolution scan can be performed within the identified perimeter, as shown in FIG. 13B. The spatial density of sample points, such as point 1308, may be higher than in the low resolution scan. In certain cases, the adaptive scanning technique can reduce total scan time because the low resolution scan can be performed relatively quickly and is then used to eliminate time that would otherwise be wasted during a slower high resolution scan of the entire imaging region. In certain instances, adaptive scanning is performed as part of a method for imaging magnetic particles in a sample using magnetic particle imaging device that includes a narrowband receiver. In other instances, adaptive scanning is performed as part of a method for imaging magnetic particles in a sample using magnetic particle imaging device that includes a wideband receiver (e.g., in an x-space magnetic particle imaging device).

In some cases, scanning includes using a dynamic gradient reduction technique which involves dynamically changing the gradient strength. In certain instances, the method includes varying the magnetic field strength of the magnetic field while applying the scanning magnetic field. For example, the magnetic field strength of the magnetic field may be varied as the scanning magnetic field is applied to the magnetic field to reposition the non-saturating magnetic field region. In certain instances, varying the magnetic field strength while applying the scanning magnetic field allows different resolution images to be produced by the magnetic particle imaging device. In some cases, acquiring images having different resolutions facilitates the recovery of low frequency information in the detected signal that may be lost during filtering of the detected signal. For example, combining the signals detected at different resolutions may facilitate the recovery of low frequency image data that may have been lost due to high pass filtering of the detected signal. In certain embodiments, the method includes both combining two or more partial field of view images into a larger field of view image, as described above, and varying the magnetic field strength of the magnetic field while applying the scanning magnetic field.

Scanning can also include modifying the waveform and amplitude of the intermodulation field, and determining the acquisition trajectory of the non-saturating field free region as it traverses through the sample. In some cases, the acquisition time may be minimized by determining a mathematically optimal acquisition trajectory that may be modified in real time, i.e., as more data is acquired, the system determines which part of the sample to scan for more signal and where to refine.

As an alternative to the two-step adaptive scanning technique described above, the acquisition of low and high resolution signals may be performed on a point-by-point basis during one scan. Specifically, the imaging region may be scanned as follows. At each coarse low-resolution sample point a signal is acquired, as described above in relation to FIG. 13A. The coarse sampling may be performed at a resolution less than the maximum resolution of the magnetic imaging device. Before proceeding to scan the next coarse data point, the low-resolution signals at the current coarse data point are examined to determine if there is a significant detected signal, which may indicate the presence of magnetic particles in the area (e.g., "super-pixel") surrounding the coarse sample point. If a signal is detected, then a high-resolution sampling of the area ("super-pixel") surrounding the coarse point is then performed and the signals are acquired at a high resolution sampling structure. The fine or high-resolution sampling is finer or comparable to the resolution of the highest harmonic or intermodulation image. The scanning then proceeds to the next coarse sample point and repeats the process until the entire imaging region is scanned. More complex scanning schemes than those described above could also be employed. For example, the number of signals, N, at the center of the super-pixel could be used to vary the instantaneous sampling distance from only one sample per super-pixel to fully sampled at the finest resolution of the highest harmonic or intermodulation image.

The non-saturating magnetic field region (i.e., the field-free region) allows magnetic particles in the region to be detected at once. Electromagnets or physical translation may be used to shift the non-saturating magnetic field region relative to the sample. In addition, the non-saturating magnetic field region may be rotated relative to the sample. Rotation of the non-saturating magnetic field region relative to the sample, e.g., by geometric rotation of the permanent magnets and/or the scanning magnetic sources relative to the sample, allows computed tomography techniques to be used for image reconstruction. For example, FIGS. 2B and 2C show a sample 204 being imaged using such a technique. In FIG. 2B the non-saturating magnetic field region 208 (in this case, in the form of a line, e.g., a field free line) is displaced in a direction perpendicular to the line to various other positions such as 206. At each position of the line, data is acquired. The data from all the line positions is then used to form an image slice. The orientation of the field-free line relative to the sample 204 is then changed, as shown in FIG. 2C, by rotating the permanent magnets together with the scanning magnetic sources relative to the sample. The field-free line is then displaced again to various positions such as 210 and 212, and data is again acquired at each position of the field-free line to form an image slice. Thus, a collection of image slices are acquired, each having a unique angle associated with it. For example, image slices may be acquired for a collection of distinct angles ranging uniformly over 180 degrees. Computed tomographic techniques are then used to generate an image of the sample from the collection of image slices. The field-free line allows for a projection format for MPI, which in some cases decreases the time required to image a sample.

Aspects of the present disclosure also include a method of producing an image of magnetic particles in a subject. The method includes administering magnetic particles to a subject. The magnetic particles may be administered to the subject by various methods, such as, but not limited to, ingestion, injection, inhalation, combinations thereof, and the like. For example, the magnetic particles may be provided in an injectable solution and the magnetic particles may be administered to the subject by injecting the injectable solution including the magnetic particles into the subject. The magnetic particles may diffuse through the area surrounding the injection site, or if injected into a blood vessel, may be carried through the blood vessel to an imaging site. In some instances, the magnetic particles are non-specific such that the magnetic particles freely diffuse through the body and do not target specific tissues in the subject. In some case, the magnetic particles may be associated with a targeting moiety, such as an antibody, which specifically associates with a complementary antigen. Associating a magnetic particle with an antibody may facilitate targeting the magnetic particles to specific sites in the subject base on the specificity of the antibody-antigen interactions.

For example, in medical imaging applications, magnetic nanoparticles may be components of a contrast agent that may be distributed in a subject, e.g., by injection into an organism or labeled into or onto cells. The subject, which may be animate or inanimate, human, animal, or other organism or portion thereof, is then positioned into the apparatus for imaging. To detect the concentration of magnetic particles in different regions, the field-free region is scanned relative to the subject by physical movement of the subject relative to the apparatus and/or displacement of the field-free region by dynamically changing the magnetic field using a scanning magnetic field as described above. For example, movement of the field-free region can be produced by a combination of physical translation in the axial direction with dynamic scanning in the transverse plane. The scanning can also be produced by physical translation alone or dynamic scanning alone.

At the field-free region, one or more oscillating excitation magnetic fields may be used to excite the magnetic particles situated in the field-free region. These oscillating excitation fields may have amplitudes in the range of 0.1 mT to 30 mT, as described above. The excitation fields cause the magnetization of the particles to saturate, generating harmonics that can be isolated from the fundamental using frequency domain techniques. The harmonic response at each field-free region is detected using one or more receive coils, and the detected signals are analyzed at each point to create a complete scan of the distribution of particles in the imaging region.

Utility

Magnetic particle imaging (MPI) in accordance with the embodiments of the present disclosure finds use in various applications, e.g., where it is desired to determine the distribution of magnetic particles in a sample. For example, the distribution of magnetic particle in a sample may be used to visualize the internal structure of the sample, where the magnetic particles are concentrated in certain areas within the sample. The magnetic particles may be administered to a subject, for instance by injection, and the subsequent position of the magnetic particles in the subject may be determined by MPI.

In some instances, MPI is used for the imaging of blood vessels. MPI may be used in an angiography method that may produce an image of the magnetic particles and not see tissue. Current techniques for angiography, fluoroscopy, CT Angiography (CTA), and MR Angiography (MRA), inherently see tissue in addition to the tracer agent. As a result, fluoroscopy typically requires high concentrations of iodine tracer and high resolutions are required in CTA and MRA to differentiate the tracer from surrounding tissues. Since MPI only detects the magnetic tracer, the MPI image of a blood vessel filled with magnetic particle tracer would be an image of the blood vessel convolved with the point spread function. A stenosis, for example, would be seen as darkening of the blood vessel even if the diameter of the blood vessel was below the intrinsic resolution of the image.

In some instances, Magnetic Particle Imaging (MPI) in accordance with embodiments of the present disclosure finds use as a medical imaging tracer modality with potential applications in human or small animal angiography, cancer imaging, in vivo cell tracking and inflammation imaging. In certain embodiments, MPI is a linear shift-invariant imaging system with an analytic point spread function. Some aspects of the present disclosure include a fast image reconstruction method that obtains the intrinsic MPI image with high SNR via gridding the detected signals in x-space. In some instances, methods are provided to reconstruct large field of view (FOV) images using partial field-of-view scanning, despite the loss of first harmonic image information due to direct feedthrough contamination. In some cases, aspects include a multi-dimensional x-space MPI. For example, MPI in accordance with embodiments of the present disclosure find use in cell imaging and cell tracking, such as cancer cell imaging. Magnetic particles may be associated with a specific binding pair member (e.g., an antibody) that specifically binds to an antigen (e.g., an antigen expressed on cancer cells). After administration of the magnetically labeled specific binding pair member to a subject, the subject may have an MPI image taken of various areas within the subject to determine the location of the magnetic particles in the subject. The location of the magnetically labeled particles in the subject may be indicative of specific binding between the specific binding pair member (e.g., the antibody) and its complementary target (e.g., an antigen), which in turn may be indicative of the presence and location of cells that express that antigen in the subject.

In certain embodiments, MPI in accordance with embodiments of the present disclosure uses the nonlinear magnetic characteristics of iron oxide nanoparticles to generate an image whose resolution depends on the magnetic properties of the nanoparticle and the magnitude of the localizing magnetic field gradient. In certain embodiments, the spatial resolution of MPI is finer than the wavelength of the electromagnetic fields used to interrogate the magnetic nanoparticles. In some cases, MPI uses no ionizing radiation and has high tracer imaging contrast since there is no background signal from tissue because tissue is transparent to low frequency magnetic fields.

Magnetic particle imaging (MPI) in accordance with the embodiments of the present disclosure finds use in applications where time resolved imaging is desired. By time resolved imaging is meant that signals from magnetic particles can be acquired and processed into a plurality of images over a period of time. As such, the image produced by a magnetic particle imaging device as disclosed herein may be a time resolved image, where the image includes a plurality of images of the magnetic particles in the sample over a period of time. Time resolved imaging may facilitate the observation of changes in magnetic particle density in different areas of a sample over time. For example, angiography may involve the detection of a plurality of magnetic particle images over time. Analysis of a plurality of magnetic particle images over time may facilitate the observation of the flow of the magnetic tracer through blood vessels over time. Other embodiments of time resolved magnetic particle imaging may find use in the detection and/or tracking of cells (e.g., cancer cells) in a subject. For example, after administration of a magnetically labeled specific binding pair member, as described above, a plurality of MPI images may be taken of the subject, and the location of the magnetically labeled binding pair member may be tracked over time. Aggregation of the magnetic particles at a particular location in the subject over time may be indicative of the presence of the specific target bound by the magnetically labeled specific binding pair member, and thus may be indicative of the presence of cells that express that antigen at that location.

Magnetic particle imaging (MPI) in accordance with the embodiments of the present disclosure finds use in applications such as interventional radiology (also known as vascular and interventional radiology, or image-guided surgery or surgical radiology). Interventional radiology involves the use of minimally invasive procedures performed using image guidance. Magnetic particle images may be used to direct interventional procedures, which are usually done with needles and narrow tubes such as catheters. The magnetic particle images provide images that may allow an interventional radiologist to guide instruments through the subject to the areas containing disease. In certain instances, magnetic particle imaging may minimize physical trauma to the subject by allowing an interventional radiology procedure to be performed on the subject, rather than a typical surgical procedure. In addition, the use of magnetic particle imaging in interventional radiology may facilitate a reduction in infection rates and recovery time for the subject.

The following examples are put forth so as to provide those of ordinary skill in the art with a complete disclosure and description of how to make and use the embodiments disclosed herein, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

One-Dimensional X-Space Formulation of the Magnetic Particle Imaging Process

MPI can be understood as a x-domain process approached as a one-dimensional system, solving for the point spread function, bandwidth requirements, signal to noise ratio, a method for one-dimensional reconstruction, specific absorption rate, magneto-stimulation limits, and conditions for the construction of real instrumentation.

I. Fundamental Relations of MPI in One Dimension

Figure 14:
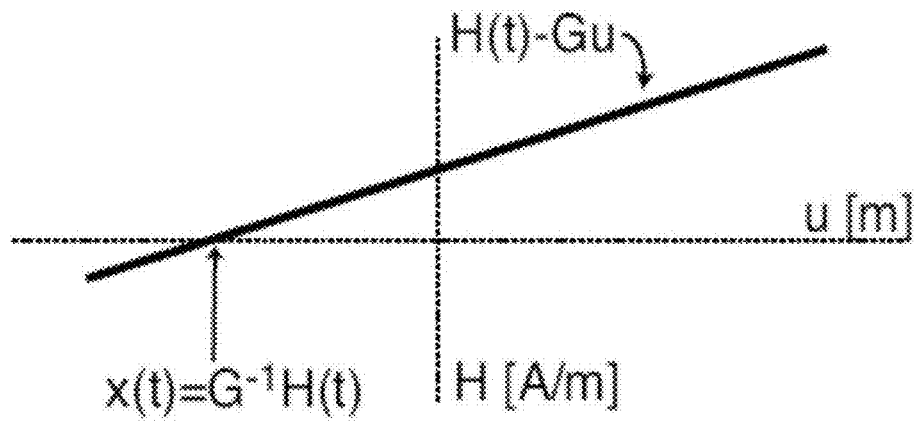
FIG. 14 shows a graph illustrating that addition of time varying homogeneous offset field H(t) to a gradient field −Gu causes a shifting of the field free region x(t), according to embodiments of the present disclosure. For a gradient −G, the location of the FFR can be solved for as $x(t)=G^{-1}H(t)$.

A one-dimensional MPI system may be represented by a linear gradient $-G$ [A/m/m] and a timechanging offset field $H_{shift}(t)$ [A/m] such as what would be created by a Helmholtz coil (FIG. 14). If the gradient is zero at the origin, the magnetic field at position u is as follows:

$$H(u,t)=H_{shift}(t)-Gu$$

Fundamentally, MPI relies on the rapid movement of a field free point across the sample to elicit a signal. The location of that field free point (FFP) can be represented by solving the above equation for $H(x; t)=0$. This yields:

$$x(t)=G^{-1}H_{shift}(t)$$

Substituting FFP position x(t), the magnetization at position u can be rewritten:

$$H(u,x(t))=G(x(t)-u)$$

The magnetization M of a single magnetic nanoparticle in response to an applied magnetic field in one dimension may be described by the Langevin equation:

$$M(H)=m\rho \mathscr{L}[kH]$$

where m [Am^2] is the magnetic moment of the magnetic nanoparticle, k [m/A] is a property of the magnetic nanoparticle, H is the applied magnetic field, and $\rho$ [particles/m$^3$] is the nanoparticle density. By using the Langevin function, certain assumptions may be made. It may be assumed that the system responds whereby the total magnetic field instantaneously aligns with the applied magnetic field (i.e., no particle relaxation). It may also be assumed that there is no perturbation to the local magnetic field from nearby particles or E&M properties such as paramagnetism. Last, it may be assumed that the particles obey the DC Langevin curve at RF and LF frequencies. Now consider an available magnetization density that is a continuous distribution of magnetic nanoparticles, $\rho(u,v,w)$. If is assumed that the nanoparticle distribution is distributed along the x axis and zero elsewhere, then $\rho(u)\triangleq \rho(u,0,0)$. Thus, the magnetization at a single point u along this continuous distribution when the FFP is at position x(t) is:

$$M(H)=M(u,x(t))=m\rho(u)\mathscr{L}[kG(x(t)-u)]$$

Figure 15:
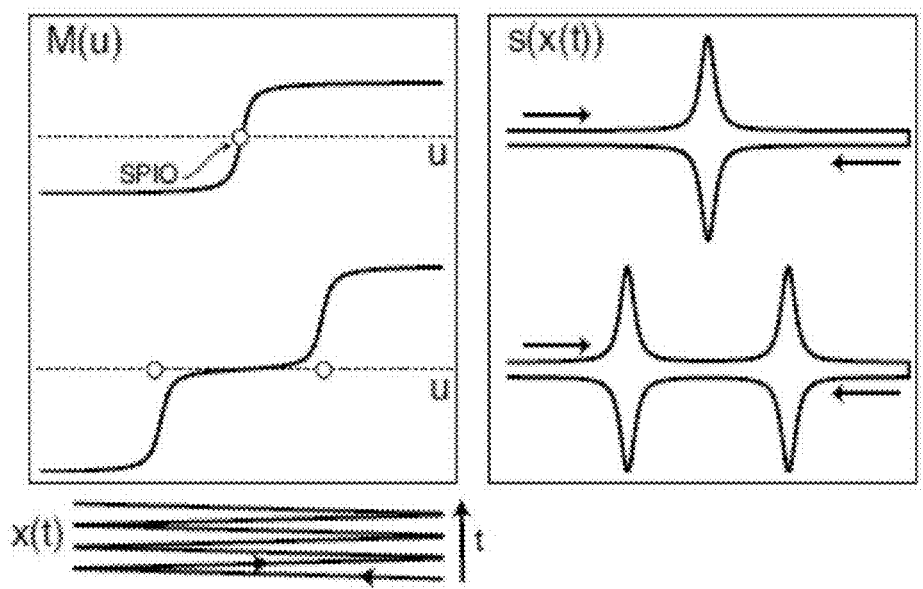
FIG. 15 shows a graph of the magnetization of the system when the FFP is at location x and SPIO nanoparticles positioned at the small circles (left), according to embodiments of the present disclosure. The magnetization is shown for one particle and with two particles. Signal produced by the magnetization when rapidly scanning the FFP back and forth with trajectory x(t) is shown in the graph on the right. The signal is shown graphed against the position of the FFP. The signal changes in sign when the FFP is scanning in the opposite direction.

This one-dimensional magnetization can be converted into a flux, $\Phi$, that would be detected by an inductive detector with $-\sigma$[T/A] sensitivity. Assuming the magnetization density only changes along u results in a convolution:

$$\Phi(t) = -\sigma m \int\int\int \rho(u)\mathscr{L}[kG(x(t)-u)]dudvdw$$

$$= -\sigma m \rho(u) \otimes \mathscr{L}[kGu]|_{u=x(t)}$$

where the u, v, and w axes correspond to the physical x, y, and z axes. The total magnetization in the system is a convolution of the magnetic particle density with a Langevin function kernel. This assumes that the Magnetic nanoparticles do not change the H field significantly. This is generally true since the average χ of magnetite at physiologic concentrations is small. However, the point spread function of a 1D MPI system may not be the Langevin function. The MPI signal may be received using an inductive detector that only sees changing magnetic fields. Visually described in FIG. 15, the MPI 1D signal equation may be derived in volts, s(t):

$$s(t) = -\frac{d\Phi}{dt} = \sigma m \rho(u) \otimes \mathscr{L}'[kGu]|_{u=x(t)} kGx'(t) \quad (\text{II.1})$$

For an image, a magnetic particle distribution convolved with a Point Spread Function (PSF) may be needed. The derivative of the Langevin curve may be assigned to be the system PSF. The extra terms may be divided out, resulting in the MPI 1D image equation:

$$IMG(x(t)) = \frac{s(t)}{\sigma m k G x'(t)} \quad (\text{II.2})$$

$$= \rho(u) \otimes \mathscr{L}'[kGu]|_{u=x(t)}$$

Figure 16:
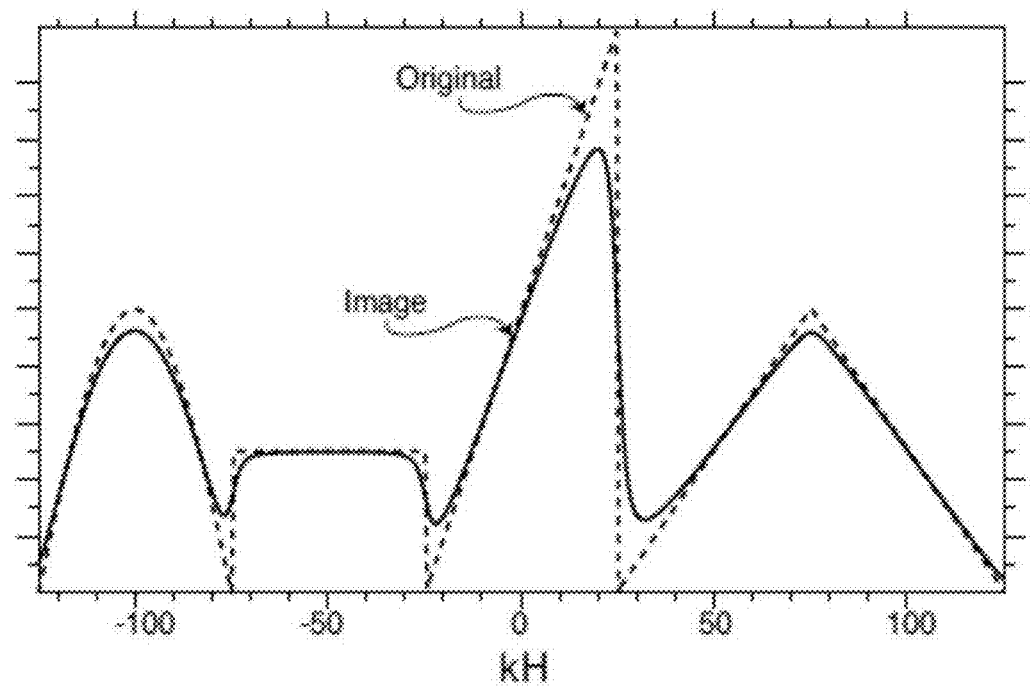
FIG. 16 shows a graph of a simulated MPI 1D image of a complex phantom (solid line) and the source distribution (dotted line), according to embodiments of the present disclosure.

A simulated one-dimensional image that was reconstructed using this method is shown in FIG. 16. MPI is a Linear, Space Invariant (LSI) system.

II. The Langevin Equation

The Langevin function accurately describes the magnetization of an ensemble of magnetic nanoparticles in response to an applied magnetic field. For N nanoparticles, each with magnetic moment m, the magnetization as a function of applied field, H, is:

$$M(H) = Nm\mathscr{L}(kH)$$

$$= Nm\left(\coth(kH) - \frac{1}{kH}\right)$$

where $$k = \frac{\mu_0 m}{k_B T}$$

and kB is Boltzmann's constant, T is the temperature, $\mu_0$ is the vacuum permeability. The equation $$m = M_{sat}\frac{\pi}{6}d^3$$

gives the magnetic moment of a spherical nanoparticle. For magnetite SPIO nanoparticles, $M_{sat} \approx 0.6$ T/$\mu_0$. The derivative of the Langevin function is a well behaved even function:

$$\mathscr{L}'[kH] = Nm\left(\frac{1}{(kH)^2} - \frac{1}{\sinh^2(kH)}\right)$$

The kH product is a dimensionless value. In SI units, k has units of [m/A] with example values shown in the following table. The table assumes round particles.

| diameter (nm) | k = $\mu_0 m/k_B T$ (m/A) |
|---|---|
| 15 | 0.26 × 10$^{-3}$ |
| 20 | 0.61 × 10$^{-3}$ |
| 25 | 1.19 × 10$^{-3}$ |
| 30 | 2.05 × 10$^{-3}$ |
| 40 | 4.86 × 10$^{-3}$ |
| 50 | 9.49 × 10$^{-3}$ |

For a spherical particle, k increases eight times when doubling the particle diameter since k scales as the volume of the nanoparticle. Operating at reduced temperatures, such as 77K or 5K, may increase k and the resulting resolution.

III. Spatial Resolution

From the image equation (Eq. II.2), the point spread function of the MPI process is the derivative of the Langevin function. Solving for the Full Width at Half Maximum (FWHM) of this function, the intrinsic resolution of the MPI process may be estimated analytically as FWHM$_L \approx 4.16$. This gives:

$$FWHM_x \approx G^{-1}\frac{4.16}{k} \approx \frac{4k_B T}{Gm} [m]$$

Figure 17:
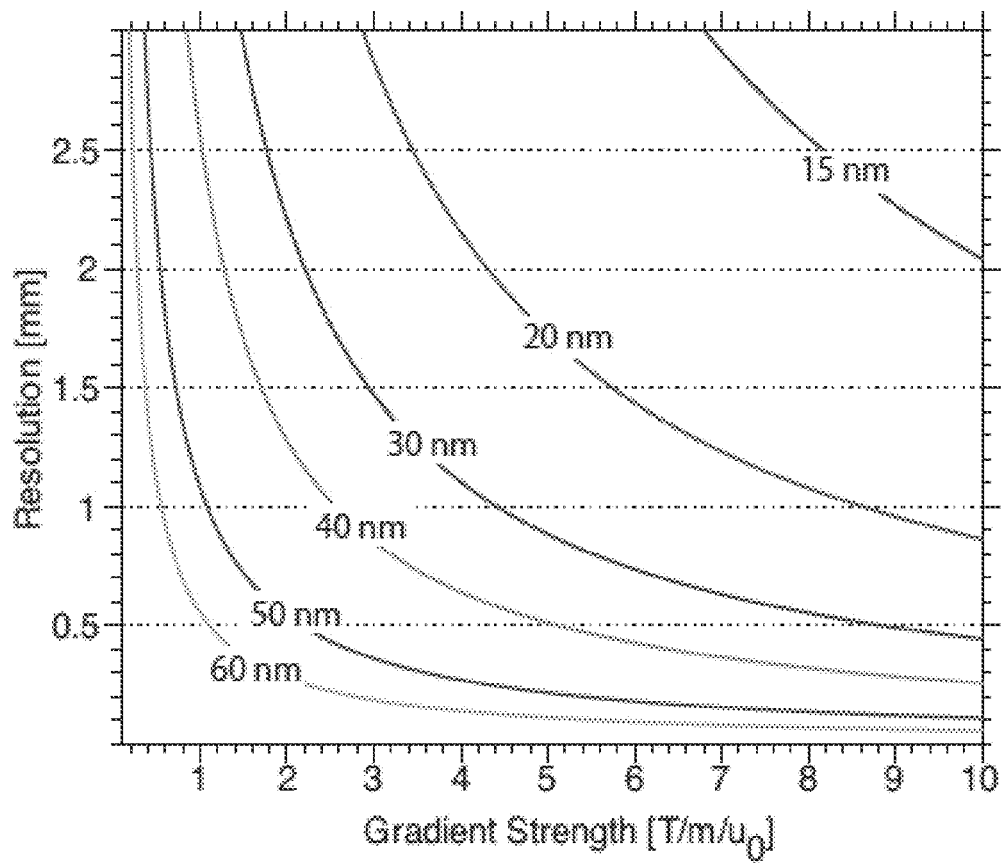
FIG. 17 shows a graph of intrinsic MPI resolution for various nanoparticle diameters when imaged using different gradient field strengths, according to embodiments of the present disclosure.

This implies that MPI resolution is proportional to the thermal energy divided by $\mu_0$m. Resolution may be increased by changing the properties of the magnetic nanoparticles, k, or by increasing the gradient G. For a spherical particle, $$m = \frac{\pi}{6}M_{sat}d^3$$

where d is the particle diameter. The intrinsic resolution of the 1D MPI process may be calculated as a function of gradient strength and particle size (FIG. 17 and Table I). Because of the cubic dependence of linear spatial resolution with magnetic nanoparticle diameter, it may be possible to use a large particle with resistive magnets. This may enable adjusting the intrinsic resolution of the system in real time by changing the strength of the gradient.

TABLE I

Resolution for given particle sizes and gradient strengths. Larger core diameters enable significantly improved resolution. A 5.1 T/m magnetic field gradient is reasonable to build for small animals.

| particle size | gradient strength ($\mu_0$G) | | |
|---|---|---|---|
| (nm) | 1.3 T/m/$\mu_0$ | 2.6 T/m/$\mu_0$ | 5.1 T/m/$\mu_0$ |
| 15 | 16 mm | 7.9 mm | 4.0 mm |
| 20 | 6.6 mm | 3.3 mm | 1.7 mm |
| 25 | 3.4 mm | 1.7 mm | 0.86 mm |
| 30 | 2.0 mm | 1.0 mm | 0.50 mm |
| 40 | 0.83 mm | 0.41 mm | 0.21 mm |
| 50 | 0.42 mm | 0.21 mm | 0.11 mm |

IV. Bandwidth

To design a MPI system, the bandwidth requirements to achieve the desired resolution may be determined. The bandwidth required to represent the Langevin function derivative may be approximated through Fourier analysis.

The derivative of the Langevin function is the PSF and defines the intrinsic resolution of the 1D MPI process. The derivative of the Langevin function may not have a simple Fourier transform, and so may be approximated with a Lorentzian. To reasonable accuracy of <2% peak error, the derivative of the Langevin function by a Lorentzian function may be approximated with FWHM $\xi \approx 4$.

$$\zeta(kH) = \frac{2}{\pi} \frac{2}{4 + (kH)^2}$$

The maximum slew rate of a triangular, sinusoidal, or arbitrarily changing FFP position may be modeled as a linearly changing FFP position. A linearly ramping field with ramp rate R[m/s] gives a time varying position x(t)=Rt. This corresponds to a time varying magnetic field of:

$$H(t) = Gx(t)$$
$$= RGt$$

The magnetic field slew rate, RG, is the product of the scanning rate and the gradient size with SI units A/m/s. In certain cases, RG governs a number of important parameters including bandwidth requirement, SAR, and magnetostimulation.

For N particles located at the origin, $\rho(x)=N\delta(x)$, the 1D signal equation II.1 and substituting a Lorentzian for the derivative of the Langevin curve gives:

$$s(t) = \sigma NmkRG\mathscr{L}'[kRGt] \approx \sigma NmkRG\zeta(kRGt)$$

Taking the Fourier transform of s(t) yields:

$$S(\omega) \approx \sigma Nm\sqrt{\frac{2}{\pi}} \exp\left(-\frac{2|\omega|}{kRG}\right)$$

which describes the frequency content of the MPI experiment. $\omega \geq 0$ since the MPI signal occurs at baseband and does not have a carrier frequency.

For a simpler representation of required bandwidth, the −3 dB bandwidth may be solved for in Hertz:

$$F_{3dB} = \frac{kRG\ln(2)}{4\pi}$$
$$= \frac{M_{sat}d^3 RG\ln(2)}{24}$$

The MPI's bandwidth requirements increase linearly with nanoparticle properties k, gradient strength G, and scanning rate R. Evaluating the FWHM for realistic parameters (R≈2400 [m/s], G=3:25=$\mu_0$ [A/m/m], k=2×10$^{-3}$ [m/A]) that correspond to a particle with diameter d=30 nm, FOV=3 cm, and a sinusoidal excitation of $f_0$=25 kHz results in a $F_{3\ dB}$≈680 kHz. The relationship between the particle size, the intrinsic resolution, and the $F_{3\ dB}$ bandwidth is shown in Table II. In some instances, the particle determines the resolution and required bandwidth.

Since a real imaging system has a finite bandwidth, the received signal may depend on the receive bandwidth of the receiver subsystem. For example, for receive bandwidth 4f and a brick-wall filter, the received signal in Fourier and real space is:

$$S_{LPF}(\omega) \approx \sigma Nm\sqrt{\frac{2}{\pi}} \exp\left(-\frac{2|\omega|}{kRG}\right) rect\left(\frac{1}{4\pi}\frac{|\omega|}{\Delta f}\right)$$

$$s_{LPF}(t) \approx \sigma NmkRG\mathscr{L}'[kRGt] \otimes 2\Delta f \text{sinc}(2\Delta ft)$$

Figure 18A:
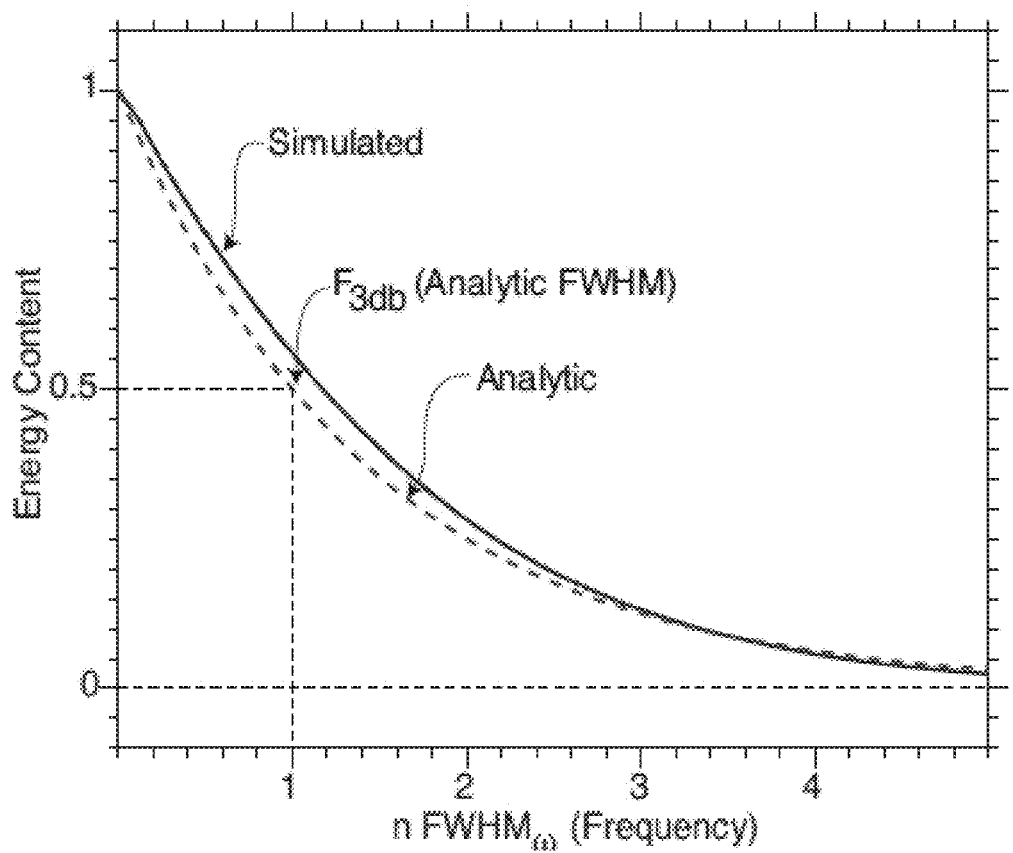
FIG. 18A shows a graph of the relationship between bandwidth and resolution assuming a brick-wall receive filter, according to embodiments of the present disclosure. The intrinsic resolution of the MPI process may be 150% of the theoretically possible resolution when the receiver bandwidth is $\Delta f_{1.5} \approx 2.2\ F_{3\ dB}$. 110% of the intrinsic resolution is not reached until $\Delta f_{1.1} \approx 3.8\ F_{3\ dB}$.
Figure 18B:
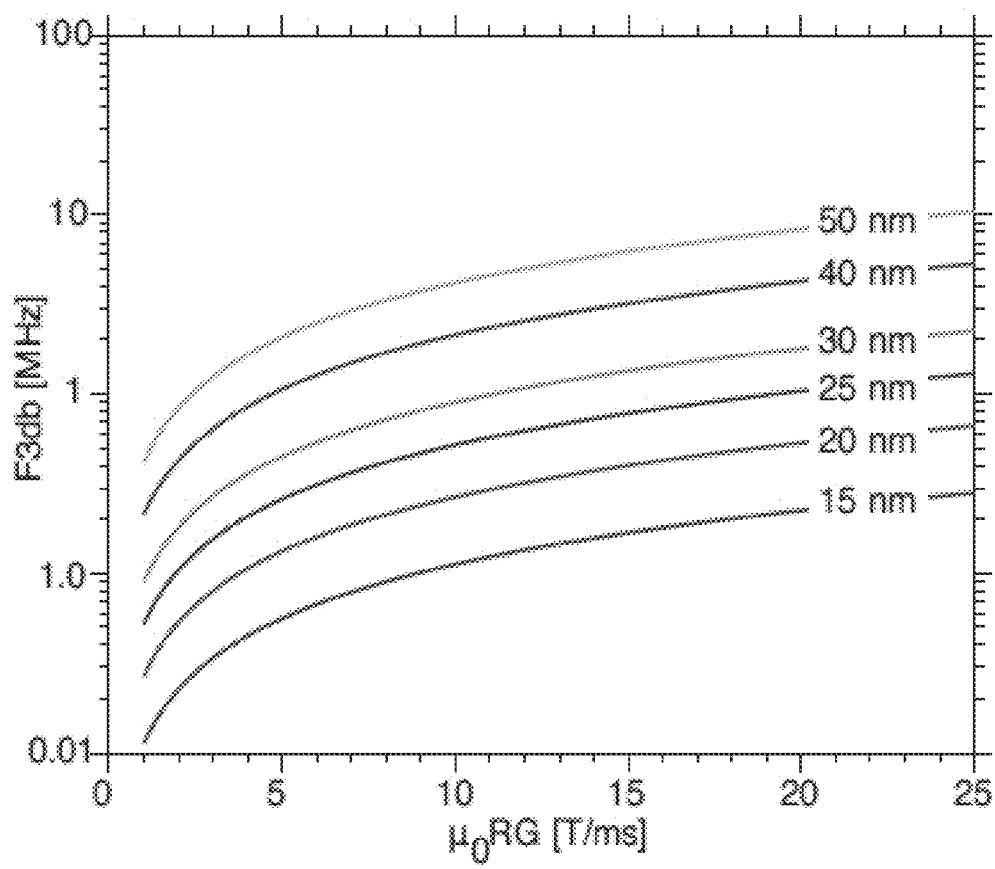
FIG. 18B shows a graph of the linear relationship between $F_{3\ db}$ bandwidth for various particle sizes and magnetic field slew rate, according to embodiments of the present disclosure.

This implies that limiting the bandwidth in frequency space with a filter may cause widening of the point spread function and ringing in the real domain. With these bandwidth requirements, the receive bandwidth may be matched with the fundamental resolution of the system. For example, choosing a bandwidth whose FWHM is the same as the intrinsic resolution of the system may halve the achievable resolution of the system when measured as the FWHM of a point source (FIG. 18A). From the graph, the intrinsic resolution is approached asymptotically. 150% of the intrinsic resolution is not reached until the receiver bandwidth is $\Delta f_{1:5}\approx 2.2\ F_{3\ dB}$, and 110% of the intrinsic resolution is not reached until $\Delta f_{1:1}\approx 3.8\ F_{3\ dB}$.

TABLE II

Resolution and Bandwidth Scaling with respect to the particle size. The values are normalized to a 30 nm particle. Smaller particles have lower bandwidth requirements and poorer resolution.

| particle size (nm) | resolution (mm) | $F_{3dB}$ (MHz) |
|---|---|---|
| 15 | 7.9 | 0.13 |
| 20 | 3.4 | 0.30 |
| 25 | 1.7 | 0.58 |
| 30 | 1.0 | 1.0 |
| 40 | 0.42 | 2.4 |
| 50 | 0.22 | 4.6 |

V. Signal to Noise Ratio

The maximum signal and noise may be calculated from first principles. From the MPI Signal Equation (Eq. II.1), the peak received signal for a linearly ramping magnetic field in volts is:

$$s_{max} = \frac{\sigma NmkRG}{3}$$

The received noise may be from three sources, the noise figure of the preamplifier, NF, the noise from the receive coil, $R_{coil}$, and body noise, $R_{body}$. Since the received signal is typically at a higher frequency than 1/f noise present in semiconductor preamplifiers, the body and coil noise may be modeled as spread across a noise bandwidth, $\Delta f$. Then, assuming Boltzmann noise, the standard deviation of the resistive voltage noise after the preamplifier is:

$$\langle n \rangle = NF\sqrt{4k_B \Delta f(T_{coil}R_{coil} + T_{body}R_{body})} \approx NF\sqrt{4k_B \Delta f T_{coil}R_{coil}}$$

which can be simplified by assuming coil noise dominance. If it is assumed that the bandwidth limitations increase the intrinsic FWHM of the imager by approximately half, the bandwidth requirements may be expressed as a function of the 3 dB bandwidth: $\Delta f = 2 F_{3\ dB} = kRG\ln(2)/(2\pi)$. Then, the Signal-to-Noise ratio (SNR), which was defined as the peak signal divided by the standard deviation of the noise is:

$$SNR_{1D} = \frac{s_{max}}{\langle n \rangle}$$

$$= \frac{\sigma NmkRG}{3NF\sqrt{4k_B \Delta f(T_{coil}R_{coil})}}$$

$$\approx \frac{\sigma Nm}{3NFk_B T_{coil}} \sqrt{\frac{\pi \mu_0 mRG}{2\ln(2)R_{coil}}}$$

which assumes the nanoparticles are at the coil temperature, $T_{coil}$. This describes the SNR for a single pass across the sample, and does not take into account time averaging or acquisition time.

A. 3D Signal to Noise Ratio with Averaging

The signal to noise ratio may be normalized to scan time to take averaging into account. If it is assumes a regular sampling of the field of view with readout in the x direction and acquisition of Ny and Nz lines in the y and z directions, respectively, during a total sampling time of Ts, the number of averages may be estimated as:

$$N_{avg} = \frac{RT_S}{FOV_x N_y N_z}$$

Then, the three dimensional SNR can be estimated:

$$SNR_{3D} \approx \frac{\sigma \kappa NmR}{3NFk_B T_{coil}} \sqrt{\frac{\pi \mu_0 mRG}{2\ln(2)R_{coil}} \frac{T_S}{FOV_x N_y N_z}} \quad (VI.1)$$

and as a function of particle diameter for a spherical particle:

$$SNR_{3D} \approx \frac{\sigma \kappa N\pi^2 d^{9/2} M_{sat}^{3/2} R}{36NFk_B T_{coil}} \sqrt{\frac{\mu_0 G}{3\ln(2)R_{coil}} \frac{T_S}{FOV_x N_y N_z}} \quad (VI.2)$$

where $\kappa \geq 1$ arises from the increased SNR due to the contribution of receiver coils in multiple axes. The signal increases linearly with the scanning rate as faster scanning not only increases the raw signal, but also increases the number of averages possible. The SNR increases with greater time averaging, Ts, and decreases with increasing field of view size. This does not take into account the increased resistance of the body as the frequency is increased since $R_{body} \propto \phi^2$, however at the low frequencies used, MPI is typically in a coil-noise dominated regime.

In some cases, increasing the particle diameter (Eq. VI.2) increases the signal as $SNR \propto d^{9/2}$. This may also reduce the required gradient magnitude required for the same resolution. In certain embodiments, increasing the saturation magnetization, $M_{sat}$, of the magnetic nanoparticles will also enhance SNR. The saturation magnetization may be changed by changing the magnetic materials used.

System modifications can also increase the signal to noise ratio. In certain embodiments, SNR increases with gradient strength, the FFP speed, reducing coil noise, and improvement of the preamplifier noise figure. In some instances, MPI's SNR increases as the scanning speed is increased, even though the bandwidth requirements also increase. In some cases, reducing the gradient strength, G, also increases SNR for a fixed sample size because the scanning rate can be increased while maintaining the same magnetic field slew rate.

From Equation VI.1, the SNR may be estimated for various scenarios in Table III. The calculations are made for specific applications with well defined fields of view and resolutions at the SAR limit assuming a single receive coil and sensitivity and noise values. For a small animal, the actual coil sensitivity value may be assumed to be $\sigma=150$ uT/A and a noise of $\langle n \rangle =100$ pV. For a human scanner $\sigma=1.4$ μT/A and $\langle n \rangle =1.8$ pV. In certain embodiments, MPI should detect a single nanogram or less of magnetic material with reasonable SNR. These sensitivity numbers are similar to those calculated in a simulation study on the optimal SPIO core diameter for MPI imaging.

TABLE III

Theoretical $F_{3dB}$, SAR and SNR, and detection limit for Real-Time (RT) and High Resolution (HR) scans for d = 30 nm particles at the SAR limit of 4 W/kg. Note that we require at least BW = 2:2 $F_{3dB}$ to achieve 150% of the intrinsic resolution.

| Description | R [m/s] | $G_{max}$ [T/m/μ$_0$] | FOV [cm] | Intrinsic Resolution [mm] | Time [s] | diameter [cm] | 2.2 $F_{3dB}$ [kHz] | SNR 1 ng Fe |
|---|---|---|---|---|---|---|---|---|
| heart (RT) | 1150 | 1.3 | 20 | 2 × 4 × 4 | 1/5 | 34 | 297 | 0.07 |
| heart (HR) | 577 | 2.6 | 20 | 1 × 2 × 2 | 30 | 34 | 297 | 0.3 |
| brain (HR) | 1115 | 2.6 | 18.4 | 1 × 2 × 2 | 60 | 18.4 | 574 | 1.0 |
| extremity (HR) | 1461 | 2.6 | 14 | 1 × 2 × 2 | 60 | 14 | 752 | 1.9 |

TABLE III-continued

Theoretical $F_{3dB}$, SAR and SNR, and detection limit for Real-Time (RT) and High Resolution (HR) scans for d = 30 nm particles at the SAR limit of 4 W/kg. Note that we require at least BW = 2:2 $F_{3dB}$ to achieve 150% of the intrinsic resolution.

| Description | R [m/s] | $G_{max}$ [T/m/$\mu_0$] | FOV [cm] | Intrinsic Resolution [mm] | Time [s] | diameter [cm] | 2.2 $F_{3dB}$ [kHz] | SNR 1 ng Fe |
|---|---|---|---|---|---|---|---|---|
| mouse (RT) | 6769 | 2.6 | 2.5 | 1 × 2 × 2 | 1/250 | 3 | 3482 | 1.9 |
| mouse (HR) | 3451 | 5.1 | 2.5 | 0.5 × 1 × 1 | 60 | 3 | 3482 | 82 |

VI. Sinusoidal Excitation

In certain embodiments, a MPI system excites the sample with a triangular excitation waveform. In some cases, since a triangular excitation field would be composed of a sum of odd harmonics, a simple sinusoid that has limited frequency content may be used as the excitation waveform.

In some cases, geometric isolation is performed. Geometric isolation may reduce coupling between the transmit and receive coils by putting the receive coil in a gradiometer configuration. This may also reduce coupled noise from outside the system bore. In some instances, a conductive sample in the bore induces eddy currents that induce a signal in the receive coil.

In certain embodiments, isolation between the transmit and receive coils is performed using a combination of passive notch and high-pass filters. The combination may achieve million-fold or more reduction in the excitation frequency from the received signal. In some instances, with a sinusoidal excitation, the SNR decreases near the edges of the scan volume because of the reduced magnetic field slew rate.

VII. Specific Absorption Rate

For a sinusoidally oscillating magnetic field, SAR in can be analytically estimated for a cylinder as:

$$P = \frac{\pi^2 f_1^2 B_1^2 D^2}{8\rho s}$$

where $f_1$ is the excitation frequency, $B_1$ is the excitation magnitude, D is the diameter of the sample, p is the tissue resistivity at the excitation frequency, and s is the specific gravity of the sample. If it is assumed sinusoidal excitation and a field of view, the excitation magnitude and frequency may be estimated as:

$$B_1 = \mu_0 G \frac{FOV}{2}$$

and $$f_1 = \frac{1}{2}\frac{R}{FOV}$$

which implies SAR in terms of scanning rate R and gradient strength G is:

$$P \approx \frac{\pi^2 (\mu_0 RG)^2 D^2}{128\rho s}$$

In some instances, the SAR presented in this manner does not depend on the field of view.

Figure 19:
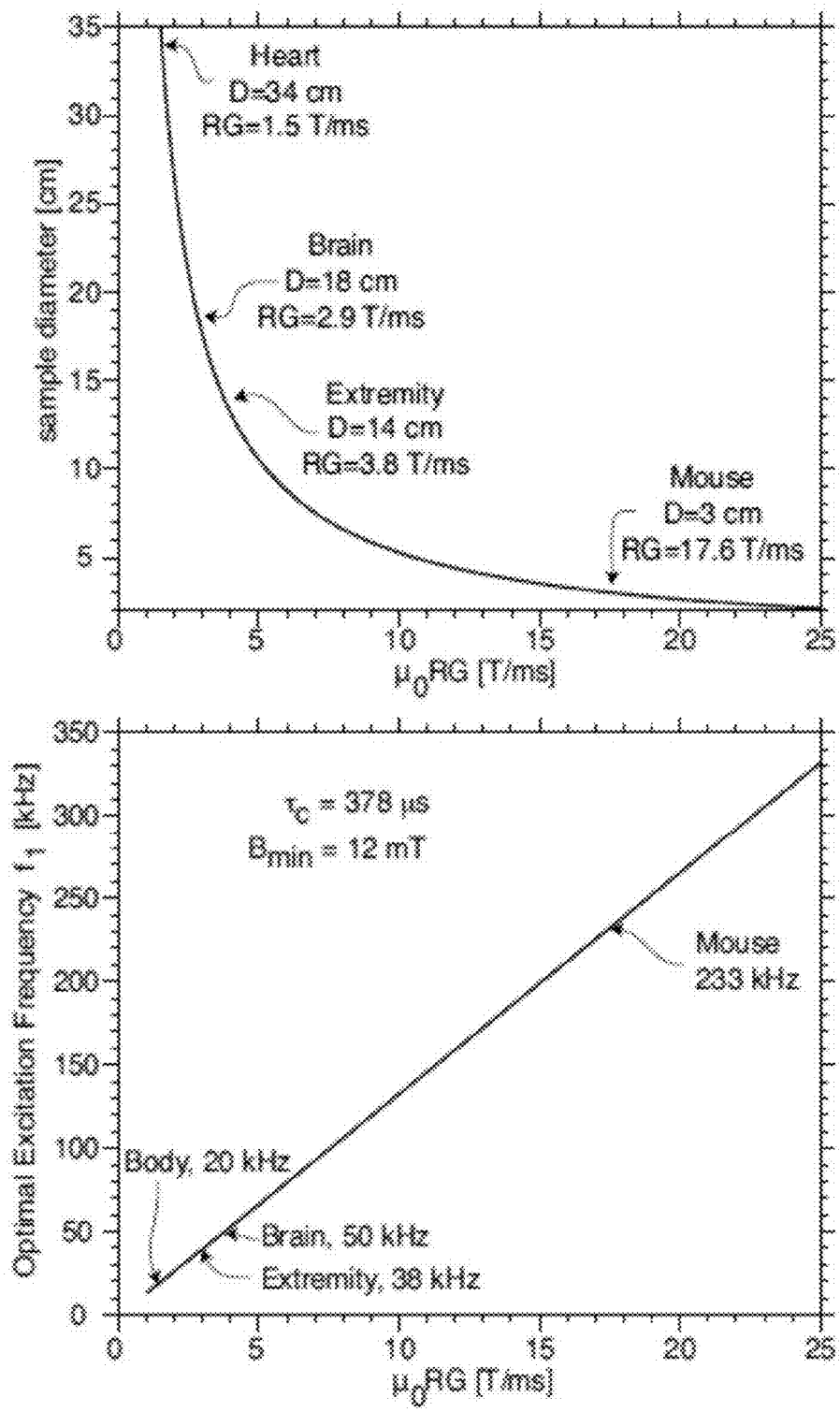
FIG. 19 shows a graph of the maximum magnetic field slew rate for a 4 W/kg Specific Absorption Rate (SAR) (top), according to embodiments of the present disclosure. Optimal scanning frequency at the 4 W/kg RG limit is shown in the bottom graph.

At present, the United States Food and Drug Administration (FDA) limits the Specific Absorption Rate (SAR) deposition in the body to 4 W/kg. The maximum magnetic field slew rate for a given sample size may be solved for. Since SNR increases with the magnetic field slew rate, this relationship may determine the optimal scanning rate. The maximum sample diameter may be a function of magnetic slew rate, as shown in FIG. 19. Large slew rates should be applied to the animal or patient at the lowest possible frequency that does not cause magneto-stimulation.

VIII. Slew Rate, and Magneto-Stimulation

A rapidly changing magnetic field in conductive tissue may induce an electric field that can stimulate peripheral and cardiac nerves. The fundamental law of magnetostimulation states:

$$B_1(\tau) = B_{min}\left(1 + \frac{\tau}{\tau_c}\right)$$

where $B_1(f)$ is the peak amplitude for magnetostimulation as a function of excitation time constant, $\tau$, $B_{min}$ is the minimal peak-to-peak excitation amplitude for frequencies going to infinity, and $\tau_c$ is the chronaxie time constant. This model is similar to both FDA and IEC dB/dt regulations for Magnetic Resonance Imaging scanners.

Because current MPI scanners are constructed using a resonant excitation coil, the minimum sinusoidal excitation frequency to prevent magnetostimulation of the peripheral nerves may be estimated. For a sinusoidal excitation, the excitation rise time may be approximated as:

$$\tau = \frac{1}{2\pi f_1}$$

and so the fundamental law of magnetostimulation with a sinusoidal excitation signal with respect to the desired magnetic field slew rate is:

$$\frac{dB}{dt} = B_{min}\left(2\pi f_1 + \frac{1}{\tau_c}\right)$$
$$= \mu_0 RG$$

Solving for the optimal frequency of excitation for a magnetic field slew rate product while maximizing SNR:

$$f_1 = \frac{\mu_0 RG}{2\pi B_{min}} - \frac{1}{2\pi \tau_c}$$

In certain embodiments, the system may operate with the maximum possible slew rate that does not cause magnetostimulation. Because $\mu_0 RG$ is large compared to the slew rates used in MRI gradients, $B_{min}$ is essentially the magnetic stimulation threshold. That is, $B_1 \approx B_{min}$. For the peripheral nerves, the Z gradient may be estimated in an MRI with $B_{min} \approx 12$ mT for a peak-to-peak excitation magnitude of $B_{pp} = 2B_{min}$ and a chronaxie time constant of $\tau_c \approx 378$ µs.

The optimal excitation frequencies for various sample sizes are shown in FIG. 19. This formulation may be important at lower excitation frequencies as the ratio $1/(2\pi\tau_c)$ 420 Hz. At the maximum magnetostimulation, excitation frequencies to achieve the SAR limited magnetic field slew rate, imaging a human heart can have up to 20 kHz line scan rate. In certain instances, a lower fundamental frequency is easier to filter out because they take a smaller percentage of the available bandwidth. In some cases, imaging at the magnetostimulation limit requires increasing the scanning frequency to prevent stimulation of the peripheral nerves in order to reach the desired magnetic field slew rates.

IX. Experiment 1

Figure 20:
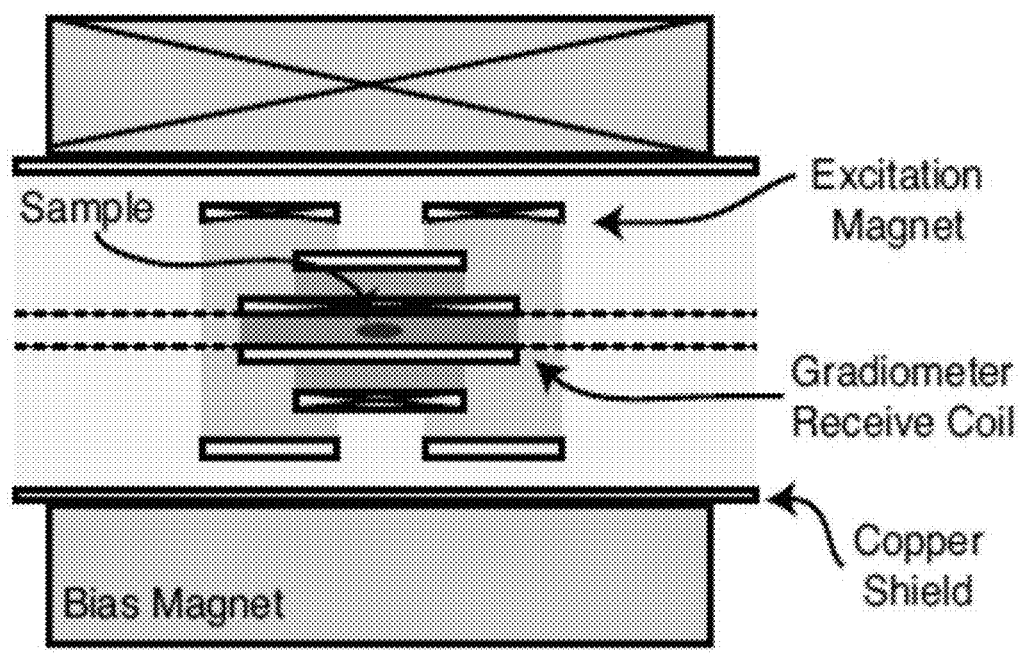
FIG. 20 shows a schematic cross-section of a MPI spectrometer for testing point spread function and bandwidth of the MPI process, according to embodiments of the present disclosure. The excitation magnet generated a 160 mT peak-to-peak oscillating magnetic field at 6.23 kHz. The bias coil supplied a DC magnetic field of up to ±80 mT. The signal received from the gradiometric receive coil was digitized at 1.25 MSPS without filtering.

To test the principles described above, a zero dimensional MPI spectrometer was built as shown in FIG. 20. The system was constructed with a excitation electromagnet and a biasing magnet. The outer electromagnet generated the bias field, $H_{bias}$, which simulated placing a point source sample at location $u = G^{-1} H_{bias}$. Varying the bias field simulated moving the sample in a gradient field. The virtual FFP was scanned using a resonant transmit coil, $H_{shift}$, and the signal produced was received with a gradiometer receive coil. Using the system, the MPI signal was measured from an undiluted SPIO nanoparticle sample (Chemicell 50 nm fluidMAGD, Berlin, Germany). The point spread functions were identical when diluted.

The bias coil was driven by a DC coupled audio amplifier (Crown M-600, Elkhart, Ind., USA) at field up to ±80 mT while dissipating 1 kW. The resonant excitation coil generated 160 mT peak-to-peak at 6.23 kHz and was driven by an audio amplifier (AE Techron LVC5050, Elkhart, Ind., USA) with 5 kW of instantaneous power at a pulsed 1.5% duty cycle. The signal from the receive coil was digitized by a 16-bit data acquisition system with a 1.25 MSPS sampling rate (National Instruments USB-6259, Austin, Tex., USA) controlled by custom software written in MATLAB (Mathworks MATLAB, Natick, Mass., USA).

X. Results

Figure 21A:
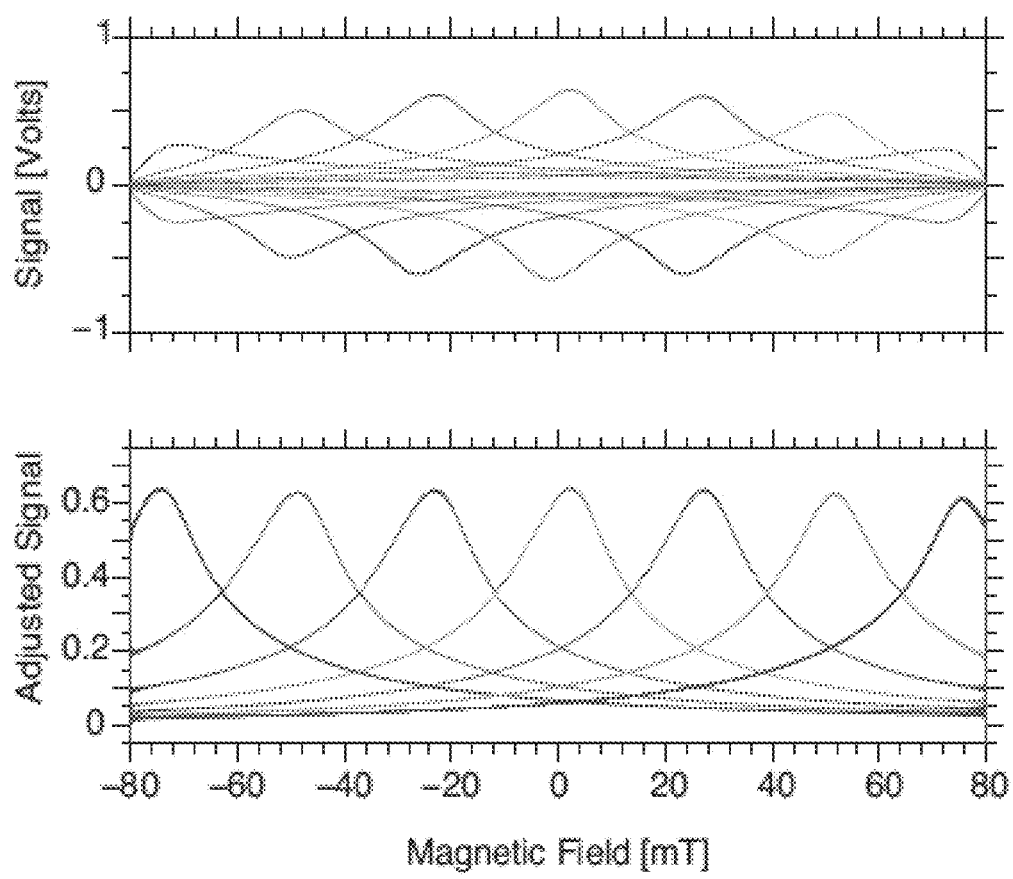
FIG. 21A shows a graph of a parametric plot of FFP position and received signal with multiple offset field strengths (top), according to embodiments of the present disclosure. The peaks corresponded to the offset field generated by the bias coil. Received signal divided by instantaneous FFP velocity is shown in the graph in FIG. 21A (bottom). This is equivalent to the 1D image (see Equation 11.2).
Figure 21B:
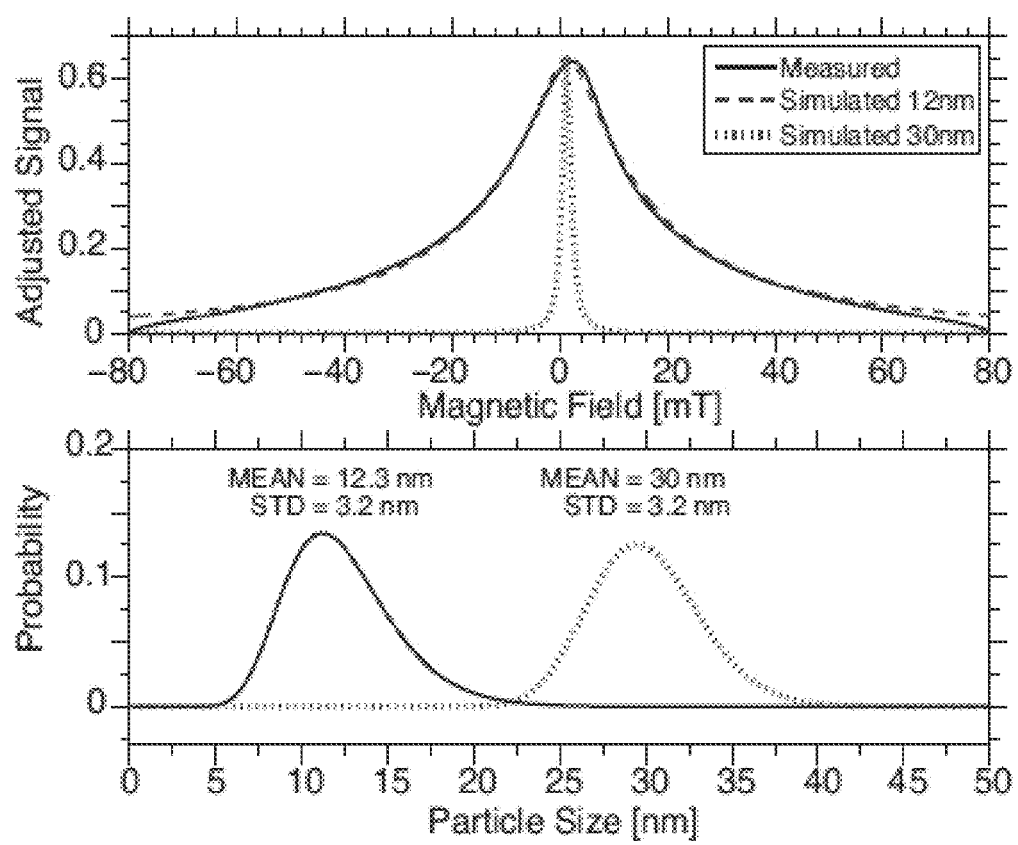
FIG. 21B shows a graph of the measured PSF compared with simulated PSF of a particle distribution, also shown with the point spread function of a hypothetical 30 nm particle (top), according to embodiments of the present disclosure. Log-normal particle size distribution used to generate simulated data is shown in the graph in FIG. 21B (bottom).

In FIG. 21A, the received signal plotted as a function of FFP position is shown. This is similar to the figure shown in FIG. 15. The measured data fit well to theoretical predictions. Normalizing to the relative speed of the FFP position showed that the point spread function did not change across the Field of View (FOV). The magnitude of the magnetic fields used here were beyond the magnetostimulation limit. Large excitation fields were used due to the small core diameters of the SPIO nanoparticles used in this experiment.

The measured point spread function was fit to what would be measured if there was a distribution of nanoparticle diameters. Assuming a log-normal distribution, the mean magnetic core diameter was estimated to be 12.3 nm with a standard deviation of 3.2 nm. This corresponded well to literature values for particles, which measured the core diameter from Resovist (Schering AG) at approximately 15.5 nm.

Multi-Dimensional X-Space Magnetic Particle Imaging

A. MPI Signal Theory

In certain embodiments, the imaging system has Linearity and Shift Invariance (LSI). In some instances, non-LSI systems may be analyzed using standard signals and systems techniques such as convolution. In some cases, imaging systems may use the temporal harmonic domain to analyze the harmonics of the received MPI signal. Nonlinear magnetic nanoparticles respond to a sinusoidal magnetic waveform with harmonic signals at multiples of the excitation frequency. These harmonics are suppressed sufficiently far from the center, or Field-Free-Point (FFP) of a field gradient, since the gradient field leaves the particles in saturation despite the RF excitation. Hence, the gradient field provides a method to localize harmonic response in 3D space. In certain instances, the one-dimensional frequency-space signal can be described using Chebychev polynomials of the second kind convolved with the magnetization density. In certain embodiments, the Chebychev polynomial model is exact in one dimension, but extension to two and three dimensions may be an approximation.

A fundamental assumption of certain harmonic methods is that each pixel is interrogated over several cycles of the RF excitation. In some cases, this may not be accurate for faster scanning methods, where a single pixel is scanned instantaneously only once. In certain embodiments, the imaging system does not require a repeating excitation, thus describing the 1D MPI imaging process as an instantaneous scan through x-space rather than a sinusoidal steady-state harmonic decomposition. In some instances, the 1D x-space formalism can be applied to 2D and 3D.

B. Image Reconstruction in MPI

In certain embodiments, reconstruction techniques in MPI require a pre-characterization of the magnetic nanoparticles whose signal response is formulated into a system matrix. The system matrix may be comprised of Fourier components of the temporal signal for every possible location of a point source. E.g. for an image with $N_x \times N_y \times N_z$ possible points, the total number of elements in the system matrix will be $N = N_x N_y N_x N_c N_f$ where $N_c$ is the number of receive coils and $N_f$ is the number of Fourier components desired for the reconstruction. The system matrix can be measured physically using a nanoparticle sample, or estimated using a model. However, in some cases, the system matrix is specific to the nanoparticle sample, and reconstruction may be depend on whether the nanoparticle behaves differently in tissue, if the system drifts, or if the model is inaccurate. In some instances, reconstruction may be achieved through regularization and matrix inversion techniques such as singular value decomposition or algebraic reconstruction. In certain cases, the solution is regularized to achieve high resolution while not amplifying noise when inverting the system matrix. In some instances, MPI image reconstruction minimizes any loss of SNR.

In certain embodiments, MPI may be analyzed without a system matrix using a narrowband MPI system that images multiple MPI harmonic mixing products and places them on a grid in real-space. In other embodiments, MPI may be analyzed using a theoretical formalism that may be validated with simulation and experiment. In some instances, a fast reconstruction algorithm that computes the MPI image without matrix inversion and without a model based image reconstruction may be used. In these instances, the 1D image reconstruction method may be extended into 2D and 3D.

I. Hypotheses for Multidimensional X-Space Magnetic Particle Imaging

In certain embodiments, reciprocity and linear shift invariant (LSI) imaging systems theory may be used to analyze the 1D MPI signal imaging process. In some instances, it may be assumed that the nanoparticle magnetization instantaneously aligns with the applied local magnetic field. In certain cases, the MPI signal in one dimension is linear and space invariant and can therefore be described as a convolution. In some instances, the Point Spread Function (PSF) is the derivative of the magnetic nanoparticle's Langevin function. This analysis provided estimates for bandwidth requirements, which approach a megahertz for typical imaging parameters. In certain embodiments, the maximum SNR will depend on patient heating, and the maximum (partial) Field-of-View (FOV) will depend on magnetostimulation.

In certain embodiments, one-dimensional x-space MPI theory may be extended into two and three dimensions. In some instances, the magnetic nanoparticles align instantaneously with the local magnetic field and the loss of first harmonic information due to direct feedthrough contamination is recoverable. In certain cases, for multidimensional x-space, the linear 3D gradient field can be written as Gx where G is an invertible matrix so that the gradient field uniquely identifies the location x in 3-space. In some cases, the real-world gradient field is invertible, and 3D MPI is a linear and shift invariant imaging process. In certain instances, the analytic 3D point spread function of MPI may be derived. In some cases, a fast image reconstruction algorithm that requires no calibration measurements or matrix inversion is used, such that the algorithm is both computationally efficient and robust to noise. To apply the x-space formulation to real MPI systems, in some cases, the loss of the fundamental frequency breaks the strict Linear Shift Invariance (LSI) properties. In certain instances, the lost first harmonic information is fully recoverable using robust and noise-free image processing methods. The three hypotheses set forth above are justified in detail below.

Hypothesis 1: The Instantaneous FFP is Uniquely Defined in Space

Figure 22:
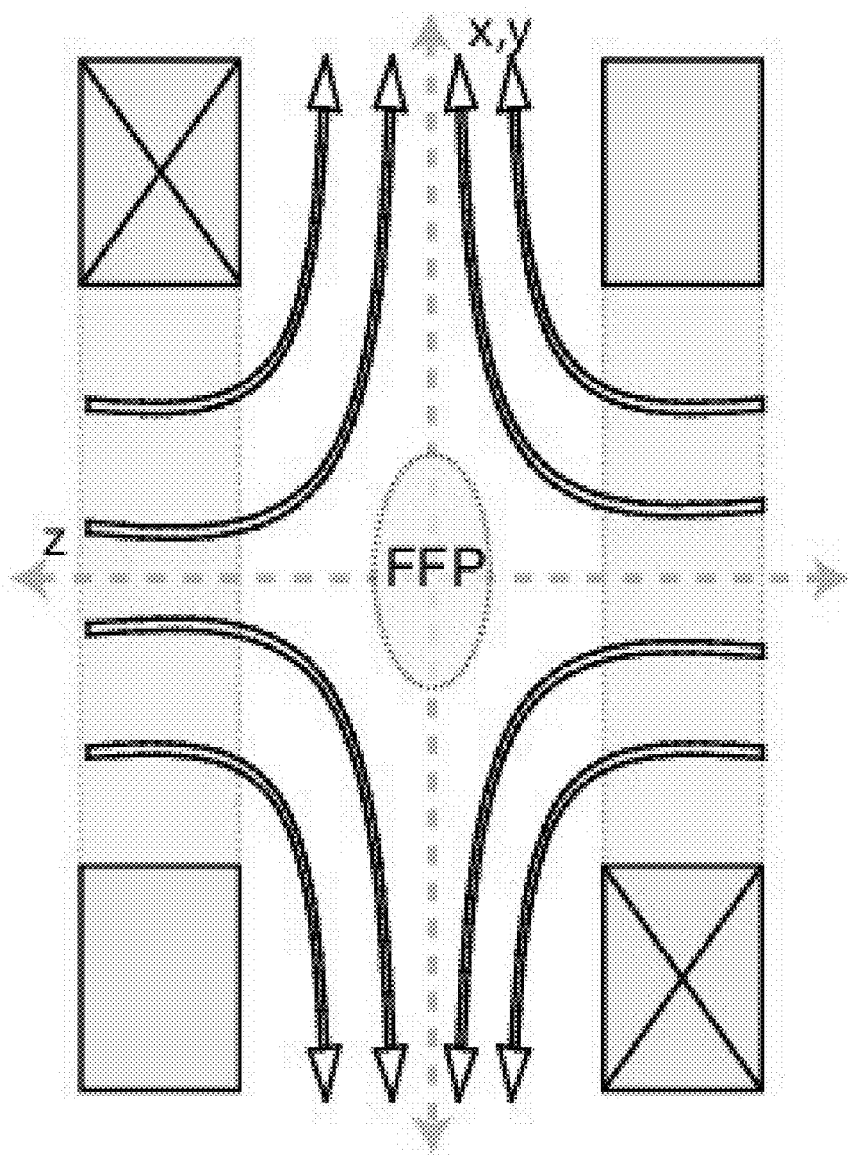
FIG. 22 shows a schematic drawing of two opposing ring magnets with radial symmetry about the z-axis produce a 3D gradient field with a Field Free Point (FFP) at the isometric center, according to embodiments of the present disclosure. The imaging device produced a gradient of 6 T/m in the z-axis, and 3 T/m in the x- and y-axes across a 8.89 cm free bore through the z-axis with linearity.

MPI relies on a 3D linear gradient in the form:

$$H(x) = Gx = \begin{bmatrix} -\alpha G_{zz} & G_{xy} & G_{xz} \\ G_{xy} & (\alpha-1)G_{zz} & G_{yz} \\ G_{xz} & G_{yz} & G_{zz} \end{bmatrix} \begin{bmatrix} x \\ y \\ z \end{bmatrix}$$

where the vector $x=[x\ y\ z]^T$ denotes position in real space, and the parameter $\alpha \in (0,1)$. Note that the trace (G)=0, which is consistent with Maxwell's equations in a source-free space ($\nabla^2 B=0$). For the case of a cylindrically symmetric Maxwell z-gradient, used for all experiments herein (see FIG. 22), $\alpha=\frac{1}{2}$ and the off-diagonal elements are zero. So the gradient matrix G is diagonal:

$$H(x) = Gx = \begin{bmatrix} -\frac{1}{2} & 0 & 0 \\ 0 & -\frac{1}{2} & 0 \\ 0 & 0 & 1 \end{bmatrix} \begin{bmatrix} x \\ y \\ z \end{bmatrix} \quad (\text{II.1})$$

Typical small animal NdFeB Maxwell pair gradient strengths are $\mu_0 G_z \sim 2500$ to 6000 mT/m. MPI spatial resolution is anisotropic and twice as fine in z as in the x and y direction due to this fundamentally anisotropic magnetic field gradient.

In addition to the 3D field gradient, an orthogonal set of homogeneous magnets can be added that produce static and time-varying fields to shift the FFP:

$$H_s(t) = \begin{bmatrix} H_x(t) \\ H_y(t) \\ H_z(t) \end{bmatrix}$$

These homogeneous magnets could be built using Golay coils or Helmholtz coils and these are considered to be accurately modeled as homogeneous over the linear region of the gradient field. Giving the gradient a convenient negative sign, the total field can be described as:

$$H(t,x) = H_s(t) - Gx$$

Solving for the instantaneous location of the FFP, $x_s(t)$, such that $H(t,x)=0$, provided that the G matrix is non-singular:

$$x_s(t) = G^{-1} H_s(t)$$

In certain instances, the G matrix is non-singular for realistic gradient coils. First, consider the Maxwell gradient pair, the design of choice for virtually all experimental work in 3D MPI. In some cases, the diagonal G matrix is always invertible; indeed the $\det(G) = G_{zz}^3 \frac{1}{4}$. For the more general case, assuming cross terms $G_{xy} = G_{xz} = G_{yz} = 0$, the $\det(G) = G_{zz}^3 \alpha(1-\alpha)$ is guaranteed to be non-zero, except for trivial cases. Finally, if we assume only that $G_{xy}=0$, then one can show that $\det(G) = G_{zz}\{\alpha(1-\alpha)G_{zz}^2 + \alpha G_{yz}^2 + (1-\alpha)G_{xz}^2\}$. Since the coefficients $\alpha$ and $1-\alpha$ are guaranteed to be positive, the det(G) is guaranteed positive. Hence, the G matrix is not singular, and there always exists a unique FFP.

The uniqueness of the FFP could be lost if the region of interest includes regions outside the linear region of the gradient coil. Artifacts could occur in such a case, akin to "fold over" artifacts in MRI, where the body extends beyond the monotonic region of the gradient field. Hence, to avoid this challenge, in some cases, it can be assumed that the entire FOV of the MPI scan is within the linear region of the gradient field and also within the homogeneous region of the shifting magnets.

Then, the magnetic field at an arbitrary point x is related to the instantaneous position of the FFP:

$$H(t,x) = G(x_s(t) - x) \quad (\text{II.2})$$

B. Hypothesis 2: Adiabatic Langevin Model

In certain embodiments, the MPI signal is due to the nonlinear response of a Superparamagnetic Iron Oxide (SPIO) nanoparticle to a changing magnetic field. At DC field strengths used in MPI of $B_{max}$<1 Tesla, tissue is largely unaffected by the magnetic field, but a SPIO particle undergoes a nonlinear change in magnetization described by the Langevin theory of paramagnetism. For a density of SPIO nanoparticles, $\rho$[particles/m³], the Langevin equation gives a magnetization density:

$$M(H) = \rho m \mathscr{L}[k\|H\|]\hat{H} \quad \text{(II.3)}$$

where m[Am²] is the magnetic moment of a single magnetic nanoparticle and $\mathscr{L}$ is the Langevin function. The constant of proportionality $k=\mu_0 m/k_b$ T [m/A] is given by the magnetic moment, Boltzmann constant $k_B$ and temperature T. For a spherical particle, the magnetic moment can be computed as $$m = M_{sat}\frac{\pi}{6}d^3,$$

where $\mu_0 M_{sat} \sim 0.6$ T for magnetite and d[m] is the particle diameter.

The vector direction assumes that the magnetic particles align adiabatically and instantaneously with the applied magnetic field, which is strictly true only if the time varying magnetic field is much slower than the particle relaxation time. Neel and Brownian relaxation of the particles will reduce the magnetization and change the phase between the applied magnetic field vector H and the measured magnetic moment M(H). We note that typical Brownian time constants of most magnetic nanoparticles used in MPI are about 1-30 µs whereas typical MPI scanning frequencies are below 25 kHz, so this appears physically realistic. The adiabatic hypothesis is required for strict shift invariance; artifacts from relaxation appear to be mild. This model aims to predict the behavior of ferrofluids to time-varying magnetic fields. This hypothesis may be used in approaches to MPI theory. In certain cases, it can be assumed that the data acquisition dwell time per pixel exceeds the relaxation time constant. As shown in the Experimental section below, the x-space approach generate images consistent with the adiabatic hypothesis.

C. Hypothesis 3: Loss of Low Frequency Information is Recoverable

In MPI, the RF transmit occurs during signal reception. This means that the received signal may be contaminated by direct feedthrough from the source RF coil coupling into the detector, despite efforts at electronic and geometric decoupling. In certain embodiments, MPI imaging methods must be reconstructed only from (uncontaminated) high frequency information. In some instances, the MPI signal equation may be analyzed as if the complete receive bandwidth were available. In some cases, the lost low-frequency information represents the low spatial frequencies (e.g., DC or baseline component) of the image. In certain instances, a smooth and contiguous version of partial-FOV scans over the entire FOV may be reconstructed using robust image processing methods with a small amount of overlap in partial FOV scans. In certain cases, this allows the recovery of the lost baseline information without adding a significant amount of noise.

II. Multidimensional Theory of MPI

For a continuous distribution of magnetic nanoparticles with density $\rho(x)$[particles/m³], from equations 11.2 and 11.3, the magnetization density of $\rho(x)$ nanoparticles located at position x when the FFP is at $x_s(t)$ may written be as follows:

$$M(t,x) = m\rho(x)\mathscr{L}[k\|G(x_s(t)-x)\|]\frac{G(x_s(t)-x)}{\|G(x_s(t)-x)\|} \quad \text{(III.1)}$$

and thus the total dipole moment is obtained by integrating the magnetization across the imaging volume is:

$$m(t) = \int\int\int m\rho(u)\mathscr{L}[k\|G(x_s(t)-u)\|]\frac{G(x_s(t)-u)}{\|G(x_s(t)-u)\|}du$$

This total dipole moment can be written as a spatial convolution interrogated at the instantaneous FFP location:

$$m(t) = m\rho(x) *** \mathscr{L}[k\|Gx\|]\frac{Gx}{\|Gx\|}\bigg|_{x=x_s(t)}$$

For an imaging system using an inductive detector, reciprocity can be used to calculate the received signal. For simplicity, orthogonal receive coils can be assumed to be aligned with the x, y, and z axes of the instrument. Then, the sensitivity of the receive coils, $-B_1(x)$[T/A], would be a matrix of sensitivities. For the case for receive coils in each of the x, y, and z-axes respectively, the sensitivity matrix would be $B_1(x)=[B_{1x}(x) B_{1y}(x) B_{1z}(x)]$. From reciprocity, the received signal vector is:

$$s(t) = \frac{d}{dt}\int\int\int B_1(u)M(t,u)du \quad \text{(III.2)}$$

To evaluate this derivative, the MPI signal equation may be evaluated. We begin by defining r and $\hat{r}$:

$$r \triangleq kG(x_s(t)-x) \qquad \dot{r} = kG\dot{x}_s(t)$$

$$\Rightarrow$$

$$\hat{r} \triangleq \frac{r}{\|r\|} \qquad \dot{\hat{r}} = \frac{\dot{r}}{\|r\|} - \frac{\dot{r}^T r}{\|r\|^3}r$$

$\dot{r}$ can be decomposed into a tangential component, $\dot{r}_\|$, and a normal component, $\dot{r}_\perp = (\dot{r}-\dot{r}_\|)$. Rewriting $\dot{r}$ yields:

$$\dot{r} = \dot{r}_\| + \dot{r}_\perp$$

$$= \left(\dot{r}\cdot\frac{r}{\|r\|}\right)\hat{r} + \left(\dot{r} - \left(\dot{r}\cdot\frac{r}{\|r\|}\right)\hat{r}\right)$$

The derivative of the quasi-static Langevin function with vector-valued, time varying operand r:

$$\frac{d}{dt}\mathscr{L}(\|r\|)\hat{r} = \dot{\mathscr{L}}(\|r\|)\left(\frac{\dot{r}\cdot r}{\|r\|^2}r\right) + \frac{\mathscr{L}(\|r\|)}{\|r\|}\left[\dot{r} - \frac{\dot{r}\cdot r}{\|r\|^2}r\right]$$

can be rewritten as a function of $\dot{r}_\|$ and $\dot{r}_\perp$:

$$\frac{d}{dt}\mathscr{L}(\|r\|)\hat{r} = \dot{\mathscr{L}}(\|r\|)\dot{r}_\| + \frac{\mathscr{L}(\|r\|)}{\|r\|}\dot{r}_\perp \qquad (III.4)$$

The derivative of the Langevin curve has two components, each proportional to the tangential component or normal component of the FFP velocity vector.

The equations above can be used to calculate the derivative of the signal equation. From Eqs. III.1 and III.2 and definitions III.3, we can rewrite the MPI signal as:

$$s(t) = \frac{d}{dt}\int\int\int B_1(u)m\rho(u)\mathscr{L}(\|r\|)\hat{r}\,du$$

and evaluate the derivative using Eq. III.4:

$$s(t) = \int\int\int B_1(u)m\rho(u)\left(\dot{\mathscr{L}}(\|r\|)\dot{r}_\| + \frac{\mathscr{L}(\|r\|)}{\|r\|}\dot{r}_\perp\right)du$$

Substituting for r gives us the convolution integral:

$$s(t) = \int\int\int B_1(u)m\rho(u)\dot{\mathscr{L}}$$
$$(k\|G(x_s(t)-u)\|)\cdot\frac{[kG\dot{x}_s(t)]^T[G(x_s(t)-u)]}{\|G(x_s(t)-u)\|^2}[G(x_s(t)-u)]du +$$
$$\int\int\int B_1(u)m\rho(u)\frac{\mathscr{L}(k\|G(x_s(t)-u)\|)}{k\|G(x_s(t)-u)\|}\cdot$$
$$\left[kG\dot{x}_s(t) - \frac{[kG\dot{x}_s(t)]^T[G(x_s(t)-u)]}{\|G(x_s(t)-u)\|^2}[G(x_s(t)-u)]\right]du$$

which yields:

$$s(t) = B_1(x)m\rho(x)***\dot{\mathscr{L}}(k\|Gx\|)\cdot\frac{[kG\dot{x}_s(t)]^T[Gx]}{\|Gx\|^2}[Gx]\Big|_{x=x_s(t)}$$
$$+ B_1(x)m\rho(x)***\frac{\mathscr{L}(k\|Gx\|)}{k\|Gx\|}\cdot\left[kG\dot{x}_s(t) - \frac{[kG\dot{x}_s(t)]^T[Gx]}{\|Gx\|^2}[Gx]\right]\Big|_{x=x_s(t)}$$

This form is not yet a simple PSF, and the FFP velocity magnitude $\|\dot{x}_s\|$ and the FFP velocity unit vector $\hat{\dot{x}}_s$ can be factored out by using an outer product vector identity $(a \cdot b)b = bb^T a$. This yields the Generalized MPI signal equation:

$$s(t) = B_1(x)m\rho(x)***k\|\dot{x}_s\|h(x)\hat{\dot{x}}_s|_{x=x_s(t)}$$

with Point Spread Function (PSF):

$$h(x)\dot{\mathscr{L}}[k\|Gx\|]\frac{Gx}{\|Gx\|}\left(\frac{Gx}{\|Gx\|}\right)^T G + \frac{\mathscr{L}(k\|Gx\|)}{k\|Gx\|}\left(I - \frac{Gx}{\|Gx\|}\left(\frac{Gx}{\|Gx\|}\right)^T\right)G$$

The signal equation indicates the inductively received signal is the matrix multiplication of a matrix PSF with the FFP velocity vector, $\hat{\dot{x}}_s$. The PSF does not change as a function of the FFP velocity magnitude, $\|\dot{x}_s\|$. If only the radially-symmetric scalar components of the PSF is considered, the PSF envelopes:

$$ENV_T = \dot{\mathscr{L}}(k\|Gx\|) \qquad (III.6)$$

$$ENV_N = \mathscr{L}\frac{(k\|Gx\|)}{k\|Gx\|} \qquad (III.7)$$

Figure 23:
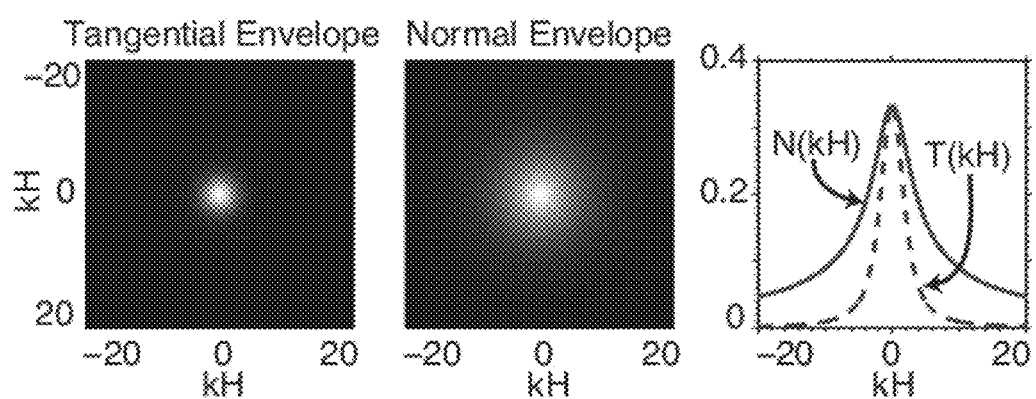
FIG. 23 shows graphs of the Tangential and Normal Point Spread Function envelopes, $ENV_T$ and $ENV_N$ shown for $\|kH\| \leq 20$, according to embodiments of the present disclosure. $ENV_T$ is the limit to MPI resolution, and defines MPI bandwidth. $ENV_N$ has approximately half the intrinsic resolution with $FWHM_T=4.2$ and $FWHM_N=9.5$. The value kH is unitless.

These envelopes seen in FIG. 23 give the maximum attainable resolution in MPI. The higher resolution Tangential Envelope, $ENV_T$, is the derivative of the Langevin equation. $ENV_T$ defines the intrinsic resolution and bandwidth requirements for MPI. The lower resolution envelope, $ENV_N$, is unique to generalized MPI and has a FWHM that is 2.3× wider. The FWHM of both envelopes can be solved analytically as a function of k or, alternatively, in terms of the particle diameter d:

$$FWHM_T \approx G^{-1}\frac{4.16}{k} \approx \frac{25k_B T}{\mu_0 G\pi M_{sat}d^3}[m] \qquad (III.8)$$

$$FWHM_N \approx G^{-1}\frac{9.5}{k} \approx \frac{57k_B T}{\mu_0 G\pi M_{sat}d^3}[m]$$

In certain embodiments, $ENV_T$ in equation III.6 may be derived in temporal frequency space, and may be derived in x-space. The second envelope in equation III.7 is unique to the generalized x-space formulation, and gives the resolution of the transverse component of the point spread function perpendicular to the FFP velocity vector.

The cubic relationship between resolution and particle diameter may depend on the origin of MPI's signal. MPI's resolution relies on the nonlinear effect of a small applied magnetic field causing a SPIO nanoparticle tracer to magnetically saturate. The Langevin equation indicates that the field required to saturate a single magnetic nanoparticle decreases with the nanoparticle's volume. As a result, resolution increases with the cube of the magnetic nanoparticle diameter.

A. MPI 3D Point Spread Function

The MPI process generates signals in multiple axes. In certain instances, the inductive receiver coils are perpendicular to the physical axes (x, y, and z) of the instrument, and the instrument produces images on an internal reference frame formed by vectors collinear and transverse to the FFP velocity vector, $\hat{\dot{x}}_s$. The collinear and transverse images may be distinct from the tangential and normal components.

Figure 24:
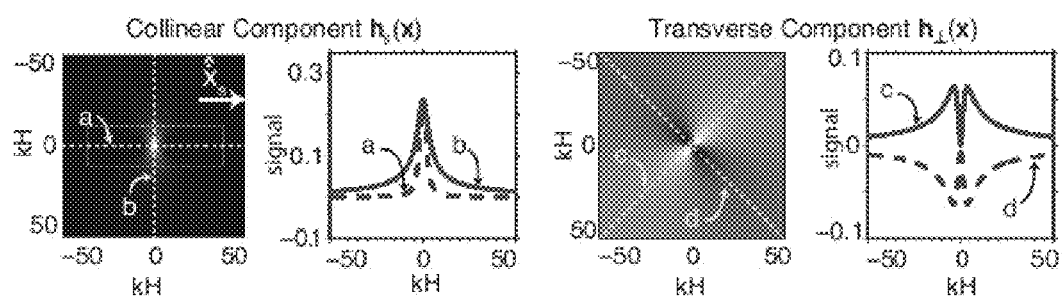
FIG. 24 shows graphs of collinear and transverse components of the matrix point spread function, according to embodiments of the present disclosure. The received images rotate with vector $\hat{x}_s$ (see FIG. 25). The collinear PSF component peak amplitude is 370% the tangential PSF component peak amplitude. The area of the box drawn in the collinear PSF is experimentally measured, as shown in FIG. 28.

To understand the origin of the collinear and transverse components of the PSF, the vector components of h(x) may be examined. Supposing that the velocity vector is aligned with the x unit vector, i.e. $\hat{\dot{x}} = \hat{e}_1$. Then, the collinear component is:

$$h_\|(x) = \hat{e}_1 \cdot h(x)\hat{e}_1$$

and the transverse components are:

$$h_{\perp,1}(x) = \hat{e}_2 \cdot h(x)\hat{e}_1$$

$$h_{\perp,2}(x) = \hat{e}_3 \cdot h(x)\hat{e}_1$$

where two perpendicular unit axes corresponding to the y and z axes, $\hat{e}_2$ and $\hat{e}_3$, are arbitrarily chosen. The resulting components of the PSF are shown in FIG. 24. The collinear and transverse components of the PSF form an excellent basis set for image reconstruction.

Figure 25:
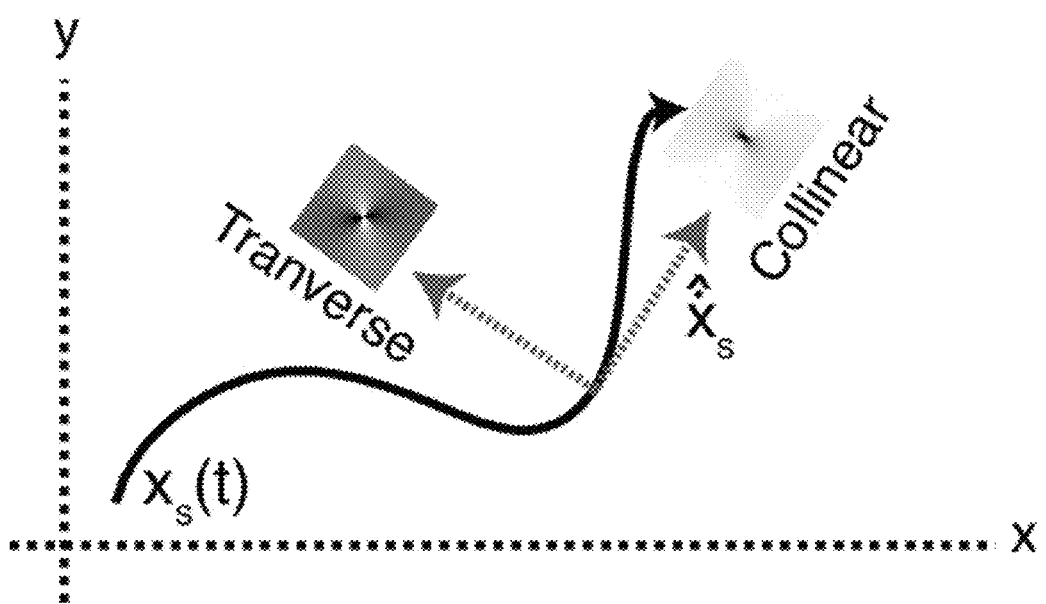
FIG. 25 shows a graph representing that MPI images are acquired on a reference frame formed by vectors collinear and transverse to the velocity vector $\hat{x}_s$, according to embodiments of the present disclosure.

If the FFP velocity vector is not oriented with one of the cardinal directions of the instrument, the received images change with the orientation of the velocity vector $\hat{\dot{x}}$. To illustrate how the reference frame is oriented with an arbitrary FFP path, the collinear and transverse components of the PSF may be oriented with the velocity vector in FIG. 25.

While the equations presented herein are general, in certain instances, the point spread function in an algebraic equation may be obtained. If the excitation vector $\hat{e}_1$ is fixed along the z-axis and a diagonal gradient matrix G=diag($G_x$, $G_y$,$G_z$) is assumed, then the collinear PSF is as follows:

$$h_{\parallel}(x, y, z) = \mathscr{G}[kH(x, y, z)]\frac{G_z^3 z^2}{H(x, y, z)^2} + \frac{\mathscr{L}[kH(x, y, z)]}{kH(x, y, z)}\left(1 - \frac{G_z^3 z^2}{H(x, y, z)^2}\right)$$

and one of the transverse PSFs on the receive axis aligned with the x-axis:

$$h_{\perp,1}(x, y, z) = \left(\mathscr{G}[kH(x, y, z)] - \frac{\mathscr{L}[kH(x, y, z)]}{kH(x, y, z)}\right)\frac{G_x G_z^2 xz}{H(x, y, z)^2}$$

where $H(x,y,z)=\sqrt{(G_x x)^2+(G_y y)^2+(G_z z)^2}$. The PSFs for these equations are shown in FIG. 24.

The collinear component is similar to the real part of a Lorentzian function seen in NMR, and is an even function. The collinear component is desirable and forms the bulk of the resolution and signal of the MPI imaging process. The collinear component is a vector sum of both the tangential and normal envelopes, $ENV_T$ and $ENV_N$, with the sharper envelope aligned with the velocity vector.

The transverse component is similar to the dispersion or odd-valued spectral component in NMR and is an odd function. The transverse component is a vector difference of the two point spread function envelopes. Across the diagonal (see FIG. 24), the signal received is precisely $$PSF_{\perp} = \pm\frac{1}{2}(\mathscr{G}(kH) - \mathscr{L}(kH)/\|kH\|).$$

As a result, the transverse component is significantly smaller in magnitude than the collinear component.

III. X-Space Theory

In certain embodiments, x-space theory is used to predict the collinear PSF, intrinsic resolution, and bandwidth requirements. In some cases, Magnetic Particle Imaging images are based on a physical principle that Ultrasmall Superparamagnetic Iron Oxide (USPIOs) completely align and saturate with the direction of any applied field greater than about 5 mT. As a result, USPIOs can be selectively saturated by the application of a strong (6500 mT/m) magnetic field gradient. The magnetic field is zero at the center of the gradient at a location we term the Field Free Point (FFP). Imaging occurs when the FFP is rapidly scanned across the sample, causing the magnetization of USPIOs passing through the FFP to flip and emit a signal that is detected using an inductive pickup coil. By gridding the signal to the instantaneous position of the FFP, an image of the nanoparticle distribution may be produced.

A. Point Spread Function

For a point source, i.e. a dirac delta source, the received image would be that of the MPI point spread function. In certain cases, the collinear component of the MPI signal is a PSF, h(x), multiplied by the velocity vector, $\hat{x}$ [m/s], scaled by the velocity of the FFP, $\|\dot{x}_s\|$ $$s_{\parallel}(t) = B_1(x) m \rho(x) *** k\|\dot{x}_s\| h_{\parallel}(x)\hat{x}_s|_{x=x_s(t)} \quad (1)$$

where $\rho(x)$ [particles/m³] is the magnetization density, $$m = \frac{\pi}{6}M_{sat}d^3 [Am^2]$$

is the magnetic moment of a single nanoparticle with saturation magnetization $M_{sat}$ [A/m] and diameter d [m], $B_1$ [T/A] is the sensitivity of the receive coils, and $$k = \frac{\mu_0 m}{k_B T}[m/A]$$

is related to the properties of the magnetic nanoparticles. If the excitation and reception vectors are fixed along the z-axis and assume an ideal diagonal gradient matrix G=diag ($G_x$,$G_y$,$G_z$), then we can write the collinear PSF $$h_{\parallel}(x, y, z) = \mathscr{G}[kH(x, y, z)]\frac{G_z^3 z^2}{H(x, y, z)^2} + \frac{\mathscr{L}[kH(x, y, z)]}{kH(x, y, z)}\left(1 - \frac{G_z^3 z^2}{H(x, y, z)^2}\right) \quad (2)$$

where $H(x,y,z)=\sqrt{(G_x x)^2+(G_y y)^2+(G_z z)^2}$. By dividing out the FFP velocity magnitude, $\|\dot{x}_s\|$, and gridding the received signal, we obtain an image of the collinear component of the PSF $$IMG_{\parallel}(x_s(t)) = s_{\parallel}(t)/\|\dot{x}_s\| = \rho(x) *** \hat{x}_s \cdot h_{\parallel}(x)\hat{z}|_{x=x_s(t)}$$

Figure 31:
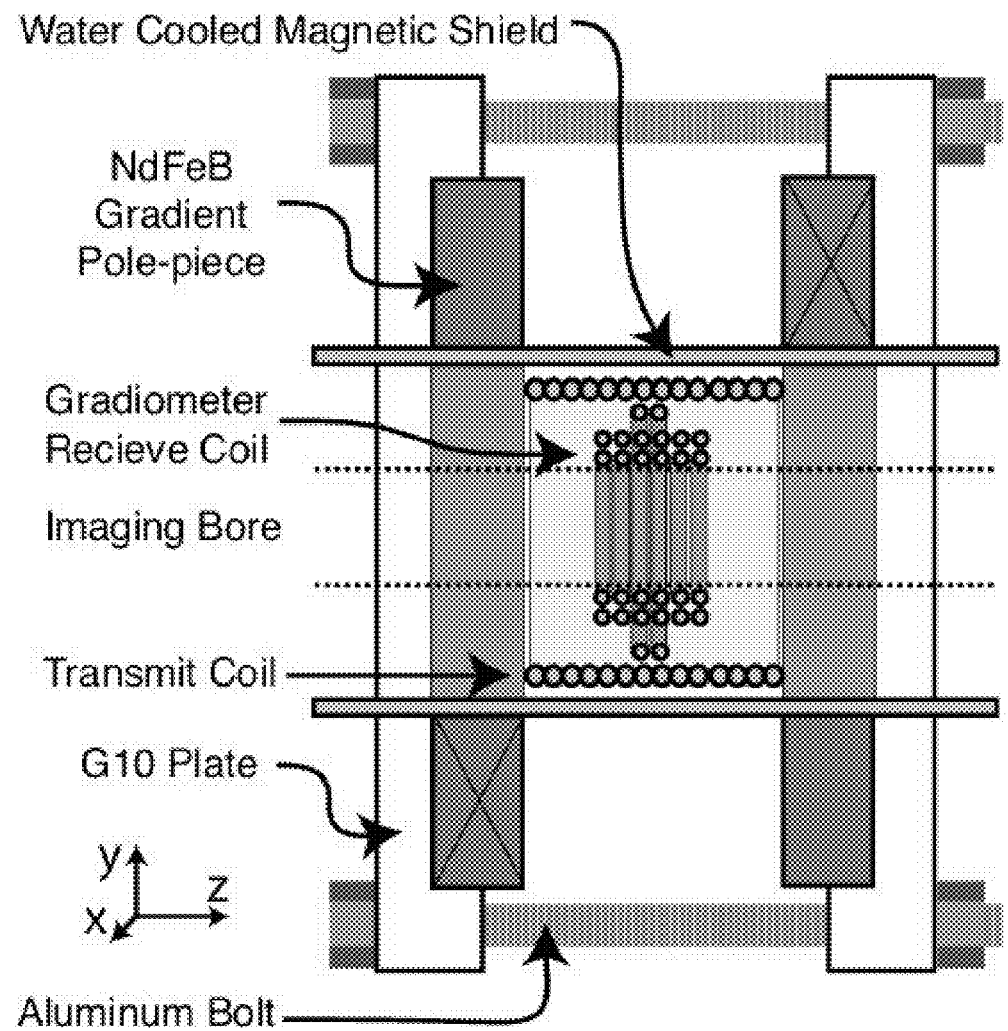
FIG. 31 shows a schematic of a tomographic MPI scanner with 2 cm×2 cm×4 cm Field of View constructed to test the x-space formulation for MPI, according to embodiments of the present disclosure. The excitation coil generated a 30 mT peak-to-peak oscillating magnetic field at 19 kHz. The NdFeB magnet gradient generated a gradient of $G_z$=6.0 T/m down the imaging bore, and $G_{x,y}$=3.0 T/m transverse to the imaging bore. The sample was mechanically moved through the bore.
Figure 32A:
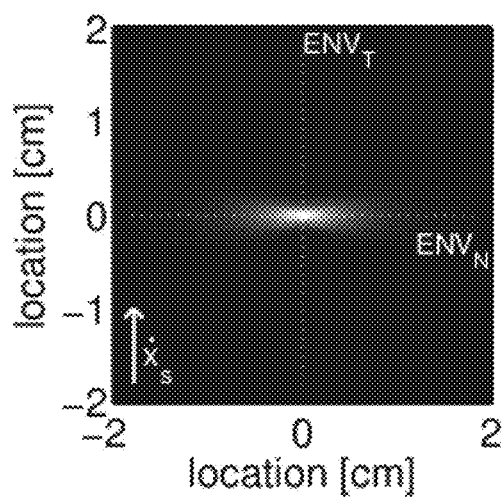
FIG. 32A shows a graph of a theoretical collinear PSF component for a 4 cm×4 cm FOV with 6 T/m×3 T/m gradient, according to embodiments of the present disclosure. The high gradient was collinear with the FFP velocity vector $\dot{x}_s$.

The collinear PSF is shown in FIG. 32A. In our instrument, excitation and reception are collinear with the z-axis (See FIG. 31).

B. Resolution

To understand the intrinsic resolution of MPI, we must first define resolution. Spatial resolution of the system is the ability to accurately depict two distinct points of equal intensity in space. There are many classical criteria for resolution including Rayleigh, Schuster, Houston, and Buxton. Houston proposed a criterion where two points are just resolved if two points are separated by the Full-Width at Half Maximum (FWHM), which if the criterion used herein.

From the MPI PSF (Eq. 2), the PSF has two radially symmetric components, which may be termed the transverse and normal PSF envelopes $$ENV_T = \mathscr{G}\left(k\sqrt{(G_x x)^2 + (G_y y)^2 + (G_z z)^2}\right) \quad (4)$$

$$ENV_N = \frac{\mathscr{L}\left(k\sqrt{(G_x x)^2 + (G_y y)^2 + (G_z z)^2}\right)}{\|k\sqrt{(G_x x)^2 + (G_y y)^2 + (G_z z)^2}\|} \quad (5)$$

From the Houston resolution criteria, the intrinsic resolution of the MPI process may be estimated analytically by solving for the FWHM of these envelopes for imaging the collinear component of the PSF if excitation occurs in the z-axis $$FWHM_T \approx G^{-1}\frac{4.16}{k} \approx \frac{25 k_B T}{\mu_0 G_z \pi M_{sat} d^3} [m] \qquad (6)$$

$$FWHM_N \approx G^{-1}\frac{9.5}{k} \approx \frac{57 k_B T}{\mu_0 G_{x,y} \pi M_{sat} d^3} [m] \qquad (7)$$

Figure 32B:
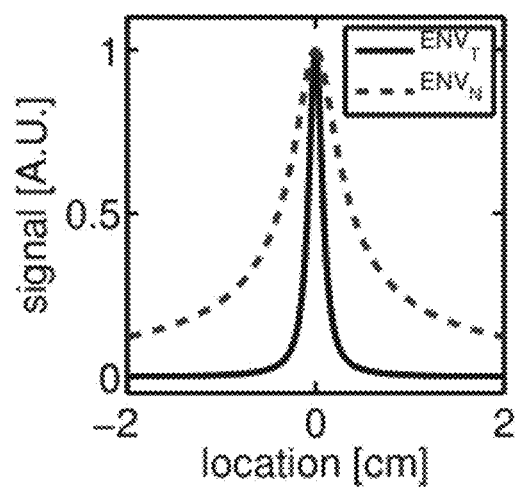
FIG. 32B shows a graph of Transverse and Normal PSF envelopes for the same system, according to embodiments of the present disclosure. The Normal envelope had a FWHM that was 460% wider.

That is, $ENV_T$ gives the resolution transverse to the FFP velocity vector $\hat{x}_s$, and $ENV_N$ gives the resolution normal to the FFP velocity vector (see FIG. 32B). This resolution implies that resolution in MPI improves with the cube of magnetic nanoparticle diameter, and that significant gains in resolution could be achieved through new tracer agents specifically tuned for MPI. For the particles shown herein, their apparent diameter is approximately 18±1.6 nm, which corresponds to transverse resolution of 1.6 mm resolution when imaged using a 6.0 T/m gradient (see Table IV below).

TABLE IV

Theoretical $FWHM_T$ for particles of given diameter and standard deviation in a 6 T/m gradient.

| Core Diameter [nm] | FWHM [mm] |
|---|---|
| 15 ± 3.4 | 2.2 |
| 17 ± 3.4 | 1.6 |
| 20 ± 3.4 | 1.1 |
| 25 ± 3.4 | 0.6 |
| 30 ± 3.4 | 0.3 |

C. Bandwidth

The highest resolution, and hence the highest bandwidth signal in MPI is limited by $ENV_T$, which can be approximated by a Lorentzian function. A Lorentzian function has a well behaved Fourier transform, which can be used to estimate the bandwidth of the MPI signal. If the magnetic field slew rate is defined as RG [T/s/$\mu_0$], then the signal spectrum is:

$$S(\omega) \approx \sigma N m \sqrt{\frac{2}{\pi}} \exp\left(-\frac{2|\omega|}{kRG}\right)$$

and solving for the half power point of the signal bandwidth gives:

$$F_{3dB} = \frac{kRG\ln(2)}{4\pi}$$
$$= \frac{M_{sat} d^3 RG \ln(2)}{24}$$

Because SNR decreases with increasing bandwidth, the minimum bandwidth necessary may be used. However, the reception may not be limited to only the 3 dB bandwidth of the signal, as this may result in spatial blurring. Assuming a brick-wall filter the bandwidth required to widen the FWHM by only 10% may require a receive bandwidth of $BW_{recv} \approx 3.8 F_{3\ dB}$.

D. Linearity/Shift Invariance

The adiabatic model assumed here is theoretically required for shift invariance. The adiabatic model assumes instantaneous rotation of the magnetic moments in response to an applied magnetic field. In some instances, the rotation of a magnetic nanoparticle lags the applied field due to both Neel and Brownian relaxation. This lag can be described by a relaxation time constant, which is in the range of 1-30 μs for the Brownian relaxation dominated nanoparticles used in MPI. As shown in the experimental results, the adiabatic model still produces images with high resolution and SNR when using Resovist.

MPI interrogates magnetic nanoparticles with a rapidly varying magnetic field. This applied field can induce a signal in the receive coil many orders of magnitude larger than the nanoparticle signal. This applied field may be a sinusoid, whose frequency may be termed as the "fundamental frequency". To avoid overwhelming the small nanoparticle signal, the fundamental frequency may be filtered out using band-stop and high-pass filters. In some instances, this breaks the LSI properties of the system because information used for reconstruction has been removed.

Experimental

From a basis in x-space theory, an imaging technique was developed that enabled the acquisition of an intrinsic MPI image. The technique may include three components: (1) imaging pulse sequence, (2) gridding, and (3) image assembly. This technique resulted in a LSI system, and the resulting image was the magnetization density convolved with the PSF.

A. Pulse Sequence

The path of the FFP through x-space may be considered as a MPI pulse sequence. There are various pulse sequences possible in MPI, including but not limited to raster, Lissajous, polar-rose, etc., and the path of the FFP may affect the SNR of the resulting image.

Figure 33A:
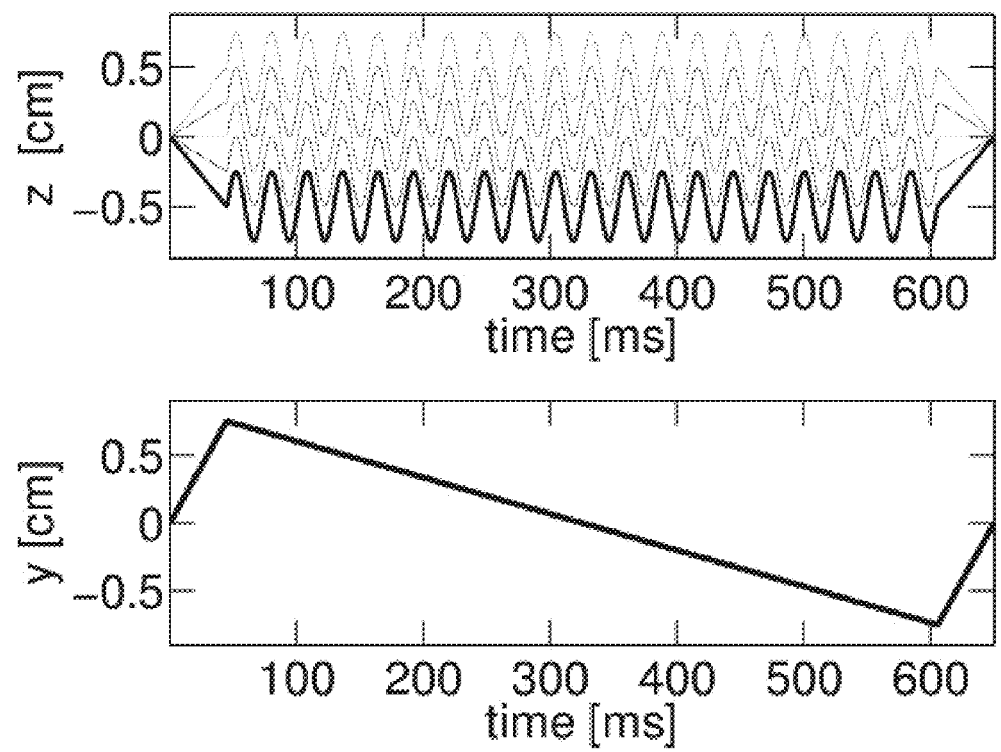
FIG. 33A shows a graph of an x-space pulse sequence, according to embodiments of the present disclosure.
Figure 33B:
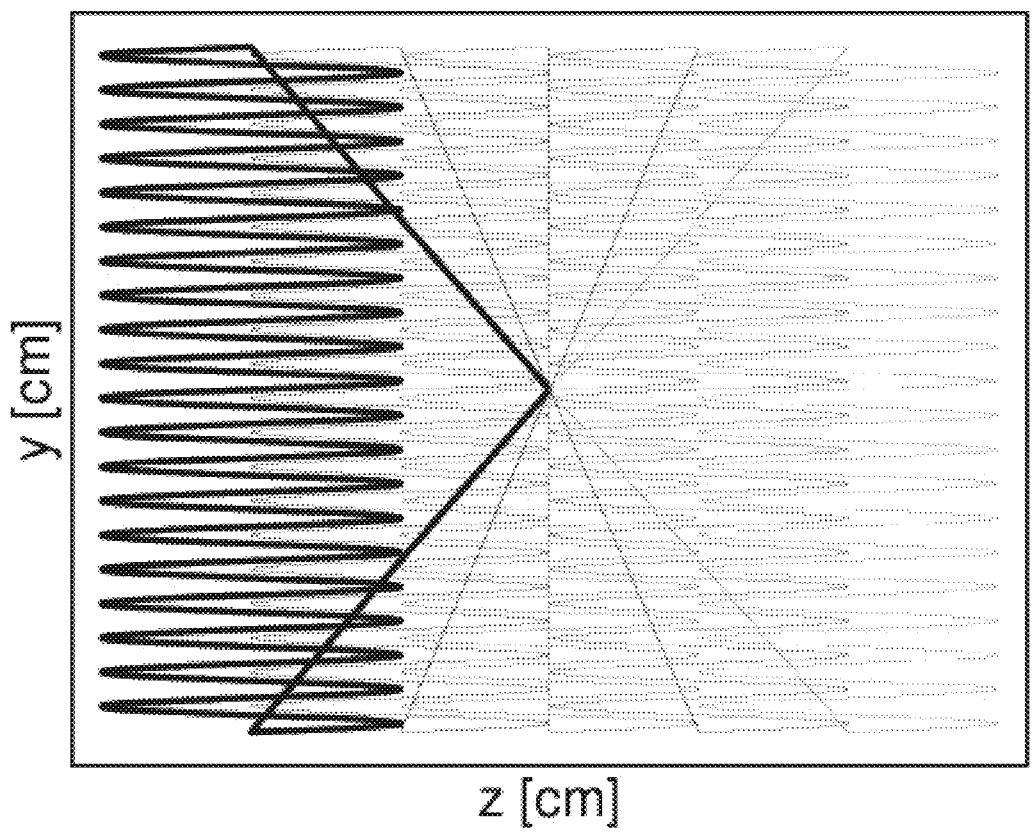
FIG. 33B shows a graph of a pulse sequence used in the x-space scanner with overlap of 50%, according to embodiments of the present disclosure. Rapid movement in z was performed electronically at 20 kHz, while slow movement in x, y and z was performed mechanically. In certain embodiments, the x-space scanner may slowly move the FFP electronically.
Figure 34:
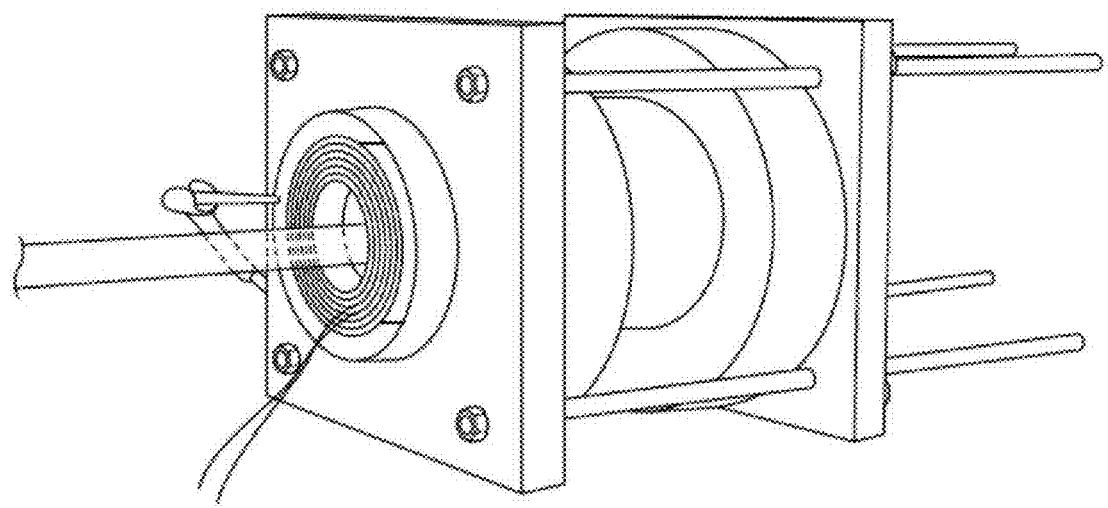

A raster pulse sequence was used (see FIGS. 33A and 33B) for this x-space scanner as it was straightforward to implement with the image equation (Eq.3). A raster scan simplified reconstruction because the FFP velocity unit vector $\hat{x}_s$ can be considered a constant since rapid FFP movement was limited to the z-axis. Slow movement in x, y and z was done mechanically.

MPI systems can use a large gradient field to increase resolution at the expense of reducing the field of view of a scan. For example, the scanner described here generated a 30 $mT_{peak-peak}$ excitation amplitude on top of a 6.0 T/m gradient, which moved the FFP by 5 mm. This excitation amplitude exceeded the limits of magnetostimulation for a chest scanner, but would not exceed the limits of magnetostimulation in an extremity or head scanner.

In order to scan a larger FOV, the system acquired partial FOVs that were later assembled into a full image. A partial FOV was acquired by rapidly scanning 5 mm in z while simultaneously mechanically translating the sample 1.5 cm in y. To acquire the full image, the sample was stepped down the bore in z so that the partial FOVs overlapped. It was possible to move the FFP electronically through the addition of high amplitude slow field shifting magnets, which were previously implemented in a mouse scale narrowband MPI system.

B. Gridding

A systematic method for converting the signal returned by the pulse sequence into x-space was developed. To do this, the signal was processed to ensure the phase linearity, and then the received signal was gridded to the instantaneous location of the FFP.

The magnetic signal generated by the nanoparticles was received by an inductive receive coil. The received signal was contaminated by a large interfering sinusoid at the fundamental frequency. The fundamental frequency was removed by a notch filter and the remaining signal was pre-amplified. The signal was conditioned by a High-Pass Filter (HPF) followed by a second stage of amplification.

Figure 35:
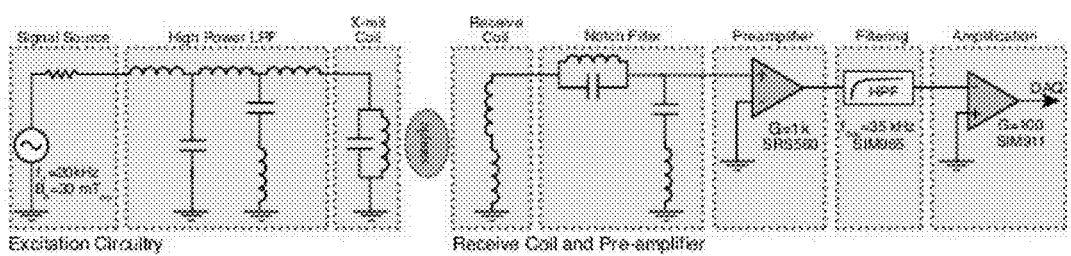
FIG. 35 shows a schematic of the Transmit-Receive electronics, according to embodiments of the present disclosure.

In certain instances, the receive subsystem did scramble the phase of the received signal, as phase corresponds to location in x-space. A high-Q notch filter built as shown in FIG. 35 was tuned to minimally change the phase of the signal. The addition of a HPF improved noise rejection by removing low-frequency interferes including mains noise, signal from slow FFP movement magnets, remaining fundamental signal, and 1/f noise. Although, the HPF broke the phase of the received signal, it was possible to reverse this phase accrual through digital anti-causal filtering or a phase-matched analog or digital all-pass filter. Since a Butterworth filter was simple to design in the digital domain, a non-causal filtering step was used to recover the phase. The phase corrected signal $s_{ph}$ can be expressed as $$s_{ph}(t^*) = \text{HPF}[s(t^*)]$$

where $t^* = -t$ to reverse time. In certain embodiments, the high pass filter was an eighth order Butterworth with a 25 kHz cutoff frequency.

Using a simple method of gridding, the phase corrected signal was transformed from the time domain to the image domain. This method did not require regularization, optimization techniques, or prior knowledge of the magnetic response of the tracer. Following the scan, the phase corrected signal was divided by the instantaneous FFP velocity, and the amplitude corrected signal was gridded to the instantaneous location of the FFP. That is $$IMG(x(t^*)) = \frac{s_{ph}(t^*)}{\|\dot{x}_s\|}$$

IMG(x) was interpolated and averaged using a nearest neighbor algorithm.

C. Image Assembly

When imaging with a partial FOV, filtering the received signal removes the LSI properties of the system. In certain instances, the HPF of the time domain signal may be considered as a loss of low spatial frequency information to account for the loss of low frequencies. For the loss of temporal frequencies near the fundamental frequency, this spatial signal loss may be approximated as a DC offset so that the mean signal value was zero. In certain embodiments, this means that if multiple overlapping partial FOVs were acquired, the overlap between signals may be found that minimizes their overlap error. Since only a constant DC offset was lost and assuming boundary conditions at the endpoints of the scan, the DC offsets necessary to optimally overlap the partial FOVs may be estimated. Adding the overlapped partial FOVs weighted by SNR of each point returned an assembled image.

Relationship Between X-Space Theory and Bandwidth, Achievable Resolution and SNR X-space MPI theory indicates that various parameters may depend on the receive bandwidth. In some instances, a wider bandwidth will improve resolution. In certain cases, continuing to increase the bandwidth beyond what is necessary given a scan rate and magnetic field strength will not continue to improve the achievable resolution. In some embodiments, the bandwidth may be linked to the SNR of the system. Continuing to increase the bandwidth may decrease SNR in certain embodiments. In some cases, reducing system bandwidth may improve SNR, irrespective of whether the system is coil noise or preamplifier noise dominated.

A. X-Space MPI Theory

The x-space formalism for MPI gives a signals and systems framework to understanding the raw MPI signal, and how to convert the time domain signal into the spatial domain without matrix inversion. X-space MPI may be used to derive system resolution, bandwidth, and SNR from first principles. In certain cases, the temporal harmonic domain may be used, where the harmonics of the received MPI signal in response to a sinusoidal excitation frequency. X-space analysis may differ from these analyses by describing the MPI signal in the time domain without analysis of harmonics. From the assumption that the magnetic nanoparticles respond adiabatiacally to the applied magnetic field, in one dimension, the MPI signal in volts can be written as a convolution $$s(t) = B_1 m\rho(x) * \mathscr{L}\left[kGx\right]|_{x=x_s(t)} kG\dot{x}_s(t) \quad (3.1)$$

where $B_1$ [T/A] is the sensitivity of the receive coil, m [Am$^2$] is the magnetic moment of a single nanoparticle, $\rho$[particles/m$^3$] is the nanoparticle density, $\mathscr{L}$ is the derivative of the Langevin function, k [m/A] is related to the nanoparticle properties, G [A/m/m] is the magnetic field gradient, x is the location in real space, and $x_s(t)$ is the location of the FFP.

The rate of change of a triangular, sinusoidal, or arbitrarily changing FFP position may be modeled as a linearly changing FFP position. A linearly ramping field with ramp rate R[m/s] gives a time varying position $x_s(t)=Rt$. This corresponds to a time varying magnetic field of $$H(t) = Gx_s(t)$$
$$= RGt$$

where we term RG [A/m/s] the magnetic field slew rate.

For N particles located at the origin, $\rho(x,y,z)=N\delta(x)\delta(y)\delta(z)$, the 1D signal equation 3.1 and approximating the Langevin curve as a Lorentzian gives $$s(t) = B_1 NmkRG\dot{\mathscr{L}}[kRGT] \approx B_1 NmkRG\zeta(kRGt)$$

where $$\dot{\mathscr{L}}[kH] \approx \zeta[kH] = \frac{2}{\pi} \frac{2}{4+(kH)^2}$$

Figure 45:
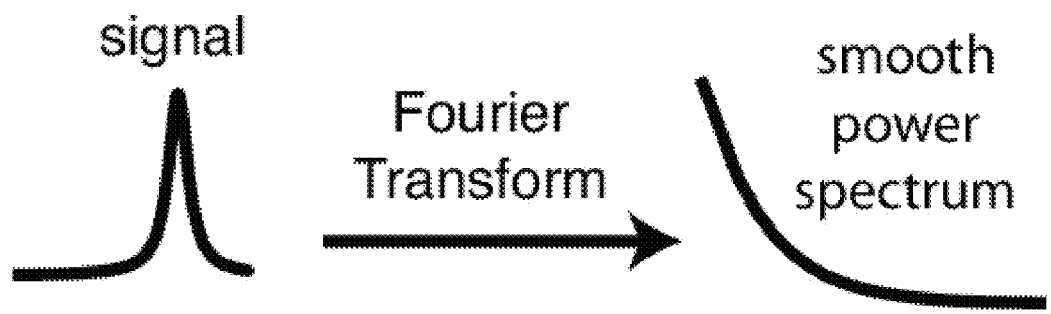
FIG. 45 shows a graph of a raw signal that has a smooth power spectrum density, according to embodiments of the present disclosure.

Taking the Fourier transform of s(t) yields an estimate of MPI bandwidth, which is a smooth spectrum (see FIG. 45)

$$S(\omega) \approx B_1 Nm \sqrt{\frac{2}{\pi}} \exp\left(-\frac{2|\omega|}{kRG}\right)$$

Figure 46:
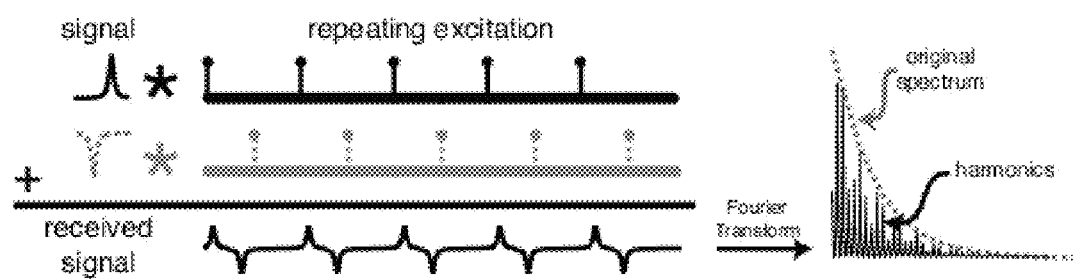
FIG. 46 shows a graph of repeating scanning of the sample introduces harmonics, according to embodiments of the present disclosure.
Figure 47:
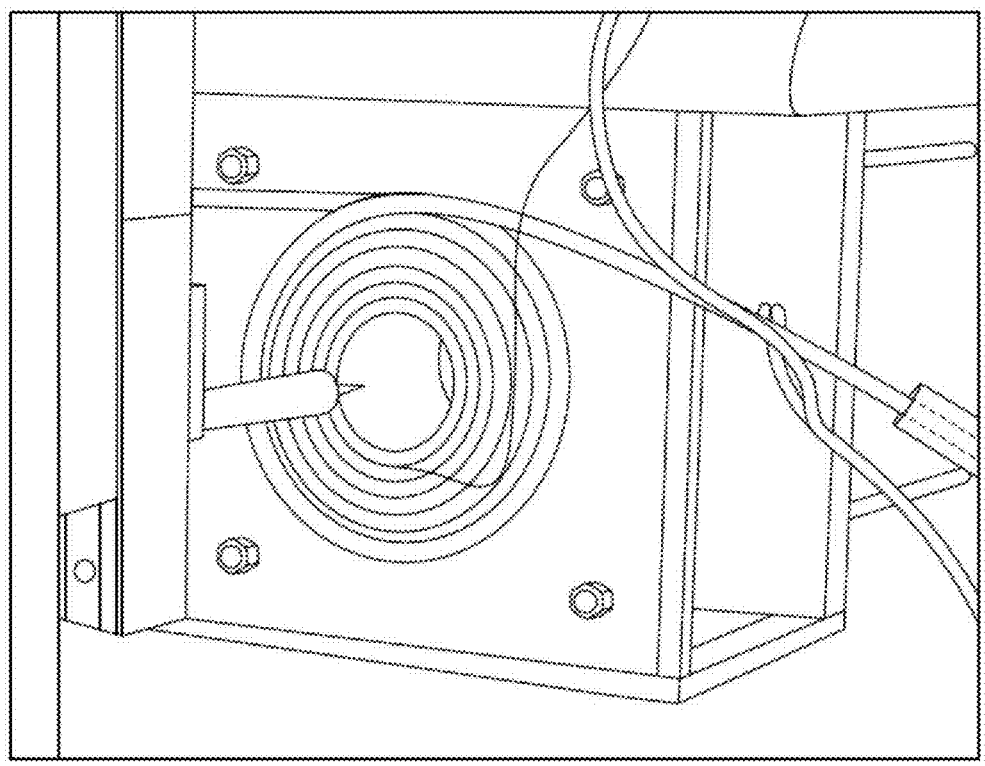
FIG. 47 shows a photographic image of the small scale MPI scanner showing three axis robot on left, and the scanner bore in the center, according to embodiments of the present disclosure.

The harmonics typically seen in the received spectrum are an artifact of the repeating excitation, and not fundamental to MPI (see FIG. 46). This is because the average position of the FFP moves slowly when compared to the rapid movement of the FFP in a typical scanning sequence. In one dimension, this may be similar to sampling the field of view repeatedly in time. This is similar to convolving the signal for a single pass across the FOV with a repeating Shah function. However, the Fourier transform of the Shah function samples the received signal spectrum at multiples of the repetition frequency, leading to harmonics in the received spectrum. If the FFP was moved rapidly so that the same field of view is not repeatedly sampled, the received spectrum would be smooth.

With a suitable mapping of the time domain to the spatial domain using x-space theory, the Fourier transform of the spatial domain is in the spatial frequency domain. For the case of the linear ramp excitation, the spectra of the temporal and spatial frequency domains are identical. This enables direct measurement of the Modulation Transfer Function (MTF), which enables comparison of MPI resolution with other imaging modalities such as x-ray and magnetic resonance imaging.

B. Bandwidth and Resolution

The finite receiver bandwidth of a real system reduces the bandwidth from the intrinsic resolution to what may be termed the achievable resolution. To see this mathematically, a receive bandwidth, $\Delta f$, with a brick-wall filter may be assumed. Then, the received signal in Fourier and real space is:

$$S_{LPF}(\omega) \approx B_1 Nm \sqrt{\frac{2}{\pi}} \exp\left(-\frac{2|\omega|}{kRG}\right) rect\left(\frac{1}{4\pi}\frac{|\omega|}{\Delta f}\right)$$

$$S_{LPF}(t) \approx B_1 NmkRG\dot{\mathscr{L}}[kRGt] * 2\Delta f sinch(2\Delta ft)$$

This implies that limiting the bandwidth in frequency space with a lowpass filter will cause widening of the PSF, reducing the achievable resolution. The intrinsic resolution is approached asymptotically as the receive bandwidth is increased. 150% of the intrinsic resolution is not reached until the receiver bandwidth is $\Delta f_{1.5} \approx 2.2 \, F_{3 \, dB}$, and 110% of the intrinsic resolution is not reached until $\Delta f_{1.1} \approx 3.8 \, F_{3 \, dB}$. If a Gaussian low pass filter was assumed instead, the profile may be approximated as a Voigt profile, which is a Lorentzian convolved with a Gaussian, for which there may be closed form approximations.

C. Bandwidth and SNR

The signal generated by the magnetic nanoparticles is detected and amplified in the receive chain. The receive chain has two primary noise producing components, the pre-amplifier and the inductive receiver coil. In certain embodiments, it may be desirable to minimize the noise added by these two components, which are dominated by the voltage noise of the preamplifier by the resistance of the receive coil. When designing the receive chain the preamplifier and receive coil design may depend on the receive bandwidth.

In certain embodiments, MPI preamplifiers are not matched to a resistive or resonant impedance. A pre-amplifier suitable for MPI may have low noise amplification across a wide bandwidth under 1 MHz. For example, a commercially available ultra-low noise FET preamplifier that has found use is the SA-220F5 (NF Corporation, Yokohama, Japan), which has an input referred voltage noise of $\theta_n = 0.5$ nV/$\sqrt{Hz}$, current noise of $i_n = 200$ fA/$\sqrt{Hz}$, and an input capacitance of 65 pF. If a receive coil with a relatively large inductance of 500 µH was used, the current noise would correspond to an equivalent voltage noise of 0.1 nV/$\sqrt{Hz}$ at 150 kHz. At the low frequencies used in MPI, even for a high impedance receive coil, the total input referred voltage noise of a FET input stage is dominated by the voltage noise rather than the current noise. Since the MPI received signal is typically at a higher frequency than 1/f noise present in Si-BJT and Si-JFET preamplifiers, the body and coil noise may be modeled as spread across a noise bandwidth, $\Delta f$. The noise of a resistive receive coil may be modeled as a broadband Johnson noise. Assuming that the AC resistance remains flat and coil noise dominance, the input referred resistive voltage noise can be calculated across the noise bandwidth $$\langle n \rangle = \sqrt{(e_n^2 + 4k_B(T_{coil}R_{coil} + T_b R_b) + i_n^2 Z_{coil})\Delta f} \approx \sqrt{(e_n^2 + 4k_B T_{coil} R_{coil})\Delta f}$$

where $e_n$ [V/$\sqrt{Hz}$] is the voltage and current noise amplitude per unit bandwidth of the preamplifier, $k_B$ is Boltzmann's constant, $T_{coil}$[K] is the temperature of the coil, and $R_{coil}$[$\Omega$] is the resistance of the coil, and $T_b$ is the body temperature, and $R_b$ is the body resistance. The noise current $i_n$ [A/$\sqrt{Hz}$] may be ignored because noise currents tend to be negligible at the low frequencies used in broadband MPI.

Since the dominant noise sources in the front end electronics have been estimated above, the Signal to Noise Ratio (SNR) may be calculated as follows:

$$SNR \approx \frac{S_{max}}{\sqrt{(e_n^2 + 4k_B T_{coil} R_{coil})\Delta f}}$$

In certain embodiments, it may be desirable to achieve coil noise dominance where the Johnson noise from the coil resistance is greater than the amplifier noise contribution, i.e. $4K_B T_{coil} R_{coil} > e_n^2$, as the body noise contribution is small under 1 MHz. In certain embodiments, cooled copper and superconducting receive coils may facilitate achieving coil noise dominance.

Gridding and Fundamental Frequency Recovery

In certain embodiments, the method of imaging magnetic particles in x-space MPI includes gridding and fundamental recovery. Gridding may be used to transform the received signal from the time domain to the image domain. The technique of a partial FOV can be used to estimate the low frequency content that is lost when the fundamental frequency is filtered out. These x-space reconstruction techniques do not require regularization, optimization techniques, or prior knowledge of the magnetic response of the tracer.

A. Reconstruction Methods: Gridding

Gridding in MPI is the process of sampling the received signal s(t) onto a grid in real space, or x-space, which corresponds to the instantaneous location of the FFP. In some cases, the collinear and transverse components are gridded separately. To do this, the image may be separated into collinear and transverse signals:

$$s_{\|}(t) = \hat{x}_s \cdot s(t)$$

$$s_{\perp,1}(t) = (\hat{x}_s \times \hat{e}_1) \cdot s(t)$$

$$s_{\perp,2}(t) = ((\hat{x}_s \times \hat{e}_1) \times \hat{e}_2) \cdot s(t)$$

An arbitrary unit vector $\hat{e}_1$ may be chosen to cross with the velocity unit vector $\hat{x}_s$ to build a perpendicular basis set of transverse vectors. Choice of this arbitrary vector assumes that $\hat{e}_1$ and $\hat{\dot{x}}_s$ are not collinear, i.e. $\hat{\dot{x}}_s \times \hat{e}_1 \neq 0$.

If the pulse sequence is designed so that the velocity unit vector $\hat{\dot{x}}_s$ is constant, e.g. with fast movement only in one direction, gridding of the collinear and transverse signals may be simplified. Ignoring the receiver coil sensitivity and choosing arbitrary unit vectors $\hat{e}_1$ and $\hat{e}_2$ not collinear with the FFP velocity $\hat{\dot{x}}_s$ gives the Generalized MPI Image Equation:

$$IMG_\parallel(x_s(t)) = s_\parallel(t)/\|\dot{x}_s\| \qquad (IV.1)$$

$$= \rho(x) ** * \hat{\dot{x}}_s \cdot h(x)\hat{\dot{x}}_s \big|_{x=x_s(t)}$$

where the magnitude of the FFP velocity is normalized. Similar gridding can be done for the remaining transverse images. This image equation is similar to the k-space analysis of MRI, but here the scanning occurs in x-space rather than in k-space, so no Fourier Transform is required.

B. Reconstruction Methods: Fundamental Recovery

MPI interrogates magnetic nanoparticles by subjecting the sample to a rapidly varying magnetic field. In certain embodiments, the applied magnetic field contaminates the received signal as the applied field induces a signal in the receive coil that is many orders of magnitude larger than the signal generated by the magnetic nanoparticles. This applied field is typically a sinusoid, whose frequency we term the "fundamental frequency".

To correct for the loss of the fundamental frequency, a partial FOV technique may be used. MPI systems can use a large gradient field to increase resolution at the expense of reducing the FOV of a scan. For example, the scanner described herein generated a 30 $mT_{peak-peak}$ excitation amplitude on top of a 6 T/m gradient, giving a total FOV of about half a centimeter. In certain embodiments, this excitation amplitude may exceed the limits of magnetostimulation for a chest scanner and may be near the magnetostimulation limit for an extremity scanner. However, partial FOV images can be taken that can be combined together for the full FOV by slowly moving the average position of the FFP mechanically or with an electromagnet.

When scanning an image with overlapping partial FOVs, it may be possible to recover the lost fundamental signal, which is important to shift invariance. For instance, a plurality of partial FOV images may be combined into a larger field of view image. In certain embodiments, high-pass filtering of the time-domain signal as a loss of low-spatial frequency information may be used. For the loss of temporal frequencies near the fundamental frequency, this spatial-signal loss can be approximated as a DC offset. In some instances, if multiple overlapping partial FOVs are acquired, the overlap between signals may be found that minimizes their overlap error. Since only a constant DC offset was lost and assuming boundary conditions at the endpoints of the scan, the resulting reassembled image will approximate the original spatial convolution.

Experiment 2

C. Experimental Methods

Figure 26A:
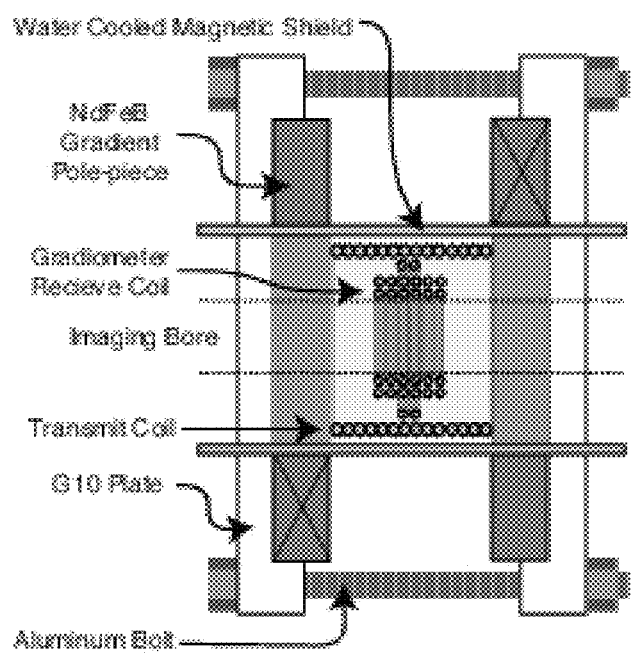
FIG. 26A shows a schematic of a tomographic MPI scanner with 2 cm×2 cm×4 cm Field of View, according to embodiments of the present disclosure. The excitation transmit coil generated a 30 mT peak-to-peak oscillating magnetic field at 20 kHz. The NdFeB magnet gradient generated a gradient of 6 T/m down the imaging bore, and 3.25 T/m transverse to the imaging bore.
Figure 26B:
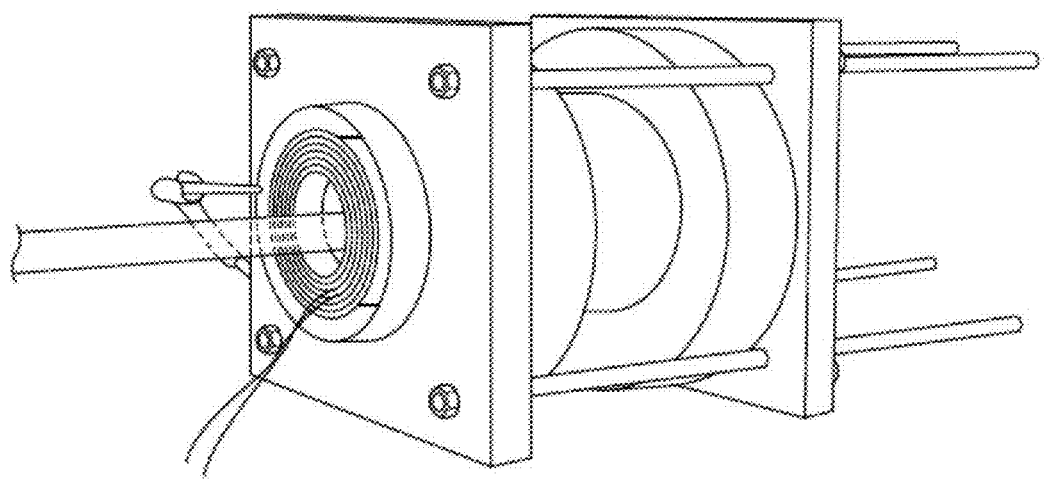
FIG. 26B and FIG. 34 show photographs of an x-space MPI scanner, according to embodiments of the present disclosure. The free bore before addition of the transmit and receive coils was 8.4 cm.

A three-dimensional MPI scanner was built, as shown in FIGS. 26A and 26B. The system was constructed with a permanent magnet gradient (6 T/m down the bore and 3 T/m transverse to the bore) and an excitation coil in one dimension collinear to the bore. The FFP was rapidly scanned using the resonant transmit coil and the signal produced was received with a receive coil wound collinear to the transmit coil. The receive coil received the collinear component of the vector PSF. The transmit and receive coils were collinear with the larger gradient along the bore, which was twice the magnitude of the gradient transverse to the bore. The collinearity of the coils was chosen for ease of construction but resulted in an intrinsic resolution in the transverse direction that was approximately four times less than in the collinear direction (see Eq. III.8).

The resonant excitation coil generated 30 mT peak-to-peak at 20 kHz and was driven by an audio amplifier (AE Techron LVC5050, Elkhart, Ind., USA) with ~5 kW of instantaneous power at a pulsed 2% duty cycle. The signal from the receive coil was filtered by a passive notch filter, amplified by a battery powered preamplifier (SR560, Stanford Research Systems), and high-pass filtered at 35 kHz (SIM965, Stanford Research Systems). Following the analog signal chain, the signal was digitized by a 16-bit data acquisition system with a 1.25 MSPS sampling rate (National Instruments USB-6259, Austin, Tex., USA), phase corrected, and low-pass filtered at 400 kHz. The system was controlled by custom software written in MATLAB (Mathworks MATLAB, Natick, Mass., USA).

The 30 mT peak-to-peak excitation enabled a partial FOV of approximately 0.5 cm along the z-axis. The signal for the received partial FOV was gridded to the instantaneous location of the FFP and assigned to a physical location on the phantom. The phantom was stepped in 1 mm steps along the z-axis for 4 cm, which acquired a partial FOV line scan at each step. The line scans were reassembled by estimating the missing fundamental to generate an assembled full FOV of 4.5 cm along the z-axis. A total of 20 line scans were taken by moving in 1 mm steps transverse to the bore, for a full FOV of 2 cm in the y-axis. Phantoms were constructed using 400 micron ID tubing filled with undiluted SPIO tracer (Resovist, Bayer-Schering).

D. Results & Discussion

Figure 27A:
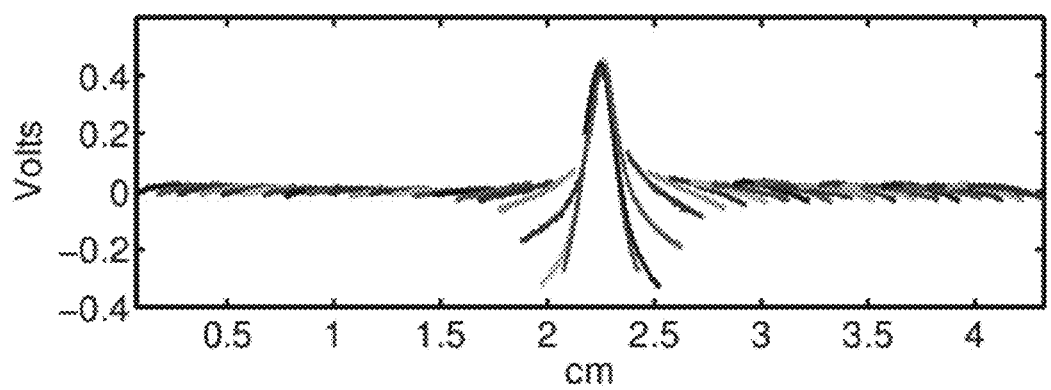
FIG. 27A shows a graph of experimental data showing 40 overlapping partial field of view line-scans for a 400 micron point source phantom, according to embodiments of the present disclosure. The baseline component for each partial FOV was lost in the scanning process due to the contamination of first harmonic imaging data by direct feedthrough.
Figure 27B:
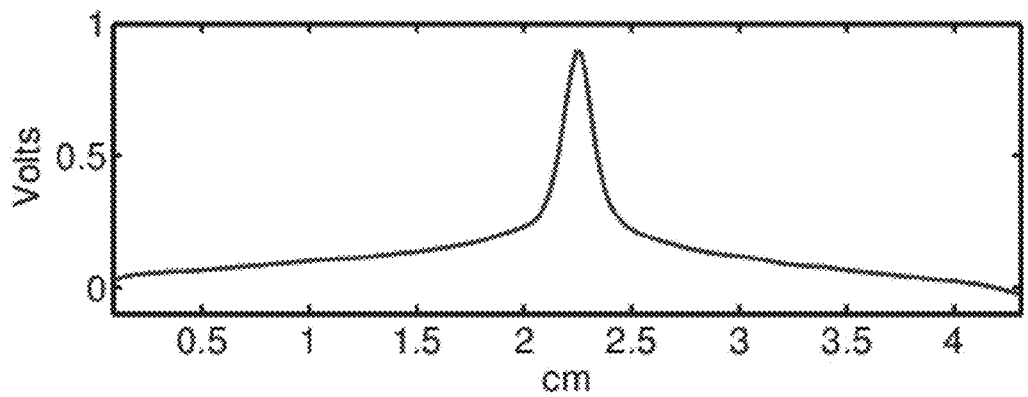
FIG. 27B shows a graph using standard image processing methods to reconstruct a smooth version of the data segments, obtaining the maximally continuous image, according to embodiments of the present disclosure.
Figure 28A:
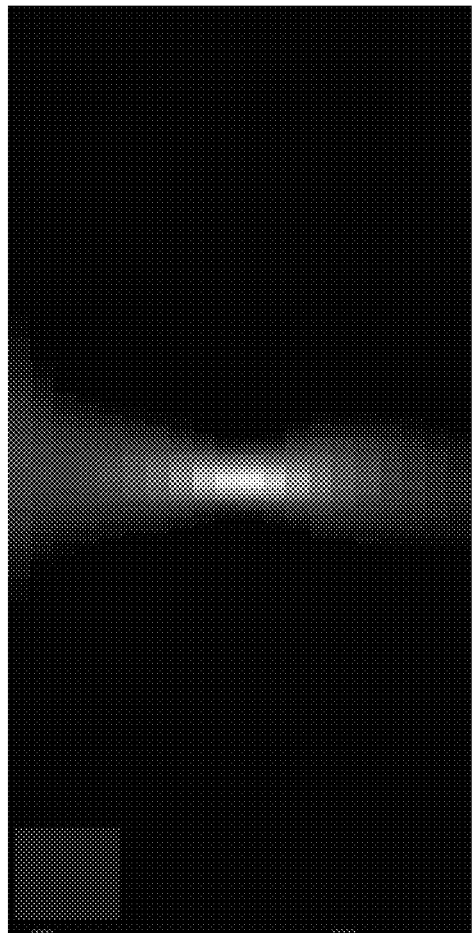
FIG. 28A shows a graph of measured two-dimensional collinear PSF showing correspondence to FIG. 24, according to embodiments of the present disclosure. The measured FWHM was 1.6 mm along the imager bore and 7.4 mm transverse to the imager bore. The PSF phantom was a 400 micron tubing oriented perpendicular to the bore.
Figure 28B:
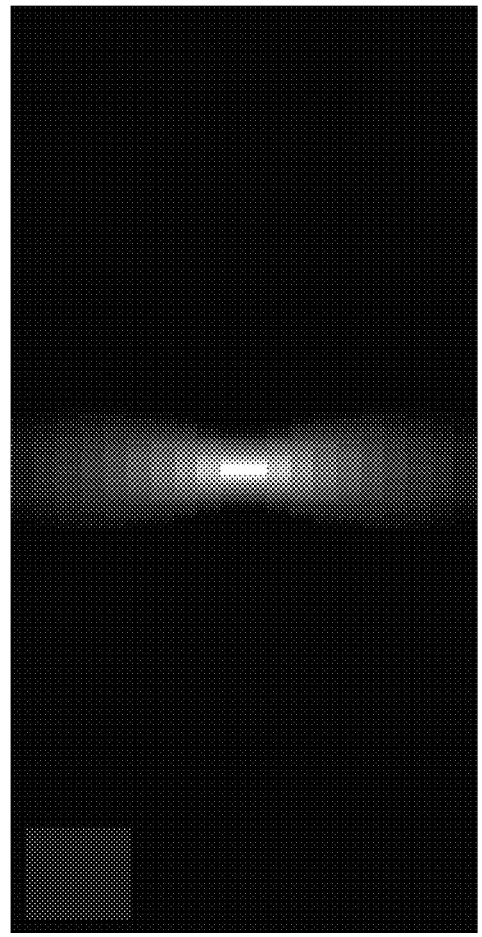
FIG. 28B shows a graph of theoretical PSF assuming SPIO nanoparticle of lognormal size distribution with d=17±3.4 nm, according to embodiments of the present disclosure.

In FIGS. 27A and 27B experimental data is shown, showing the one-dimensional scan of a point source before and after fundamental recovery. The fundamental was recovered by estimating the DC offset of each segment so that a maximally smooth image was produced.

Figure 29A:
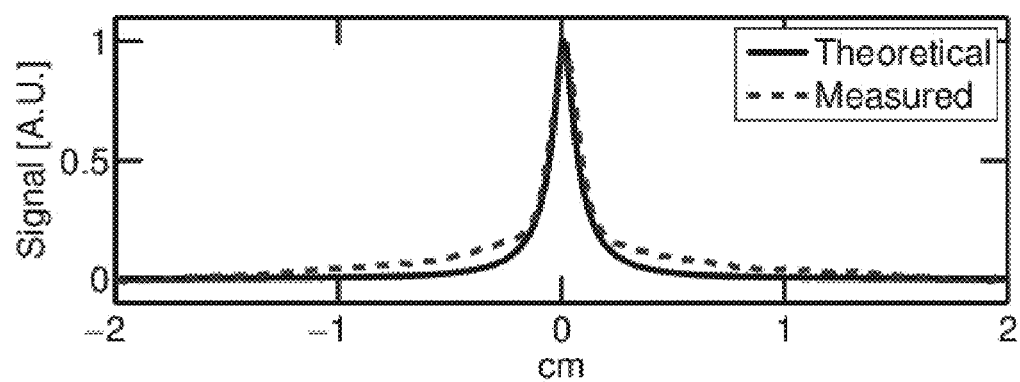
FIGS. 29A and 29B shows graphs of profiles across the point spread function shown in FIGS. 28A and 28B, which show good agreement between theoretical and measured values, according to embodiments of the present disclosure.
Figure 29B:
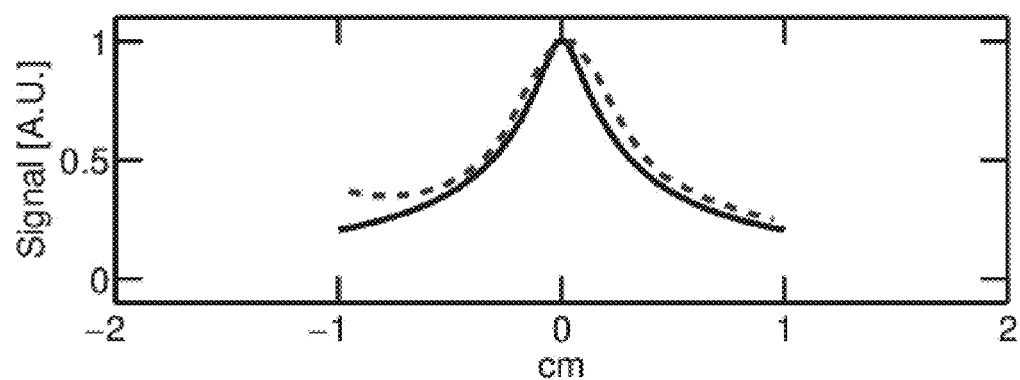
Figure 30A:
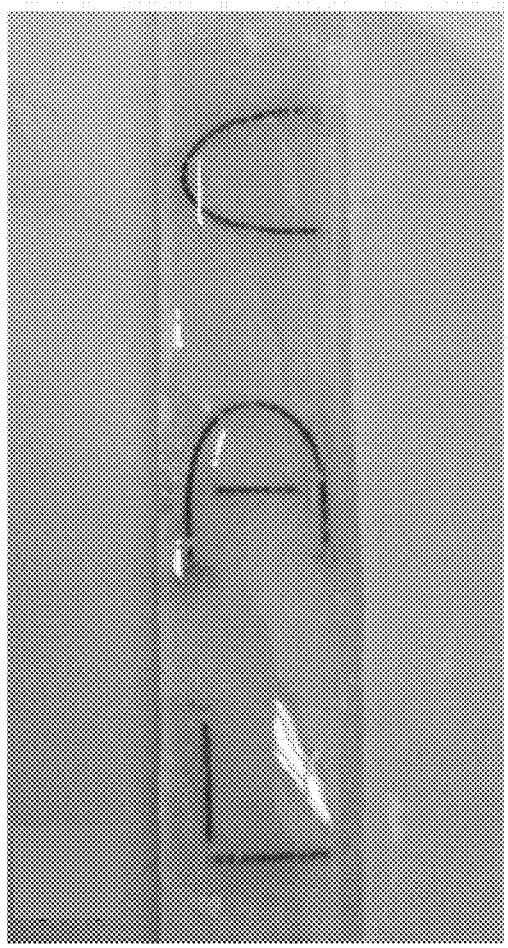
FIG. 30A shows a photograph of a "CAL" phantom image built using 400 micron ID tubing filled with undiluted tracer and encapsulated, according to embodiments of the present disclosure.
Figure 30B:
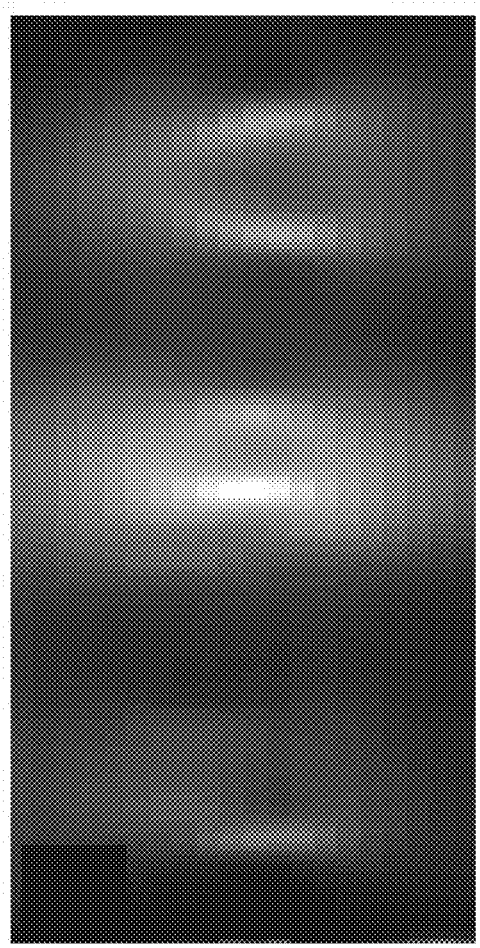
FIG. 30B shows an intrinsic MPI image of the CAL phantom showing correspondence to the phantom image, according to embodiments of the present disclosure. The FOV was 4 cm×2 cm, and the pixel size was 200 micron×1 mm. The total imaging time was 28 seconds, not including robot movement.

In FIGS. 28A, 28B, 30A and 30B, images measured with the x-space MPI imager are shown. As seen in the images of the PSF in FIGS. 28A and 28B and line scans in FIGS. 29A and 29B, the FWHM in the normal axis was 4.6 times wider than the FWHM along the axis of the imager. The lower resolution in the normal axis agreed with the theoretical prediction in Eq. III.8. The measured FWHM being wider than the theoretical prediction may be attributed to the nanoparticle behaving differently than in our model, and the phantom being a line source rather than a point source. In certain embodiments, the imaging system may orient the magnetic fields differently so as to optimize the shape of the PSF. The "CAL" phantom image shown in FIG. 30B was a native two-dimensional MPI image without any sharpening or deconvolution and with full recovery of the fundamental frequency, which maintained the LSI properties of the system. As seen in FIG. 30B, the received image for the "CAL" phantom approximated the phantom itself.

The x-space technique described herein is a MPI imaging process. Three hypotheses were used, that the gradient creates a single FFP, the adiabatic Langevin model, and that the loss of the low frequencies is recoverable. These three hypotheses allowed for the analysis of the MPI imaging process. The experimental evidence presented herein showed that loss of low frequency information was recoverable.

In certain embodiments, x-space theory did not require a repeating sinusoidal excitation or specific Lissajous pulse sequence. The x-space formulation also included an image reconstruction technique that was robust, scalable, and faster than inversion of the system matrix and it did not require pre-characterization of the magnetic nanoparticles or system. In certain instances, the computation required for x-space reconstruction, required only a scaling and gridding. For example, the reconstruction code may reconstruct the received signal faster than an analog-to-digital converter was able to digitize data.

The intrinsic FWHM resolution predicted by the x-space analysis agreed with the non-deconvolved resolution limit. The 2D and 3D analysis presented herein extend these initial analyses to show that the intrinsic resolution changes with the orientation of the FFP movement sequence. In certain embodiments, increasing the apparent diameter of the SPIO magnetic core to 25 or 30 nm and compensating for relaxation effects increased the intrinsic resolution of the image.

In certain embodiments, MPI is a LSI system with the three hypotheses discussed herein, and the experimental results showed that the recovery of the first harmonic enabled experimental MPI systems to be accurately modeled as LSI.

Experiment 3

Experiments were performed to construct and test a MPI device based on x-space theory as described herein.
Imaging Hardware
The design criteria and the construction of a small scale MPI device to test x-space theory are described herein.
A. Gradient
MPI requires a large magnetic field gradient that selectively saturates magnetic nanoparticles. Since resolution improves strongly with increasing nanoparticle core diameter and weakly with increasing magnetic field gradient strength, each nanoparticle size requires a different strength gradient to achieve a target resolution. In certain instances, using larger nanoparticles may increase resolution. In some instances, superparamagnetic nanoparticles may have an average diameter of 20 nm. In some cases, a commercially available nanoparticle tracer, Resovist (Bayer-Schering) was used, which has a signal very similar to a nanoparticle with 17±3.4 nm core diameter.

A 6.0 T/m (3.0 T/m transverse to the bore) gradient was built with permanent magnets using the magnet configuration shown in FIG. 31. The gradient was built using two opposed NdFeB ring magnets (ID=8.89 cm, OD=14.6 cm, THK=3.2 cm) mounted on G10 backing plates. The permanent magnets generated a 6.0 T/m gradient down the bore, and 3.0 T/m transverse to the bore. With Resovist particles, this enabled 1.6 mm resolution down the bore (see Eq.6). Because of the reduced transverse field gradient strength and since excitation was not performed in a transverse axis, the resolution equation (Eq. 7) predicted that the transverse resolution was 7.4 mm, or 460% greater than the collinear PSF. Inside the bore was a 2.5 mm thick, water cooled, copper eddy current shield that gave both mechanical rigidity and magnetically isolated the bore from the surrounding environment.

In some cases, the temperature coefficient of rare Earth magnets was typically 1 ppt/C, which would require miliKelvin temperature stability for NMR/MRI applications. However, for MPI applications, several degree temperature variations were well tolerated.
B. Excitation and Reception
In certain embodiments, the transmit chain excited the sample with a pure sinusoid with no energy content above the excitation frequency. The receive chain received a wide bandwidth signal, and at the same time suppressed the fundamental frequency. The transmit-receive filters were designed as shown in FIG. 35.

The resonant transmit coil ($f_0$=19 kHz) was wound with 10 gauge square magnet wire and was driven by a high power linear amplifier filtered by a three stage low pass filter. The transmit filter achieved 60 dB of isolation at 2× the fundamental signal and 65 dB isolation at 3× the fundamental signal. The transmit coil generated 30 mTpp with a peak power output of 5 kW. In some instances, a portion of the power output of the transmit coil was dissipated as heat in the water cooled eddy current shield. The receive coil was wound in a gradiometer-like configuration inside the transmit coil to minimize total shared flux. The receive coil had a sensitivity of $B_1$=XX T/A to the sample inside the bore and a DC resistance of XX ohms. The signal from the receive coil was notch filtered by a resonant filter, and amplified by a battery-powered low noise pre-amplifier (Stanford Research Systems SRS560). The signal was further conditioned by a noise matched 8th order analog Butterworth high-pass filter ($F_{3\ dB}$=25 kHz, Stanford Research Systems SIM965), followed by a second stage of amplification (Stanford Research System SIM911). The signal was digitized at 1.25 MSPS (National Instrument, NI-6259), digitally phase corrected, low pass filtered at 200 kHz, and gridded to the instantaneous position of the FFP.

Figure 36A:
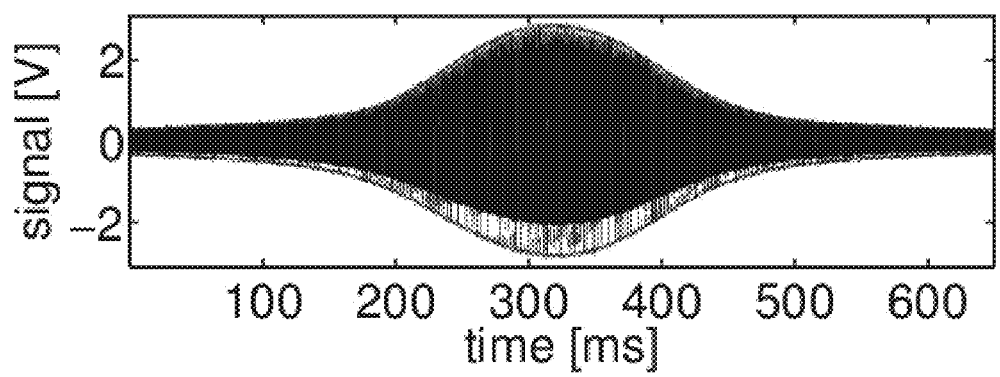
FIGS. 36A and 36B show graphs of measured signal showing phase corrected signal from a single scan across a point source in z and y, according to embodiments of the present disclosure.
Figure 36B:
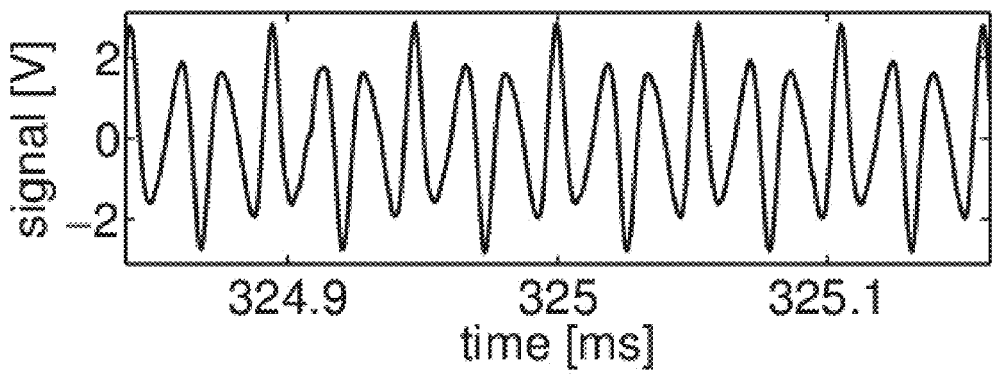

In certain cases, it was desirable to have a high power transmit filter with sufficient rejection of noise above the fundamental frequency. For the phantoms shown in the accompanying figures, the feedthrough of the second and third multiples of the fundamental frequency was about half of the size of the MPI signal from the phantoms. To counteract this, a baseline image with no sample in the bore was taken and subtracted from the received signal. However, in some instances, the feedthrough drifted and remained the dominant noise source.
Results and Discussion
The signal received by the x-space scanner had high SNR and repeatability. In FIGS. 36A and 36B, the phase corrected signal received by the x-space imager for a point source sample located at the origin is shown. The amplitude of the signal slowly changed as the average position of the FFP was scanned along the y axis.

X-space theory was used to convert the raw signal into an image and to make predictions regarding signal, PSF, resolution, bandwidth, and linearity. In this section x-space theory predictions were compared with experimental results. Two complex phantoms were imaged to demonstrate the flexibility of x-space imaging.
A. Partial Field of View Imaging
In partial field of view imaging, overlapping partial field of views were taken, which were reassembled into the full field of view. In FIGS. 37A, 37B and 37C, an illustration of how the raw gridded signal was baseline corrected before it was assembled into a full field of view image is shown. The assumption that a DC offset can approximate the lost information from removing the fundamental accurately enabled reconstruction.

B. PSF

Figure 38A:
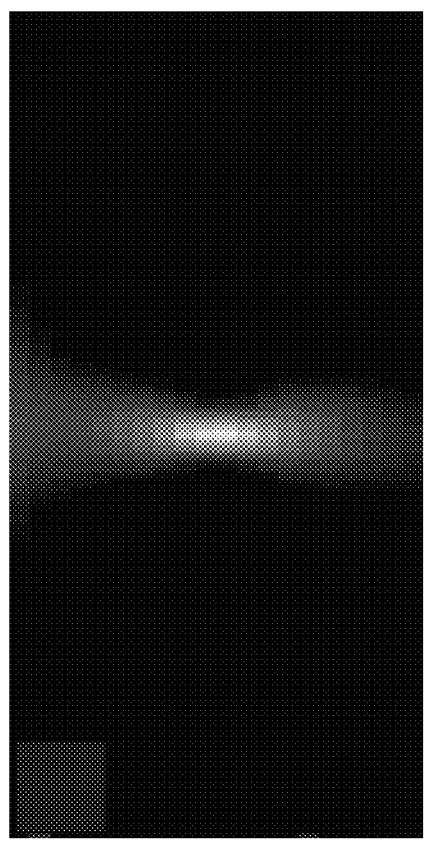
FIGS. 38A and 38B show graphs of a comparison between measured and theoretical collinear component of the PSF, according to embodiments of the present disclosure. The measured FWHM was 1.6 mm along the imager bore and 7.4 mm transverse to the imager bore. The field of view was 4 cm×2 cm, and the total imaging time was 28 seconds, not including robot movement.
Figure 38B:
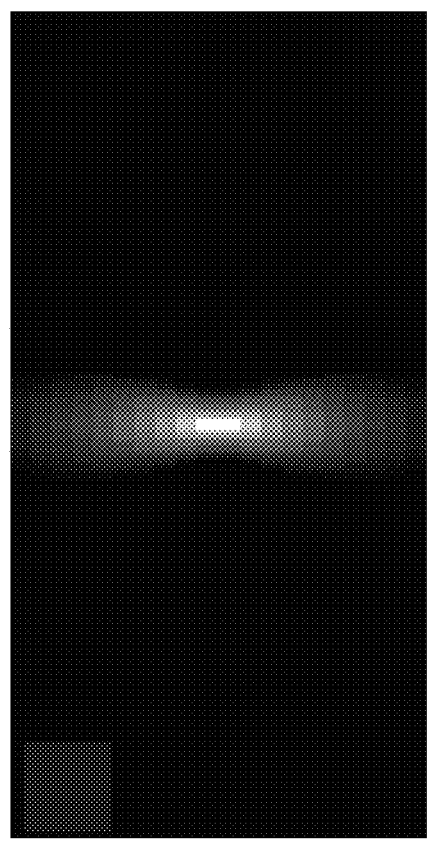

X-space theory predicted the shape of the collinear PSF. By imaging a phantom smaller than the intrinsic resolution of the system, the measured point spread function of the system was estimated. As shown in FIGS. 38A and 38B, the point spread function matched the theoretical prediction.

To calculate the theoretical point spread function, the nanoparticle distribution was determined by calculating the theoretical point spread function as:

$$IMG(x) = \int_d \tilde{x}(u_d; \mu, \sigma) k(u_d) \hat{x}_s \cdot h(u_d, x) \hat{x}_s du_d$$

where the distribution of diameters Band $f_x$ was integrated as a lognormal distribution function with mean $\mu$ and standard deviation $\sigma$. The signal was weighted by k because the signal was proportional to the magnetic moment m (See Eq. 1).

For the adiabatic assumption, it was assumed that the magnetic nanoparticle remained aligned with the locally experienced magnetic field vector. For example, if a single magnetic nanoparticle was placed in the imager, the magnetic nanoparticle moment may always be pointing at the FFP. Introducing a single nanoparticle, the magnetic moment "flipped" to follow the FFP as the FFP passed over the nanoparticle. Since inductive detection of the signal was used, the flipping of the moment induced a signal "blip" in the receiver coil. If the movement of the FFP was off axis so that the FFP did not pass directly over the nanoparticle, the nanoparticle flipped slower, and so the signal "blip" was smaller and more spread out. Consequently, the PSF had the best signal and resolution when the FFP passed directly over the nanoparticle, and widened when the FFP no longer passed directly over the nanoparticle.

C. Resolution

The intrinsic resolution of the system may be relevant to building a clinically relevant imaging system. As seen in the PSF image (FIGS. 38A and 38B), MPI resolution was a fundamental property of the gradient strength and nanoparticle properties, and did not increase by increasing SNR or image reconstruction techniques.

Figure 39A:
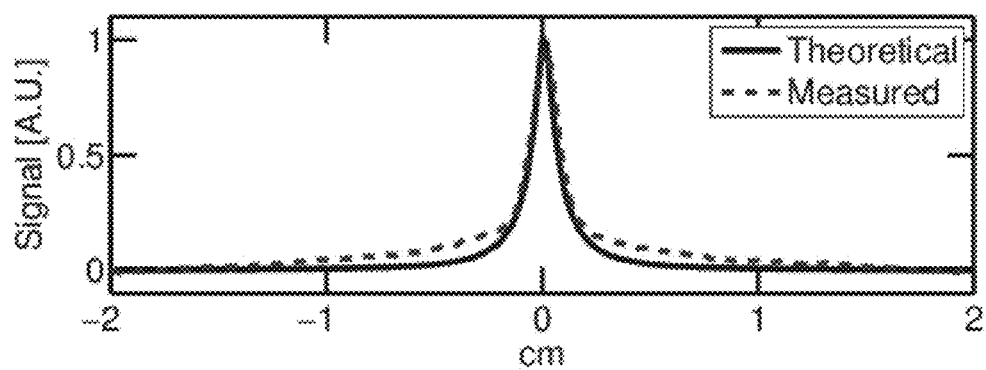
FIGS. 39A and 39B show graphs of profiles across the point spread function, which show good agreement between theoretical and measured values, according to embodiments of the present disclosure. Theoretical PSF assuming SPIO nanoparticle of lognormal size distribution with d=17±4 nm. The PSF phantom was a 400 micron ID tubing filled with Resovist oriented perpendicular to the bore.
Figure 39B:
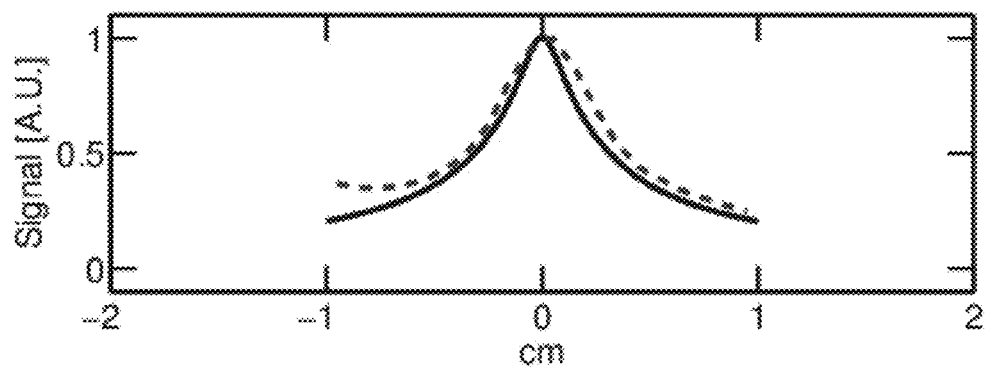

In FIGS. 39A and 39B, theoretical and measured projections were compared across the PSF. The theoretical and measured projections showed close correspondence, giving a 1.6 mm resolution down the bore, which matched the theoretically expected resolution.

Figure 40:
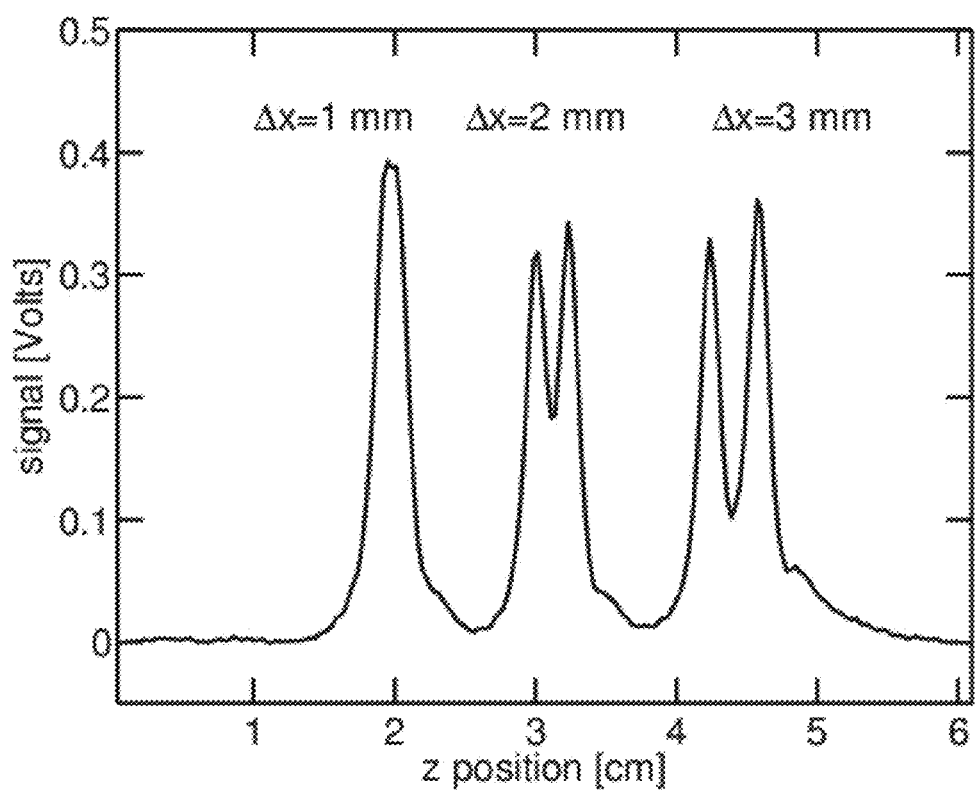
FIG. 40 shows a graph of a line scan of a linear Resolution phantom with point sources separated by 1 mm, 2 mm, and 3 mm, according to embodiments of the present disclosure. The 1 mm spaced samples were not resolvable as the spacing between them was less than the intrinsic resolution of the system (FWHM=1.6 mm).

FIG. 40 shows a resolution phantom that showed an image of point sources spaced below the resolution limit, slightly above the resolution limit, and above the resolution limit. The scan showed that the Houston criteria for resolution ($\Delta x_{min}$ FWHM) was an appropriate measure for resolution.

D. Bandwidth

Figure 41:
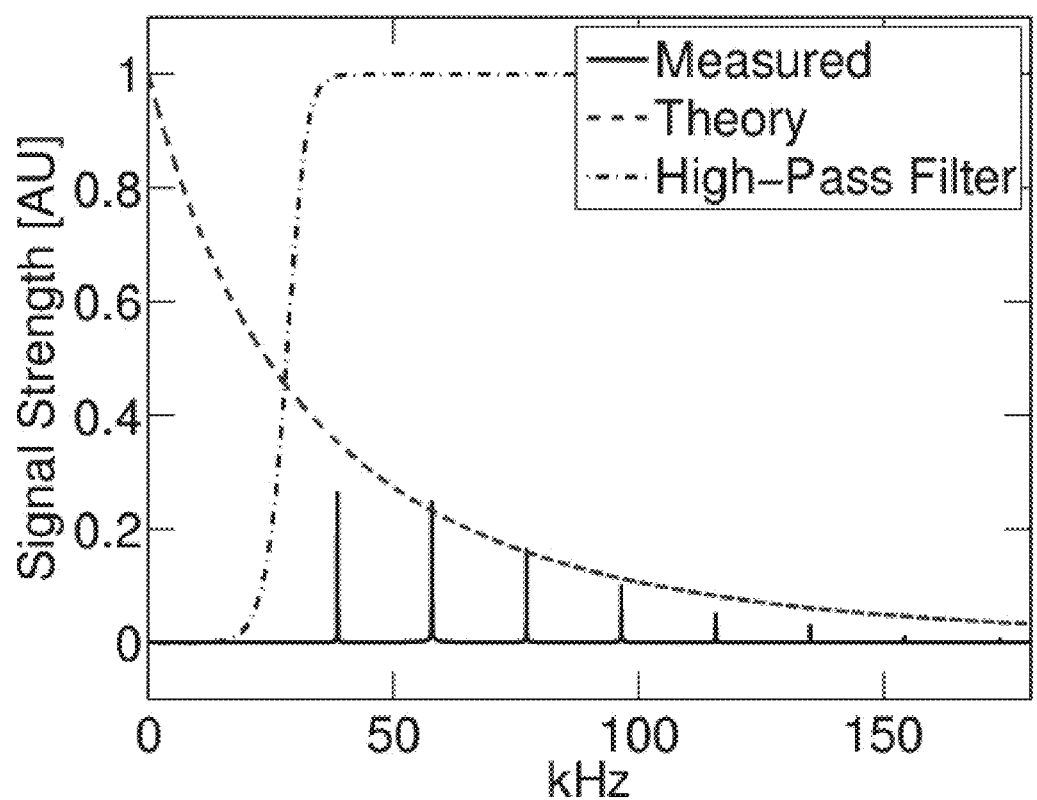
FIG. 41 shows a graph of a measured power spectrum of signal compared to theoretical power spectrum of signal assuming excitation amplitude of $30/\sqrt{2}$ $mT_{p-p}$, according to embodiments of the present disclosure. The harmonics were an artifact of repeatedly scanning over the sample. The measured signal corresponds to theory.

The reception bandwidth of the system was defined by the magnetic field slew rate and the properties of the magnetic nanoparticles. For a system used with 17±3.4 nm nanoparticles, the theoretical 3 dB bandwidth was $F_{3\ dB}$=30 kHz. Five times the theoretical bandwidth had no effect on the width of the point spread function, which corresponded to a total bandwidth of BW=150 kHz. The measured bandwidth compared to the theoretical bandwidth as shown in FIG. 41. Bandwidth was measured by stepping a line source through the bore while measuring the signal. The signal was broken down into segments and the maximum spectral content was found at all frequencies up to 200 kHz. The signal at twice the fundamental frequency was reduced from the theoretical value because our aggressive high pass filtering attenuated the signal.

In certain instances, increasing the bandwidth decreases SNR without improving resolution. Harmonic number was not considered when choosing the system bandwidth, as the number of harmonics were an artifact of a repeating excitation and not a fundamental MPI property.

E. Linearity and Shift Invariance

In certain cases, MPI is LSI when used for clinical imaging so that the images represent both the location and quantity of magnetic nanoparticles without image artifacts.

Figure 42:
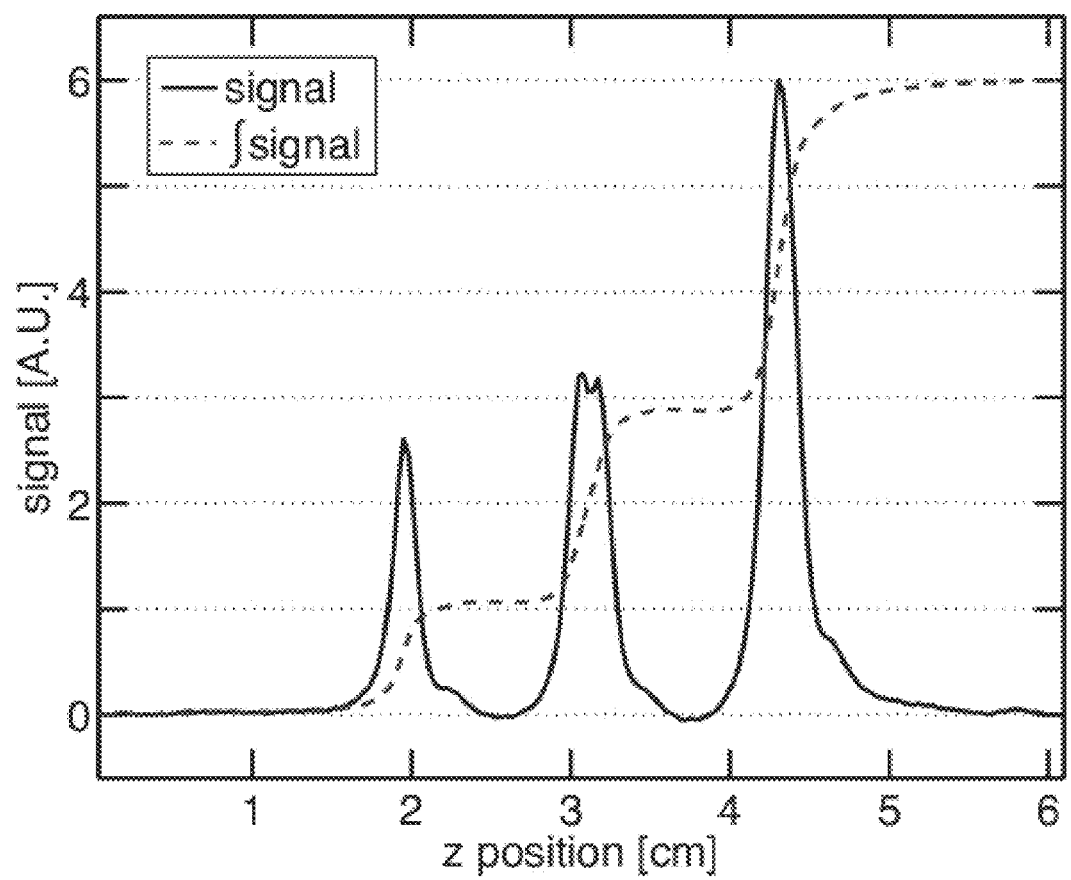
FIG. 42 shows a graph of an image of phantom (solid line) composed of sample composed of linearly increasing quantities of iron oxide tracer (1, 2, and 3) superimposed with the integral of the line scan (dotted line), according to embodiments of the present disclosure. The phantom demonstrates that signal was linear with the quantity of iron oxide tracer.

To test linearity, a linear (FIG. 42) phantom was built, which showed a line scan through a sample with linearly increasing quantities of magnetic tracer. The image showed both the reassembled signal and the integral of the signal. The integral of the signal showed good linearity of the system. As can be seen, MPI is a linear imaging system whose signal was proportional to the quantity of magnetic tracer. The resolution phantom (FIG. 40) also doubled as a test of shift invariance. As shown in the figures, MPI was linear and shift invariant following recovery of the DC offset.

F. Complex Phantoms

To demonstrate the potential of MPI for imaging complex phantoms, a "CAL" phantom and an analogue of an angiography phantom were imaged.

Figures 43A, 43B, 43C:
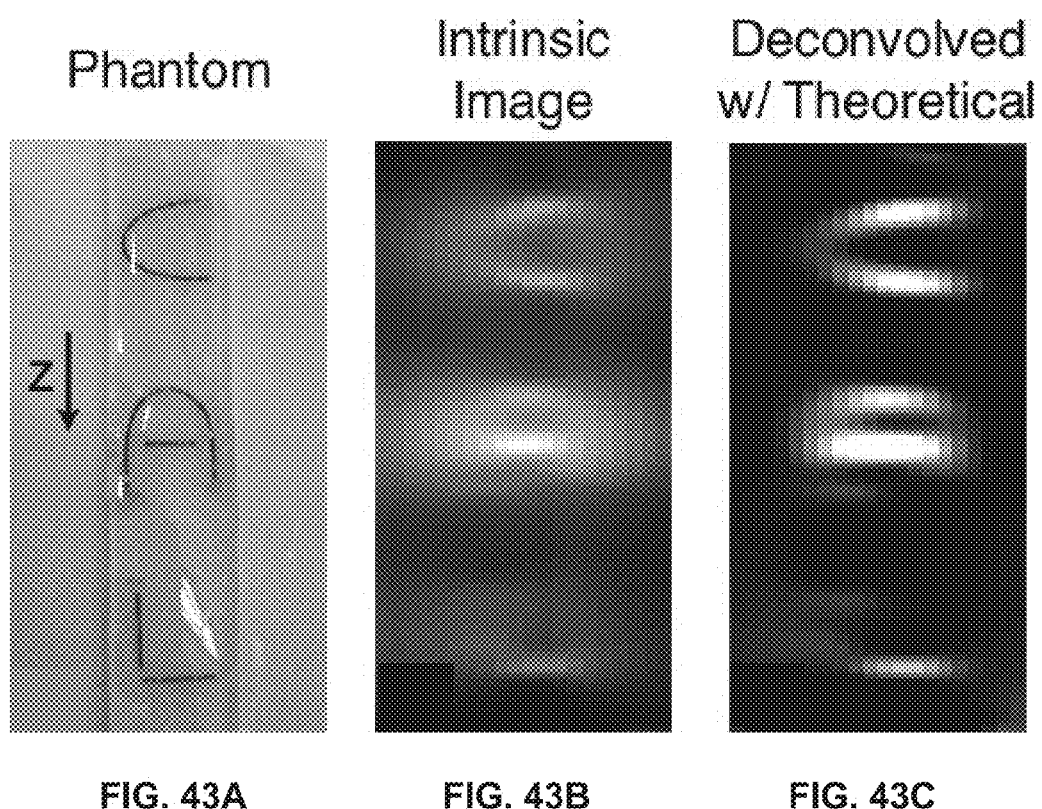
FIG. 43A shows a photograph of a "CAL" phantom image built using 400 micron ID tubing filled with undiluted tracer and encapsulated, according to embodiments of the present disclosure.
FIG. 43B shows the intrinsic MPI image of the CAL phantom showing correspondence to the phantom image, according to embodiments of the present disclosure.
FIG. 43C shows a Wiener filtered image of intrinsic image, according to embodiments of the present disclosure. The FOV was 4 cm×2 cm, and the pixel size was 200 micron×1 mm. The total imaging time was 28 seconds, not including robot movement.

The CAL phantom (FIGS. 43A, 43B and 43C) showed that the system formed a complex image that exhibited both linearity and shift invariance. The resolution down the bore was greater than the transverse resolution. Despite the difference the resolution between the two axes, the resulting image was clear and readable. The deconvolved image, which was deconvolved with the theoretical point spread function, was visually improved.

Figure 44A:
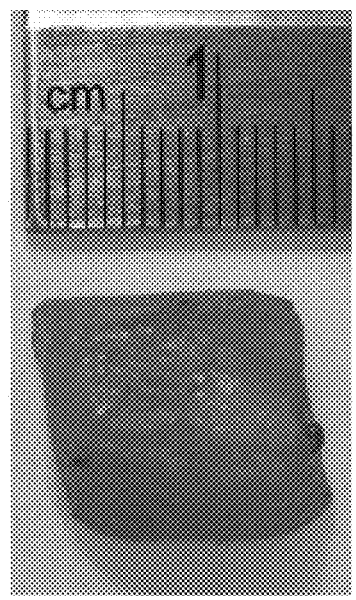
FIG. 44A shows a photograph of a preserved chicken phantom.
Figure 44B:
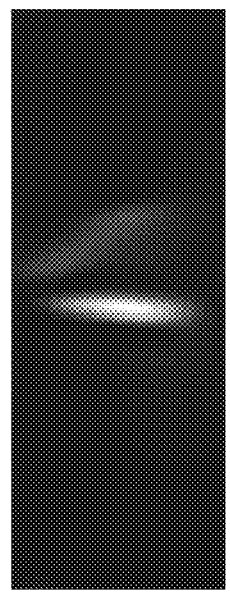
FIG. 44B shows a Wiener filtered image of the phantom image, according to embodiments of the present disclosure. The chicken tissue itself does not appear in the MPI image, thus there is no background to the image.

The angiography phantom (FIGS. 44A and 44B) was similar in shape to the branching of coronary arteries in the heart. The phantom was 400 micron ID tubes filled with undiluted tracer embedded in raw chicken tissue. Since tissue gave no MPI signal, the imager saw through the tissue without attenuation. The resulting image was simply the PSF convolved with the original magnetization density. In some instances, MPI may be useful for angiography.

Experiment 4

A. Hardware

To test the relationship between x-space theory and bandwidth, achievable resolution and SNR, a three-dimensional MPI scanner was built. The system was constructed with permanent magnet gradient (6 T/m down the bore and 3 T/m transverse to the bore) and an excitation coil in one dimension collinear to the bore. The FFP was rapidly scanned using the resonant transmit coil and the signal produced was received with a coil wound collinear to the transmit coil. The receive coil received the collinear component of the changing magnetization. The transmit and receive coils were collinear with the large gradient along the bore, which was twice the magnitude of the gradient transverse to the bore. In some instances, the resolution in the transverse direction was less than the resolution in the direction along the bore.

The resonant excitation coil generated 30 mT peak-to-peak at 20 kHz and was driven by an audio amplifier (AE Techron LVC5050, Elkhart, Ind., USA) with ~5 kW of instantaneous power at a pulsed 2% duty cycle. In some instances, a portion of the power of the excitation coil was dissipated in a water cooled eddy current shield that isolated the transmit and receive coils from the permanent magnet gradient. The signal from the receive coil was filtered by a passive notch filter, amplified by a FET input ($e_n$=4 nV/$\sqrt{Hz}$) battery powered preamplifier (SR560, Stanford Research Systems), and high-pass filtered at 30 kHz (SIM965, Stanford Research Systems). Following the analog signal chain, the signal was digitized by a 16-bit data acquisition system with a 1.25 MSPS sampling rate (National Instruments USB-6259, Austin, Tex., USA), phase corrected, and low-pass filtered at 400 kHz. The system was controlled by custom software written in MATLAB (Mathworks MATLAB, Natick, Mass., USA).

B. Imaging

The 30 mT peak-to-peak excitation enabled a partial FOV of approximately 0.5 cm along the z-axis. The signal for the received partial FOV was scaled to the instantaneous speed of the FFP, gridded to the instantaneous location of the FFP, and thus assigned to a physical location on the phantom. The phantom was stepped in 100 μm to 2.5 mm increments along the z-axis, acquiring a partial FOV line scan at each step.

Following data acquisition, the raw data was gridded using x-space theory to form a partial line scan. The partial line scans were reassembled by estimating the missing DC offset from scan to scan to generate an assembled full FOV of up to 8 cm along the z-axis.

Phantoms were constructed using 400 micron ID tubing filled with undiluted SPIO Resovist tracer (Bayer-Schering). The resolution phantom was constructed using three sets of tubing separated by 1 mm, 2 mm, and 3 mm, respectively. The intrinsic resolution of the system was approximately 1.6 mm, so this resulted in one set of points below the resolvability limit, slightly above the limit, and solidly above the limit.

C. Results and Discussion

Figure 48A:
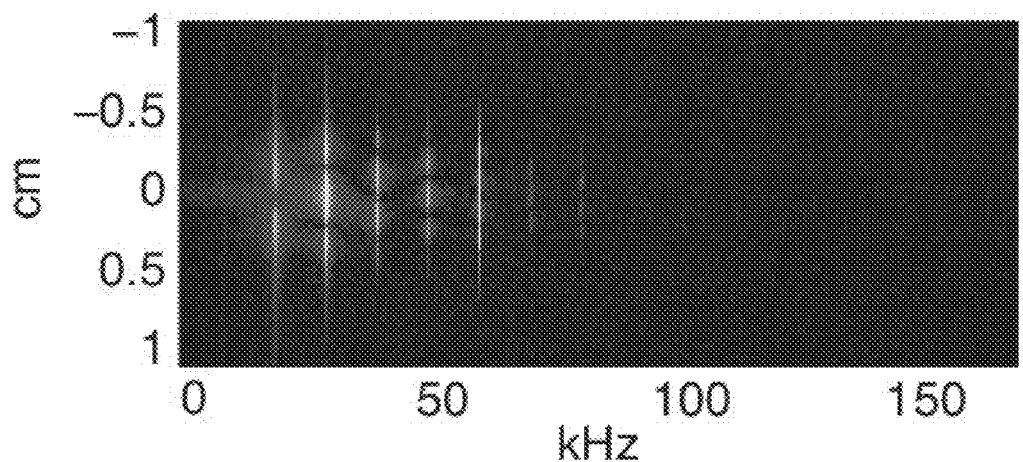
FIG. 48A shows an image of measured signal power (in dB) as a function of position of a point source.
Figure 48B:
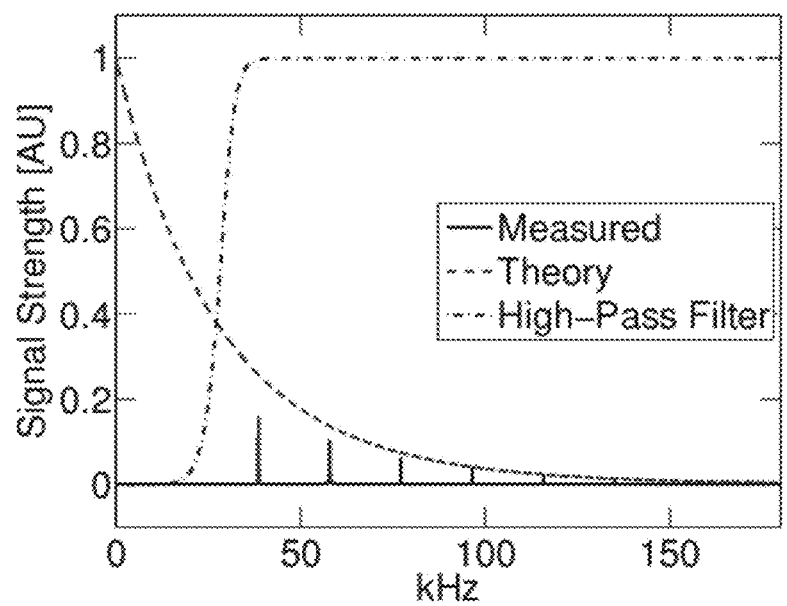
FIG. 48B shows a graph of maximum measured signal power over all point source positions, according to embodiments of the present disclosure.
Figure 48C:
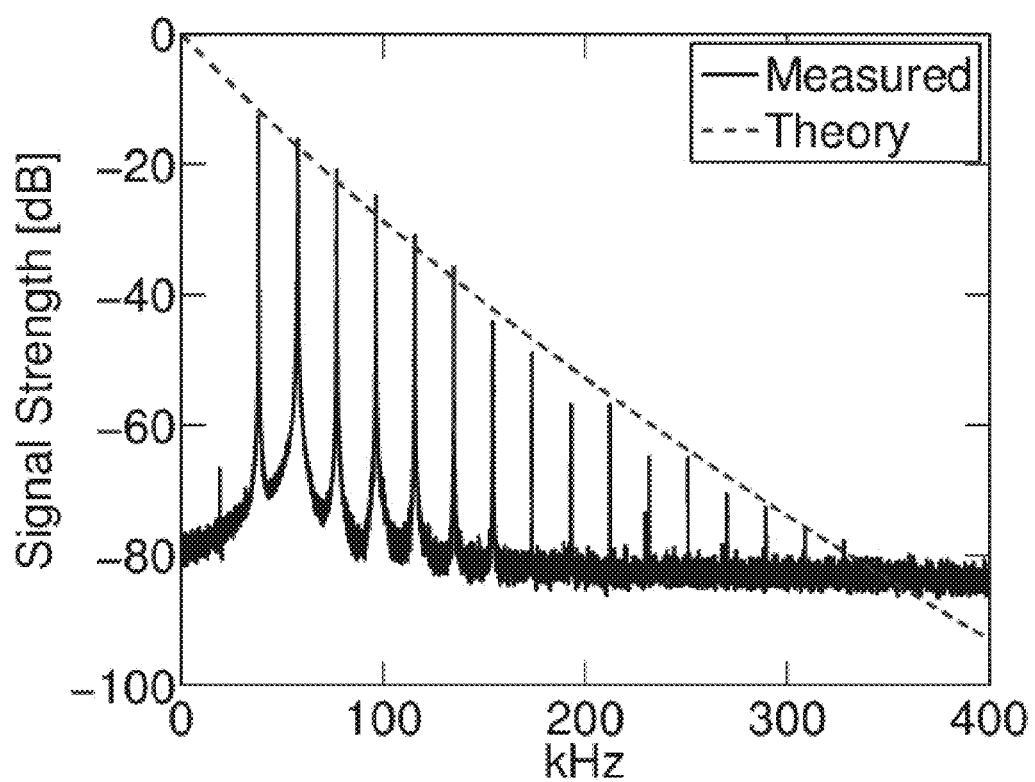
FIG. 48C shows a graph of the log of the measured signal power, according to embodiments of the present disclosure. The theoretical MPI signal bandwidth was comparable to the measured signal when assuming RMS FFP movement speed. The linear scale was logical for viewing the signal, as continuing to increase the receive bandwidth beyond 200 kHz did not improve the resolution. The theoretical particle in the bandwidth calculation had a lognormal distribution with mean diameter and standard deviation d=18±1.5 nm. The second harmonic was slightly reduced due to analog filtering of the fundamental frequency.

In FIGS. 48A, 48B and 48C, the experimental signal power is shown as a function of bandwidth compared with the theoretical bandwidth power. Bandwidth usage was calculated by moving a point source down the bore in 200 micron increments and taking a spectrum at each position, ensuring that the phantom passed through the center of the bore. An image of the raw frequency data is shown in FIG. 48A. The signal summed across all the point source locations is shown in FIG. 48C. The signal power in decibels is shown in FIG. 48B.

Figure 49C:
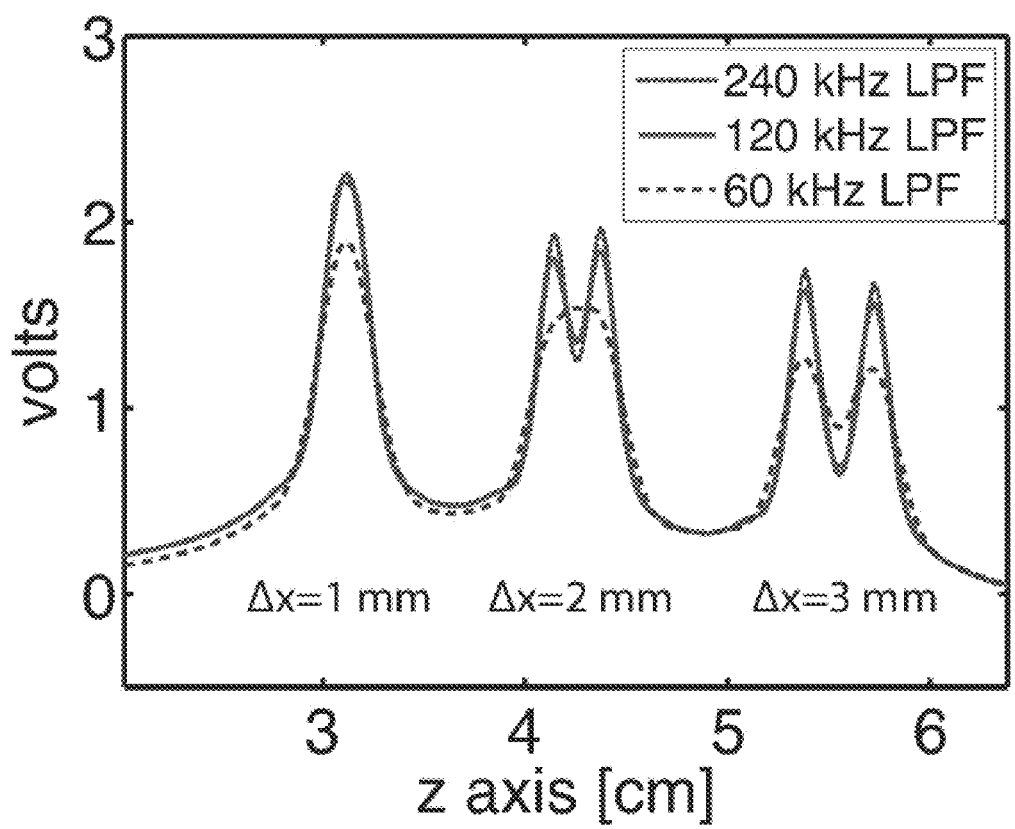
FIG. 49C shows a graph of the assembled data showing the resolution phantom of the reconstructed image with three different low pass filters on the raw data before gridding, according to embodiments of the present disclosure. The image was taken with a 5 mm partial FOV with 80% overlap. Total scan time not including robot movement was 0.8 seconds.

FIG. 49A shows the one-dimensional MPI images of a resolution phantom. Prior to assembly, the partial field of view scans were baseline corrected so that they maximized their overlap. An example of unassembled data following the scaling and gridding step is shown in FIG. 49B. The baseline corrected image was assembled into a one-dimensional image as seen in FIG. 49C.

Figure 50:
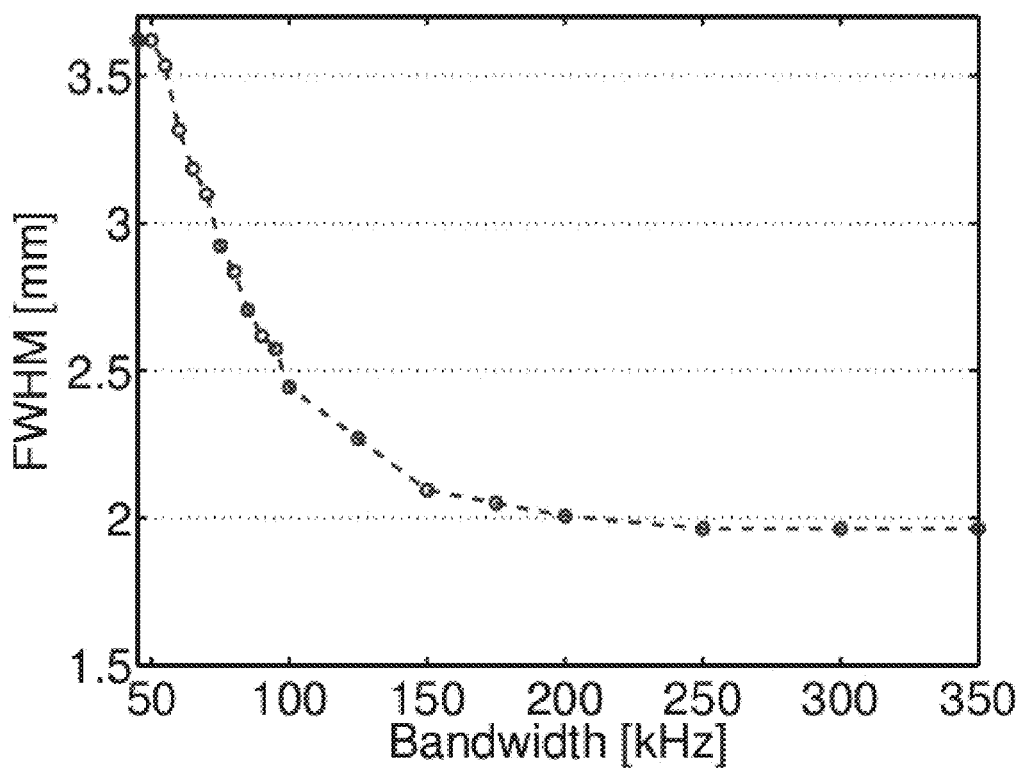
FIG. 50 shows a graph of measured FWHM as a function of bandwidth, according to embodiments of the present disclosure. The point source was undiluted Resovist in polyethylene tubing with ID=400 µm. Increasing the bandwidth above 200 kHz did not substantially increase resolution.

In FIG. 50 shows the measured resolution of the system as a function of the input bandwidth without any deconvolution. The measured FWHM of 2 mm was wider than the system resolution because the point source had a diameter of 400 μm. In some cases, the FWHM asymptotically improved with increasing bandwidth.

Figure 51:
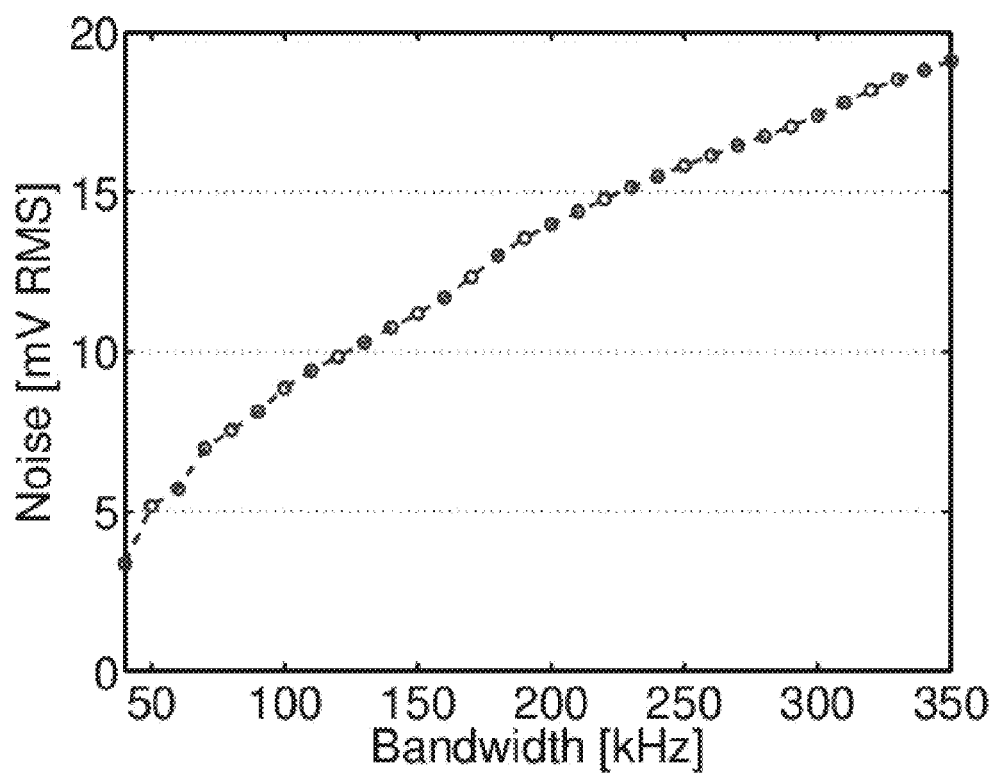
FIG. 51 shows a graph of the measured RMS noise of a scan post-gridding improves with decreasing system bandwidth, according to embodiments of the present disclosure.
Figure 52:
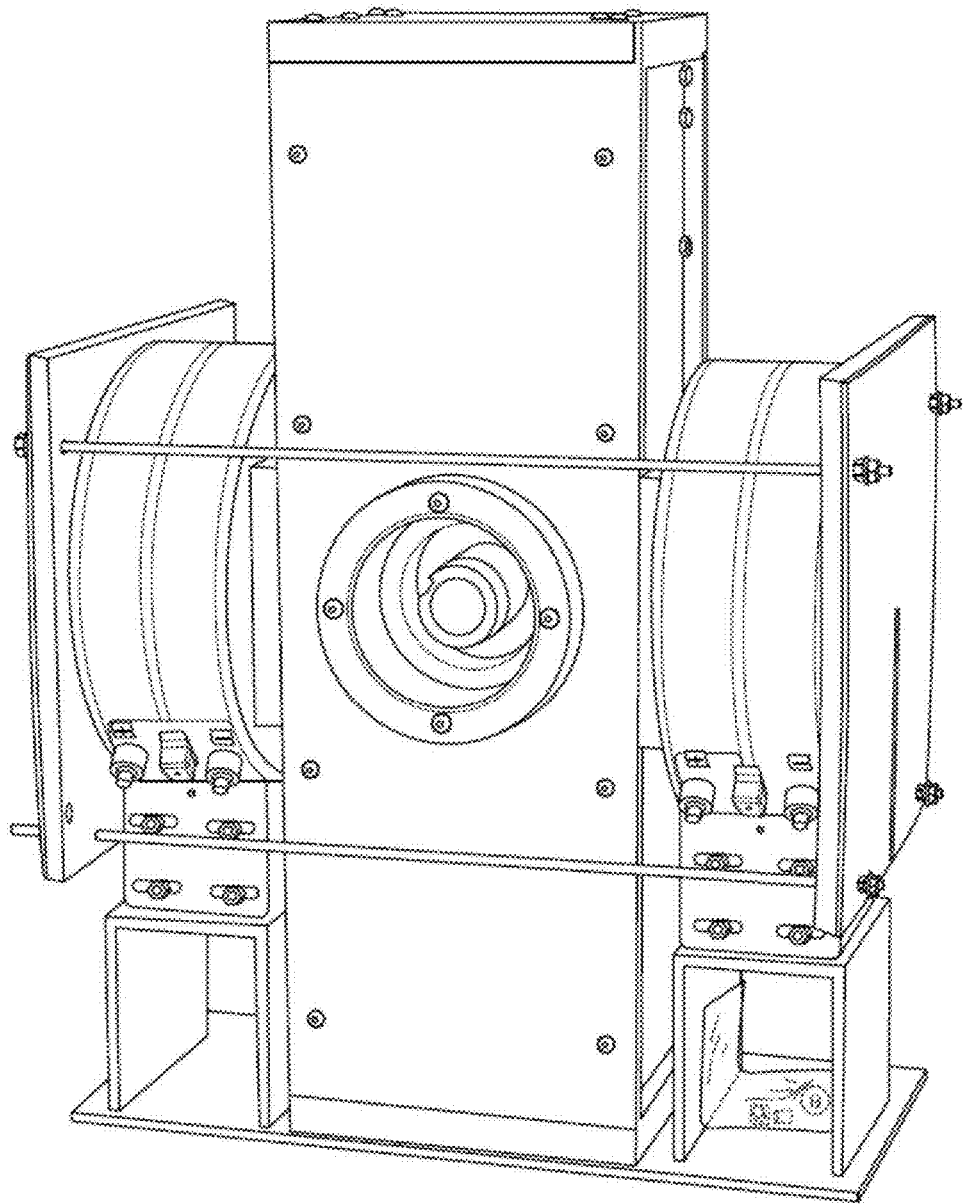
FIG. 52 shows a photographic image of a magnetic particle imaging device configured to produce a non-saturating magnetic field line and include two permanent magnets positioned on opposing sides of the central imaging area of the device, according to embodiments of the present disclosure. The device generated a 2.5 T/m gradient across a 4 inch magnet free bore.

In FIG. 51, the measured noise is shown as a function of the input bandwidth. The measured RMS noise increased with the system bandwidth. Continuing to increase the bandwidth beyond what was required for a target resolution decreased SNR and did not substantially increase resolution.

The optimal imaging bandwidth in x-space MPI required a tradeoff between achievable resolution and SNR. Like all Linear and Shift Invariant (LSI) imaging systems, the intrinsic resolution of MPI was not related to system SNR, and was instead a property of how the magnetic nanoparticle interacts with the gradient. However, the intrinsic resolution was degraded by the choice of a low pass filter, as shown in FIG. 50. In some instances, the noise increased with the bandwidth (see FIG. 51).

These results indicated that, when imaging Resovist magnetic particles, the signal bandwidth did not need to increase above 200 kHz for a 30 mT peak-peak magnetic field at 20 kHz. Continuing to increase the bandwidth did not increase the measured resolution appreciably, and increased the system noise. The value of this required bandwidth changed with the properties of the particle and the magnetic field slew rate. In certain embodiments, the system bandwidth may be reduced, decreasing resolution in order to improve SNR at the expense of resolution. For example, halving the receive bandwidth to 100 kHz theoretically improved SNR by more than forty percent, while decreasing the measured resolution by twenty percent. The experimental results indicated that ≈1.6 mm was the resolution of Resovist tracer in an MPI system with a 6 T/m gradient (FIG. 50).

The models indicated that using the root mean squared (RMS) magnetic field slew rate accurately modeled the system bandwidth requirements. While the peak FFP movement speed may be faster than the RMS speed, the FFP movement speed was averaged across the FOV.

Various other modifications and alternations in the structure and method of operation of the present disclosure will be apparent to those skilled in the art without departing from the scope and spirit of the present disclosure. Although the present disclosure has been described in connection with specific preferred embodiments, it should be understood that the present disclosure as claimed should not be unduly limited to such specific embodiments.

What is claimed is:

1. A magnetic particle imaging device, comprising:
a magnetic field generating apparatus arranged proximate an imaging region of the magnetic particle imaging device, the magnetic field generating apparatus being configured to produce a magnetic field within the imaging region of the magnetic particle imaging device such that the magnetic field will have a field-free region (FFR) for an object under observation that contains a magnetic tracer the magnetic field generating apparatus being further configured to produce an excitation magnetic field that induces a signal from the magnetic tracer in the object under observation;
a receiver arranged proximate the observation region, the receiver being configured to receive the signal from the magnetic tracer in the observation region;
a radio-frequency (RF) shield configured to isolate the receiver and the imaging region therein; and
a signal processor configured to be in communication with the receiver, the signal processor being configured to convert the signal into an image of the magnetic tracer.

2. The device of claim 1, wherein the magnetic field generating apparatus comprises at least two coaxially arranged magnetic field sources isolated outside of the RF shield and which create the FFR.

3. The device of claim 2, wherein the at least two magnetic field sources are permanent magnets.

4. The device of claim 2, wherein the magnetic field generating apparatus produces a magnetic field gradient ranging from 0.5 Tesla/meter to 30 Tesla/meter.

5. The device of claim 1, wherein the excitation magnetic field comprises a RF magnetic field.

6. The device of claim 5, wherein the excitation magnetic field further comprises an intermodulation excitation signal.

7. The device of claim 1, wherein the magnetic field generating apparatus further comprises a scanning magnetic field source arranged proximate the observation region, the scanning magnetic field source being configured to produce a scanning magnetic field that positions the FFR in the imaging region.

8. The device of claim 7, wherein the device is configured to produce a linearly varying signal with respect to a concentration of the magnetic tracer in the FFR.

9. The device of claim 1, wherein the receiver comprises a receiver coil with a Q factor of 100 or more.

10. The device of claim 1, wherein the receiver is configured to have a receive bandwidth ranging from 10 kHz to 1 MHz.

11. The device of claim 1, wherein the excitation magnetic field comprises an RF frequency source arranged within the RF shield and a low-frequency source arranged outside of the RF shield,
wherein the low-frequency source provides a component of the excitation magnetic field that has a frequency lower than the RF frequency source.

12. The device of claim 1, wherein the RF shield is cooled.

13. The device of claim 1, wherein the RF shield is cooled using a circulating coolant.

14. The device of claim 13, wherein the circulating coolant is water.

15. The device of claim 1, wherein the RF shield comprises copper having a tube-like structure that contributes to mechanical rigidity of the device.

16. The device of claim 15, wherein the tube-like structure is formed from copper.

17. The device of claim 1, wherein the FFR and the excitation magnetic field are generated by a common magnetic field source.

18. The device of claim 1, wherein the magnetic field generating apparatus comprises at least one magnetic field source that produces the excitation magnetic field and which is arranged inside of the RF shield.

19. The device of claim 1, wherein the at least two magnetic field sources are electromagnets.

20. The device of claim 7, wherein the scanning magnetic field source is positioned outside of the RF shield.

21. The device of claim 7, wherein the FFR, the excitation magnetic field, and the scanning magnetic field are produced using the same magnets.

22. A method of producing an image of a magnetic tracer in a sample, comprising:
applying a magnetic field having a Field Free Region (FFR) to a sample containing magnetic tracer;
applying an excitation magnetic field to the sample to produce a detectable signal from the magnetic tracer;
receiving the signal from the magnetic tracer with a receiver wherein the receiver is shielded with an RF shield; and
analyzing the received signal to produce an image of the magnetic tracer in the sample.

23. The method of claim 22, further comprising applying a scanning magnetic field in superposition with the FFR magnetic field to position the FFR.

24. The method of claim 23, further comprising:
repositioning the FFR;
and
repeating the detecting.

25. The method of claim 24, wherein the analyzing comprises correlating the received signal to the position of the FFR when the signal was received.

26. The method of claim 24, wherein the analyzing comprises converting the received signals into partial field of view images.

27. The method of claim 26, wherein the analyzing further comprises combining the partial field of view images to produce the image of the magnetic tracer in the sample.

28. The method of claim 23, further comprising varying the strength of the magnetic field region having an FFR while applying the scanning magnetic field to produce images having different resolutions.

29. The method of claim 28, further comprising analyzing the images having different resolutions to determine low frequency image data.

30. The method of claim 22, wherein the applying the excitation magnetic field comprises applying an RF excitation magnetic field in superposition with the magnetic field having a FFR.

31. The method of claim 30, wherein the applying the excitation magnetic field further comprises applying an intermodulation signal to the magnetic tracer in the FFR from outside of the shielding.

32. The method of claim 23, wherein the analyzing comprises correlating the received signal to the position of the FFR when the signal was received.

33. The method of claim 23, wherein the analyzing comprises converting the received signals into partial field of view images.

34. The method of claim 33, wherein the analyzing further comprises combining the partial field of view images to produce the image of the magnetic tracer in the sample.

35. A method of producing an image of magnetic tracer in a subject, comprising:
administering magnetic tracer to a subject;
positioning the subject in a magnetic particle imaging device;
applying a magnetic field having a Field Free Region (FFR) to a sample containing magnetic tracer;
applying an excitation magnetic field to the sample to produce a detectable signal from the magnetic tracer;
receiving the signal from the magnetic tracer with a receiver wherein the receiver is shielded with an RF shield; and
analyzing the received signal to produce an image of the magnetic tracer in the sample.

* * * * *